US011859041B2

(12) United States Patent
Bischof et al.

(10) Patent No.: US 11,859,041 B2
(45) Date of Patent: Jan. 2, 2024

(54) MODULATING CO-MONOMER SELECTIVITY USING NON-COVALENT DISPERSION INTERACTIONS IN GROUP 4 OLEFIN POLYMERIZATION CATALYSTS

(71) Applicant: CHEVRON PHILLIPS CHEMICAL COMPANY LP, The Woodlands, TX (US)

(72) Inventors: Steven M. Bischof, Humble, TX (US); Qing Yang, Bartlesville, OK (US); Orson L. Sydora, Sugar Land, TX (US); Graham R. Lief, Bartlesville, OK (US); Richard M Buck, Bartlesville, OK (US); Daniel H. Ess, Provo, UT (US); Steven M. Maley, Orem, UT (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 22 days.

(21) Appl. No.: 17/403,527

(22) Filed: Aug. 16, 2021

(65) Prior Publication Data
US 2023/0098789 A1 Mar. 30, 2023

(51) Int. Cl.
| | |
|---|---|
| C08F 4/76 | (2006.01) |
| G16C 10/00 | (2019.01) |
| G16C 20/00 | (2019.01) |
| G06N 5/00 | (2023.01) |
| C08F 10/00 | (2006.01) |
| C08F 4/6192 | (2006.01) |

(52) U.S. Cl.
CPC .............. C08F 4/76 (2013.01); C08F 10/00 (2013.01); G16C 10/00 (2019.02); G16C 20/00 (2019.02); C08F 4/61925 (2013.01); C08F 4/61927 (2013.01); C08F 2420/10 (2021.01); G06N 5/00 (2013.01)

(58) Field of Classification Search
CPC ........ G16C 20/00; G16C 20/10; G16C 20/50; G06N 5/00; G06N 20/00; C08F 4/61925; C08F 4/61927; C08F 4/64; C08F 4/65925; C08F 4/65927; C08F 210/16
See application file for complete search history.

(56) References Cited

U.S. PATENT DOCUMENTS

| | | | | |
|---|---|---|---|---|
| 4,931,417 A * | 6/1990 | Miya | ...................... | C08F 10/00 556/53 |
| 5,374,700 A * | 12/1994 | Tsutsui | .................. | C08F 210/16 526/348.3 |
| 5,504,232 A * | 4/1996 | Winter | ..................... | C08F 10/00 556/11 |
| 5,610,254 A * | 3/1997 | Sagane | ..................... | C08K 5/09 526/170 |
| 5,629,254 A * | 5/1997 | Fukuoka | ................ | C07C 49/697 556/53 |
| 5,677,408 A * | 10/1997 | Ueda | ...................... | C07C 49/697 526/170 |
| 6,482,902 B1 * | 11/2002 | Bohnen | .................... | C08F 10/00 526/132 |
| 6,492,539 B1 * | 12/2002 | Bingel | ..................... | C07C 49/67 502/103 |
| 7,300,904 B2 | 11/2007 | Dixon | | |
| 7,361,623 B2 | 4/2008 | Dixon | | |
| 7,446,216 B2 * | 11/2008 | Voskoboynikov | .......................... | C08F 4/65908 502/103 |
| 7,554,001 B2 | 6/2009 | Dixon | | |
| 7,709,670 B2 * | 5/2010 | Voskoboynikov | .......................... | C08F 4/65908 556/53 |
| 7,994,363 B2 | 8/2011 | Gao | | |
| 8,252,956 B2 | 8/2012 | Gao | | |

(Continued)

FOREIGN PATENT DOCUMENTS

| | | | | |
|---|---|---|---|---|
| EP | 2 966 096 A1 * | 1/2016 | ............ | C08F 4/6592 |
| EP | 3322680 A1 | 5/2018 | | |

(Continued)

OTHER PUBLICATIONS

A. Subha Mahadevi, et al., "Cooperativity in Noncovalent Interactions," Am. Chem. Soc., Chem. Rev., 116, 2016, pp. 2775-2825.
A. Vaughn, et al., "Industrial Catalysts for Alkene Polymerization," Polymer Science: A Comprehensive Reference, vol. 3, 2012, pp. 657-672.
Aayush R. Singh, et al., "Predicting Chemical Reaction Barriers with a Machine Learning Model," Catalysis Letters, 149, 2019, pp. 2347-2354.
Adam J. Rucklidge, et al., "Ethylene Tetramerization with Cationic Chromium(I) Complexes," Organometallics, vol. 26, No. 10, 2007, pp. 2782-2787.
Aditya Nandy, et al., "Machine Learning Accelerates the Discovery of Design Rules and Exceptions in Stable Metal-Oxo Intermediate Formation," ACS Catal., 9, 2019, pp. 8243-8255.

(Continued)

Primary Examiner — Rip A Lee
(74) Attorney, Agent, or Firm — Eversheds Sutherland (US) LLP

(57) ABSTRACT

This disclosure provides new methods for the design and development of ethylene polymerization catalysts, including Group 4 metallocene catalysts such as zirconocenes, which are based on an improved ability to adjust co-monomer incorporation into the polymer. Computational analyses with and without dispersion corrections revealed that designing catalyst scaffolds which induce stabilizing non-covalent dispersion type interactions with incoming α-olefin co-monomers can be used to modulate co-monomer selectivity into the polyethylene chain. Demonstrated herein is a lack of correlation of computed $\Delta\Delta G^{\ddagger}$ values against experimental $\Delta\Delta G^{\ddagger}$ values when the dispersion correction (D3BJ) was disabled, and B3LYP was used in the absence of Grimme's D3 dispersion and Becke-Johnson (BJ) dampening, but a correlation of computed against experimental $\Delta\Delta G^{\ddagger}$ with B3LYP+D3BJ, which are used to design new catalyst scaffolds.

23 Claims, 11 Drawing Sheets
(6 of 11 Drawing Sheet(s) Filed in Color)

(56) References Cited

U.S. PATENT DOCUMENTS

| | | | |
|---|---|---|---|
| 8,680,003 B2 | 3/2014 | Sydora | |
| 8,865,610 B2 | 10/2014 | Sydora | |
| 9,283,555 B2 | 3/2016 | Sydora | |
| 9,309,340 B2 * | 4/2016 | Ishihama | C08L 23/0815 |
| 10,183,960 B1 | 1/2019 | Bischof | |
| 10,196,328 B2 | 2/2019 | Kilgore | |
| 10,435,336 B2 | 10/2019 | Kreischer | |
| 10,493,442 B2 | 12/2019 | Bischof | |
| 2010/0274065 A1 | 10/2010 | Sydora | |
| 2012/0309965 A1 | 12/2012 | Sydora | |
| 2019/0092708 A1 | 3/2019 | Bischof | |
| 2019/0106365 A1 | 4/2019 | Kilgore | |
| 2019/0263732 A1 | 8/2019 | Kreischer | |

FOREIGN PATENT DOCUMENTS

| | | | |
|---|---|---|---|
| EP | 3463654 A1 | 4/2019 | |
| WO | 2007024504 A1 | 3/2007 | |
| WO | 2010051415 A1 | 5/2010 | |
| WO | 2017011127 A1 | 1/2017 | |
| WO | 2017209959 A1 | 12/2017 | |
| WO | WO 2019/190883 A1 * | 10/2019 | B01J 19/00 |
| WO | 2021252624 A1 | 12/2021 | |

OTHER PUBLICATIONS

Adolfo Zambelli, et al., "Copolymerization of Ethylene With Propene in the Presence of Homogeneous Catalytic Systems Based on Group 4 Metallocenes and Methylalumoxane: Implications of the Ractivity Ratios on the Reaction Mechanisim," Makromol. Chem., Rapid Commun., 12, 1991, pp. 523-528.

Alan Armstrong, et al., "The Houk-List Transition States for Organocatalytic Mechanisms Revisited," Royal Society of Chemistry, Chemical Science, 5, 2014, pp. 2057-2071.

Albert Poater, et al., "Theoretical Attempts: "In Silico Olefin Metathesis" —How Can Computers Help in the Understanding of Metathesis Mechanisms and in Catalysts Development?," Olefin Metathesis Theory Pract. 2014, pp. 483-494.

Aleksandr V. Marenich, et al., "Universal Solvation Model Based on Solute Electron Density and on a Continuum Model of the Solvent Defined by the Bulk Dielectric Constant and Atomic Surface Tensions," J. Phys. Chem. B, vol. 113, No. 18, 2009, pp. 6378-6396.

Althea S.-K. Tsang, et al., "Combining Experimental and Computational Studies to Understand and Predict Reactivities of Relevance to Homogeneous Catalysis," ChemPubSoc Europe, Chemistry A European Journal Concept, 20, 2014, pp. 16432-16441.

Analise C. Doney, et al., "Design of Organocatalysts for Asymmetric Propargylations Through Computational Screening," ACS Catalysis, 6, 2016, pp. 7948-7955.

Andreas Hansen, et al., "The Thermochemistry of London Dispersion-Driven Transition Metal Reactions: Getting the Right Answer for the Right Reason'," ChemPubSoc. Europe, Chemistry Open, 3, 2014, pp. 177-189.

Andreas Uhe, et al., "Automatic Analysis of Computed Catalytic Cycles," Software News and Update, J. Comput. Chem., 32, 2011, pp. 978-985.

Andrew F. Zahrt, et al., "Prediction of Higher-Selectivity Catalysts by Computer-Driven Workflow and Machine Learning," Asymmetric Catalysis, Science, vol. 363, 247, eaau5631, 2019, 12 pages.

Andrew J. Neel, et al., "Exploiting Non-Covalent π Interactions for Catalyst Design," Nature, vol. 543, Mar. 30, 2017, pp. 637-646.

Andrey A. Fokin, et al., "Stable Alkanes Containing Very Long Carbon-Carbon Bonds," Journal of the American Chem. Soc., 134, 2012, pp. 13641-13650.

Andy A. Thomas, et al., "Mechanistically Guided Design of Ligands That Significantly Improve the Efficiency of CuH-Catalyzed Hydroamination Reactions," J. Amer. Chem. Soc., 140, 2018, pp. 13976-13984.

Angelika Bruckner, et al., "Monitoring Structure and Valence State of Chromium Sites During Catalyst Formation and Ethylene Oligomerization by in Situ EPR Spectroscopy," Organometallics, vol. 27, No. 15, 2008, pp. 3849-3856.

Anna Tomberg, et al., "A Predictive Tool for Electrophilic Aromatic Substitutions Using Machine Learning," J. Org. Chem., 84, 2019, pp. 4695-4703.

Annette Bollmann, et al., "Ethylene Tetramerization: A New Route to Produce 1-Octene in Exceptionally High Selectivities," J. Am. Chem. Soc. 2004, 126, 14712-14713.

Anniina Laine, et al., "Effect of Ligand Structure on Olefin Polymerization by a Metallocene/Borate Catalyst: A Computational Study," Organometallics, 34, 2015, pp. 2415-2421.

Anthea Carter, et al., "High Activity Ethylene Trimerisation Catalysts Based on Diphosphine Ligands," The Royal Society of Chemistry, Chem. Comm., 2002, pp. 858-859.

Aria Mansouri Tehrani, et al., "Machine Learning Directed Search for Ultraincompressible, Superhard Materials," J. Am. Chem. Soc., 140, 2018, pp. 9844-9853.

Arne Haaland, et al., "On the Nature and Incidence of β-Agostic Interactions in Ethyl Derivatives of Early Transition Metals: Ethyltitanium Trichloride and Related Compounds," J. Am. Chem. Soc., 120, 1998, pp. 3762-3772.

Arno N.J. Blok, et al., "Mechanism of Ethene Trimerization at an ansa-(Arene)(Cyclopentadienyl) Titanium Fragment," Organometallics, vol. 22, No. 13, 2003, pp. 2564-2570.

Asif J. Chowdhury, et al., "Prediction of Adsorption Energies for Chemical Species on Metal Catalyst Surfaces Using Machine Learning," J. Phys. Chem. C., 122, 2018, pp. 28142-28150.

Axel D. Becke, "Density-Functional Thermochemistry. III. The Role of Exact Exchange," The Journal of Chemical Physics, 98 (7), 1993, pp. 5648-5652.

Benjamin A. Rizkin, et al., "Supervised Machine Learning for Prediction of Zirconocene-Catalyzed α-Olefin Polymerization," Chemical Engineering Science, 210, 2019, 115224, 12 pages.

Benjamin Meyer, et al., "Machine Learning Meets Volcano Plots: Computational Discovery of Cross-Coupling Catalysts," Chemical Science, 9, 2018, pp. 7069-7077.

Bowen Liu, et al., "Retrosynthetic Reaction Prediction Using Neural Sequence-to-Sequence Models," ACS Central Science, 3, 2017, pp. 1103-1113.

Brian D. Rekken, et al., "Dispersion Forces and Counterintuitive Steric Effects in Main Group Molecules: Heavier Group 14 (Si—Pb) Dichalcogenolate Carbene Analogues with Sub-90° Interligand Bond Angles," J. Amer. Chem. Soc., 135, 2013, pp. 10134-10148.

Bryan R. Goldsmith, et al., "Machine Learning for Heterogeneous Catalyst Design and Discovery," American Institute of Chemical Engineers, vol. 64, No. 7, 2018, pp. 2311-2323.

Carl Poree, et al., "A Holy Grail in Chemistry: Computational Catalyst Design: Feasible or Fiction?," Accounts of Chemical Research, 50, 2017, pp. 605-608.

Changwei Wang, et al., "The Self-Association of Graphane is Driven by London Dispersion and Enhanced Orbital Interactions," J. Chem. Theo. Comput., 11, 2015, pp. 1621-1630.

Charles T. Campbell, "Micro- and Macro-kinetics: Their Relationship in Heterogeneous Catalysis," Topics in Catalysis 1994, pp. 353-366.

Charles T. Campbell, "The Degree of Rate Control: A Powerful Tool for Catalysis Research," ACS Catalysis, 7, 2017, pp. 2770-2779.

Chengteh Lee, et al., "Development of the Colle-Salvetti Correlation-Energy Formula into a Functional of the Electron Density," Physical Review, vol. 37, No. 2, 1988, pp. 785-789.

Christian Klemps, et al., "PCNCP Ligands in the Chromium-Catalyzed Oligomerization of Ethylene: Tri- versus Tetramerization," Chem. Eur. J., 15, 2009, pp. 8259-8268.

Christophe Allemann, et al., "Theory of Asymmetric Organocatalysis of Aldol and Relate558-569d Reactions: Rationalizations and Predictions," Acc. Chem. Res., vol. 37, No. 8, 2004, pp.

Christopher Dobbin, "An Industrial Chronology of Polyethylene," NOVA Chemicals Corporation, In the Handbook of Industrial Polyethylene Technology, Scirvener Publishing, 2018, pp. 3-24.

(56) References Cited

OTHER PUBLICATIONS

Christopher N. Rowley, et al., "Computational Design of Ruthenium Hydride Olefin-Hydrogenation Catalysts Containing Hemilabile Ligands1,2," Can. J. chem. 87, 2009, pp. 1030-1038.

Chun-Yi Lin, et al., "Dispersion Force Stabilized Two-Coordinate Transition Metal-Amido Complexes of the -N(SiMe3) Dipp (Dipp+ C6H3-2,6-Pri2) Ligand: Structural, Spectroscopic, Magnetic, and Computational Studies," Inorganic Chemistry, 52, 2013, pp. 13584-13593.

Claire L. McMullin, et al., "Accurate Modelling of Pd(0) + PhX Oxidative Addition Kinetics," Dalton Transactions, 39, 2010, pp. 10833-10836.

Claire L. McMullin, et al., "Computed Ligand Effects On the Oxidative Addition of Phenyl Halides to Phosphine Supported Palladium(0) Catalysts," Dalton Transactions, 43, 2014, pp. 13545-13556.

Claire N. Temple, et al., "New Insight Into the Role of the Metal Oxidation State in Controlling the Selectivity of the Cr-(SNS) Ethylene Trimerization Catalyst," Organometallics, vol. 26, No. 18, 2007, pp. 4598-4603.

Connor W. Coley, et al., "A Graph-Convolutional Neural Network Model for the Prediction of Chemical REactivity," Royal Society of Chemistry, Chemical Science, 10, 2019, pp. 370-377.

Connor W. Coley, et al., "Machine Learning in Computer-Aided Synthesis Planning," Acc. Chem. res., 51, 2018, pp. 1281-1289.

Connor W. Coley, et al., "Prediction of Organic Reaction Outcomes Using Machine Learning," ACS Central Science, 3, 2017, pp. 434-443.

Daniel Ess, et al., "Introduction: Computational Design of Catalysts form Molecules to Materials," ACS Publications, Chem. Rev., 119, 2019, pp. 6507-6508.

Daniel M. Walden, et al., "Computational Insights Into the Central Role of Nonbonding Interactions in Modern Covalent Organocatalysis," Accounts of Chemical Research, 49, 2016, pp. 1279-1291.

Jon Paul Janet, et al., "Predicting Electronic Structure Properties of Transition Metal Complexes with Neural Networks," Chem. Sci. 8, 2017, pp. 5137-5152.

Jon Paul Janet, et al., "Resolving Transition Metal Chemical Space: Feature Selectin for Machine Learning and Structure-Property Relationships," J. Phys. Chem. A, 121, 2017, pp. 8939-8954.

Mikko M. Hanninen, et al., "A Three-Coordinate Iron-Silylene Complex Stabilized by Ligand-Ligand Dispersion Forces," Dalton Trans., 45, 2016, pp. 11301-11305.

Minglan Gong, et al., "Selective Co-Oligomerization of Ethylene and 1-Hexene by Chromium-PNP Catalysts: A DFT Study," Organometallics, 35, 2016, pp. 972-981.

Mu-Hyun Baik, et al., "Computationally Designed and Experimentally Confirmed Diastereoselective Rhodium- Catalyzed Pauson-Khand Reaction at Room Temperature," Journal of the American Chemical Society, 133, 2011, pp. 7621-7623.

Natalie Fey, et al., "Building Ligand Knowledge Bases for Organometallic Chemistry: Computational Description of Phosphorus(III)-donor Ligands and the Metal-Phosphorus Bond," Coordination Chemistry Reviews, 253, 2009, pp. 704-722.

Natalie Fey, et al., "Computational Descriptors for Chelating P,P- and P,N-Donor Ligands," Organometallics, vol. 27, No. 7, 2008, pp. 1372-1383.

Natalie Fey, et al., "Development of a Ligand Knowledge Base, Part 1: Computational Descriptors for Phosphorus Donor Ligands," Full Paper, Chem. Eur. J., 12, 2006, pp. 291-302.

Natalie Fey, et al., "Stable Fluorophosphines: Predicted and Realized Ligands for Catalysis," Angewandte Communications Int. Ed., 51, 2012, pp. 118-122.

Nathanael A. Hirscher, et al., "Isotopic Labelling in Ethylene Oligomerization: Addressing the Issue of 1-Octene vs. 1-Hexene Selectivity," Dalton Trans., 48, 2019, pp. 40-44.

Nic Friederichs, et al., "A Combined Experimental-Molecular Modeling Approach for Ethene-Propene Copolymerization With C2-Symmetric Metallocenes," Journal of Molecular Catalysis A: Chemical, 242, 2005, pp. 91-104.

Nicolas Sieffert, et al., "Noncovalent Interactions in a Transition-Metal Triphenylphosphine Complex: a Density Functional Case Study," Inorg. Chem., vol. 48, No. 11, 2009, pp. 4622-4624.

Orson L. Sydora, "Selective Ethylene Oligomerization," Organometallics, 38, 2019, pp. 997-1010.

Orson L. Sydora, et al., "Selective Ethylene Tri-/Tetramerization Catalysts," ACS Catalysis, 2, 2012, pp. 2452-2455.

P. Jeffrey Hay, et al., "Ab Initio Effective Core Potentials for Molecular Calculations. Potentials for the Transition Metal Atoms Sc to Hg," J. Chem. Phys. 82, 1, 1985, pp. 270-283.

Patrick J. Donoghue, et al., "Prediction of Enantioselectivity in Rhodium Catalyzed Hydrogenations," JACS Communications, 131, 2009, pp. 410-4110.

Patrick J.W. Deckers, et al., "Catalytic Trimerization of Ethene with Highly Active Cyclopentadienyl-Arene Titanium Catalysts," Organometallics, vol. 21, No. 23, 2002, pp. 5122-5135.

Paul A. Horn, et al., "Probing Non-Covalent Interactions with a Second Generation Energy Decomposition Analysis Using Absolutely Localized Molecular Orbitals," Phys. Chem. Chem. Phys., 18, 2016, pp. 23067-23079.

Pauli Virtanen, et al., "SciPy 1.0: Fundamental Algorithms for Scientific Computing in Python," Nature Methods, Perspective, vol. 17, Mar. 2020, pp. 261-272.

Peter A. Kollman, "Noncovalent Interactions," Acc. Chem. Res., vol. 10, 1977, pp. 365-371.

Peter H.M. Budzelaar, "Ethene Trimerizatio at CrI/CrIII—A Density Functional Theory (DFT) Study," NRC Research Press, Can. J. Chem., 87, 2009, pp. 832-837.

Peter Margl, et al., "A Unified View of Ethylene Polymerization by d0 and d0fn Transition Metals. 1. Precursor Compounds and Olefin Uptake Energetics," Organometallics, vol. 17, No. 5, 1998, pp. 933-946.

Peter Margl, et al., "General Aspects of Ethylene Polymerization by DO and D0fn Transition Metals," Top. Catal. vol. 7, 1999, pp. 187-208.

Peter R. Schreiner, et al., "Overcoming Lability of Extremely Long Alkane Carbon-Carbon Bonds Through Dispersion Forces," Nature, vol. 477, Sep. 15, 2011, pp. 308-312.

Petra Rönnholm, et al., "Aggregation and Solvation of Chiral N,P-Amide Ligands in Coordinating Solvents: A Computational and NMR Spectroscopic Study," ChemPlusChem, 77, 2012, pp. 799-806.

Pierre-Alain Breuil, et al., "Role of Homogeneous Catalysis in Oligomerization of Olefins: Focus on Selected Examples Based on Group 4 to Group 10 Transition Metal Complexes," Catalysis Letters, Springer Verlag, 145, 2015, pp. 173-192.

Piet W.N.M. van Leeuwen, et al., "New Processes for the Selective Production of 1-Octene," Coordination Chemistry Reviews, 255, 2011, pp. 1499-1517.

Qing Lu, et al., "Formation of Agostic Structures Driven by London Dispersion," Angewandte Chemie Inst. Ed., Communications, 57, 2018, pp. 4760-4764.

Qing Lu, et al., "London Dispersion Effects in the Coordination and Activation of Alkanes in σ-Complexes: a Local Energy Decomposition Study," Phys. Chem. Chem. Phys., vol. 21, No. 22, 2019, pp. 11493-12046.

Quynh Nhu N. Nguyen, et al., "The Many Roles of Quantum Chemical Predictions in Synthetic Organic Chemistry," ACES, Chemistry, An Asian Journal, 9, 2014, pp. 674-680.

R.M. Manyik, et al., "A Soluble Chromium-Based Catalyst for Ethylene Trimerization and Polymerization," J. of Cat., 47, 1977, pp. 197-209.

Raffael Huber, et al., "P-Stereogenic PN(H)P Iron(II) Catalysts for the Asymmetric Hydrogenation of Ketones: The Importance of Non-Covalent Interactions in Rational Ligand Design by Computation," Advanced Synthesis & Catalysis, 360, 2018, pp. 2900-2913.

Raghavan B. Sunoj, "Proline-Derived Organocatalysis and Synergism Between Theory and Experiments," Wires Computational Molecular Science, vol. 1, Nov. Dec. 2011, pp. 920-931.

Rainer Emrich, et al., "The Role of Metallacycles in the Chromium-Catalyzed Trimerization of Ethylene," American Chemical Society, Organometallics, vol. 16, No. 8, 1997, pp. 1511-1513.

(56) References Cited

OTHER PUBLICATIONS

Regina Palkovits, et al., "Using Artificial Intelligence to Forecast Water Oxidation Catalysts," ACS Catal., 9, 2019, 8383-8387.
Rieko Furuyama, et al., "Ethylene/Higher α-Olefin Copolymerization Behavior of Fluorinated Bis(phenoxy-imine) titanium Complexes with Methylalumoxane: Synthesis of New Polyethylene-Based Block Copolymers," Macromolecules, vol. 38, No. 5, 2005, pp. 1546-1552.
Rieko Furuyama, et al., "Fluorinated bis(phenoxy-imine) Ti Complexes with MAO: Remarkable Catalysts for Living Ethylene and Syndioselective Living Propylene Polymerization," Journal of Organometallic Chemistry 690, 2005, pp. 4398-4413.
Robert Pollice, et al., "Attenuation of London Dispersion in Dichloromethane Solutions," J. Amer. Chem. Soc., 139, 2017, pp. 13126-13140.
Robert R. Knowles, et al., "Attractive Noncovalent Interactions in Asymmetric Catalysis: Links Between Enzymes and Small Molecule Catalysts," PNAS, vol. 107, No. 48, 2010, pp. 20678-20685.
Robert Robinson, Jr., et al., "The Mechanism of Ethylene Dimerization with the Ti(OR')4/AlR3 Catalytic System: DFT Studies Comparing Metallacycle and Cossee Proposals," ACS Catalysis, 3, 2013, pp. 3006-3015.
Roberto Fiammengo, et al., "Noncovalent Secondary Interactions in Co(II)Salen Complexes: O2 Binding and Catalytic Activity in Cyclohexene Oxygenation," J. Org. Chem., 67, 2002, pp. 8552-8557.
Rumpa Pal, et al., "Linear MgCp*2 vs Bent CaCp*2: London Dispersion, Ligand-Induced Charge Localizations, and Pseudo-Pregostic C—H Ca Interactions," Inorg. Chem., 57, 2018, pp. 4906-4920.
Ryosuke Jinnouchi, et al., "Predicting Catalytic Activity of Nanoparticles by a DFT-Aided Machine-Learning Algorithm," Phys. Chem. Letters, 8, 2017, pp. 4279-4283.
Santanu Malakar, et al., "A Quantification Scheme for Non-Covalent Interactions in the Enantio-Controlling Transition States in Asymmetric Catalysis," Org. Biomol. Chem., 16, 2018, pp. 5643-5652.
Saúl H. Martinez, et al., "Importance of Dispersion on the Stability of the Concave-Bound CpM (M=Fe, Ru, Os) Complexes of Sumanene," Organometallics, 36, 2017, pp. 2036-2041.
Sayan Banerjee, et al., "Machine Learning for Predicting Product Distributions in Catalytic Regioselective Reactions," Royal Society of Chemistry, Phys. Chem. Chem. Phys., 20, 2018, pp. 18311-18313.
Sebastian Kozuch, et al., "How to Conceptualize Catalytic Cycles? The Energetic Span Model," Acc. Chem. Res., vol. 14, No. 2, 2011, pp. 101-110.
Seihwan Ahn, et al., "Design and Optimization of Catalysts Based on Mechanistic Insights Derived from Quantum Chemical Reaction Modeling," Chemical Reviews, 2019, 119, pp. 6509-6560.
Seoin Back, et al., "Toward a Design of Active Oxygen Evolution Catalysts: Insights from Automated Density Functional Theory Calculations and Machine Learning," ACS Catalysis, 9, 2019, pp. 7651-7659.
Sharon Hammes-Schiffer, "Catalysts by Design: The Power of Theory," Accounts of Chemical Research, 50, 2017, pp. 561-566.
Siyang Tang, et al., "2D-QSPR/DFT Studies of Aryl-Substituted PNP-Cr-Based Catalyst Systems for Highly Selective Ethylene Oligomerization," Springer, J. Mol. Model, 20:2129, 2014, 13 pages.
Sören Rosel, et al., "London Dispersion Enables the Shortest Intermolecular Hydrocarbon H . . . H Contact," J. Amer. Chem. Soc., 139, 2017, pp. 7428-7431.
International Search Report and Written Opinion issued in related application No. PCT/US2021/036610 dated Sep. 6, 2021, 22 pp.
Riffat Parveen, et al., "DFT and QSAR Studies of Ethylene Polymerization by Zirconocene Catalysts," ACS Catalysis, vol. 9, No. 10, Sep. 4, 2019, pp. 9339-9349.
Steven M. Maley, et al., "Quantum-Mechanical Transition-State Model Combined With Machine Learning Provides Catalyst Design Features for Selective Cr Olefin Oligomerization," ChemRxiv, Cambridge Open Engage, Jul. 27, 2020, 24 pp.
Stefan Grimme, "Comment on: "On the Accuracy of DFT Methods in Reproducing Ligand Substitution Energies for Transition Metal Complexes in Solution: The Role of Dispersive Interactions" by H. Jacobsen and L. Cavallo," ChemPhysChem, 13, 2012, pp. 1407-1409.
Stefan Grimme, "Density Functional Theory with London Dispersion Corrections," Wiley Interdiscip. Rev. Comput. Mol. Sci. vol. 1, No. 2, 20114, pp. 211-228, 2011.
Stefan Grimme, et al., "Dispersion-Corrected Mean-Field Electronic Structure Methods," Chemical Reviews, 116, 2016, pp. 5105-5154.
Stefan Grimme, et al., "On the Importance of the Dispersion Energy for the Thermodynamic Stability of Molecules," ChemPhysChem, 12, 2011, pp. 1258-1261.
Stefan Grimme, et al., "Steric Crowding Can Stabilize a Labile Molecule: Solving the Hexaphenylethane Riddle," Angewandte Chemie Int. Ed., 50, 2011, pp. 12639-12642.
Stefan Grimme, et al., "The Crucial Role of Dispersion in the Coheasion of Nonbridged Binuclear Os—Cr and Os—W Adducts," Inorganic Chemistry, vol. 49, No. 6, 2010, pp. 2911-2919.
Stephan Peitz, et al., "Heterobimetallic Al—Cl—Cr Intermediates with Relevance to the Selective Catalytic Ethene Trimerization Systems Consisting of CrCl3(THF)3, the Aminophosphorus Ligands Ph2PN(R)P(Ph)N(R)H, and Triethylaluminum," Organometallics, 30, 2011, pp. 2364-2370.
Steven C.F. Kui, et al., "Observation of Intramolecular C—H F—C Contacts in Non-Metallocene Polyolefin Catalysts: Model for Weak Attractive Interactions Between Polymer Chain and Noninnocent Ligand," Angew. Chem. Int. Ed., 42, 2003, pp. 1628-1632.
Steven E. Wheeler, et al., "Noncovalent Interactions in Organocatalysis and the Prospect of Computational Catalyst Design," Accounts of Chemical Research, 49, 2016, pp. 1061-1069.
Stuart A. Bartlett, et al., "Activation of [CrCl3(R-SN(H)S-R}] Catalysts for Selective Trimerization of Ethene: A Freeze-Quench Cr K-Edge XAFS Study," ACS Catalysis, 4, 2014, pp. 4201-4204.
Sumit Bhaduri, et al., "Density Functional Studies on Chromium Catalyzed Ethylene Trimerization," Journal of Organometallic Chemistry, 694, 2009, pp. 1297-1307.
Sung-Kwan Kim, et al., "Bimetallic Ethylene Tetramerization Catalysts Derived from Chiral DPPDME Ligands: Sytheses, Structural Characterizations, and Catalytic Performance of [(DPPDME)CrCl3]2 (DPPDME=S,S- and R, R-chiraphos and meso-achiraphos)," Organometallics, vol. 29, No. 22, 2010, pp. 5805-5811.
Susumu Mitsumori, et al., "Direct Asymmetric Anti-Mannich-Type Reactions by a Designed Amino Acid," J. Am. Chem. Soc., 128, 2006, pp. 1040-1041.
Sven Tobisch, et al., "Catalytic Linear Oligomerization of Ethylene to Higher α-Olefins: Insight into the Origin of the Selective Generation of 1-Hexene Promoted by a Cationic Cyclopentadienyl-Arene Titanium Active Catalyst," Organometallics, vol. 22, No. 26, 2003, pp. 5392-5405.
Sven Tobisch, et al., "Catalytic Oligomerization of the Ethylene to Higher Linear α-Olefins Promoted by the Cationic Group 4 [η5-Cp-(CMe2-bridge)-Ph)M11(ethylene)2]+ (M=Ti, Zr, Hf) Active Catalysts: A Density Functional Investigation of the Influence of the Metal on the Catalytic Activity and Selectivity," J. Am. Chem. Soc., 126, 2004, pp. 9059-9071.
T. Agapie, "Selective Ethylene Oligomerization: Recent Advances in Chromium Catalysis and Mechanistic Investigations," Coord. Chem. Rev., 255, 2011, 861-880.
T. Agapie, et al., "Mechanistic Studies of Olefin and Alkyne Trimerization With Chromium Catalysts: Deuterium Labeling and Studies of Regiochemistry Using a Model Chromacyclopentane Complex," J. Am. Chem. Soc., 129, 2007, 14281-14295.
T. Agapie, et al., "Mechanistic Studies of the Ethylene Trimerization Reaction With Chromium-Diphosphine Catalysts: Experimental Evidence for a Mechanism Involving Metallacyclic Intermediates," J. Am. Chem. Soc. 126, 2004, 1304-1305.
Tamara Husch, et al., "Calculation of Ligand Dissociation Energies in Large Transition-Metal Complexes," J. Chem. Theor. and Comp., 14, 2018, pp. 2456-2468.

(56) References Cited

OTHER PUBLICATIONS

Theodorus J.M. de Bruin, et al., "Hemilabile Ligand Induced Selectivity: a DFT Study on Ethylene Trimerization Catalyzed by Titanium Complexes," Organometallics, vol. 22, No. 17, 2003, pp. 3404-3413.
Theresa Sperger, et al., "Computation and Experiment: A Powerful Combination to Understand and Predict Reactivities," Accounts of Chemical Research, 49, 2016, pp. 1311-1319.
Thilina Gunasekara, et al., "Mechanistic Insights into Chromium-Catalyzed Ethylene Trimerization," ACS Catalysis, 8, 2018, pp. 6810-6819.
Thomas Weymuth, "New Benchmark Set of Transition-Metal Coordination Reactions for the Assessment of Density Functionals," J. Chem. Theo. Compu., 10, 2014, pp. 3092-3103.
Tian Lu, et al., "A Multifunctional Wavefunction Analyzer," J. of Computational Chemistry, Software News and Updates, 33, 2012, pp. 580-592.
Travis E. Oliphant, "Guide to NumPy," Trelgol Publishing: USA, Dec. 7, 2006, 379 pages.
Varinia Bernales, et al., "Computationally Guided Discovery of a Catalytic Cobalt-Decorated Metal-Organic Framework for Ethylene Dimerization," The Journal of Physical Chemistry, 120, 2016, pp. 23576-23583.
Wenbo Sun, et al., "The Use of Deep Learning to Fast Evaluate Organic Photovoltaic Materials," Advanced Theory and Simulations, 2, 2019, 1800116, 9 pages.
Werner Janse van Rensburg, "A DFT Study Toward the Mechanism of Chromium-Catalyzed Ethylene Trimerization," Organometallics, vol. 23, No. 6, 2004, pp. 1207-1222.
Werner Janse van Rensburg, et al., "Role of MAO in Chromium-Catalyzed Ethylene Tri- and Tetramerization: A DFT Study," Organometallics, vol. 26, No. 4, 2007, pp. 1000-1013.
Wes McKinney, "Data Structures for Statistical Computing in Python," Proc. of the 9th Python in Science Conf. (SCIPY 2010), pp. 56-61.
Wesley H. Monillas, et al., "A Well-Defined Model System for the Chromium-Catalyzed Selective Oligomerization of Ethylene," Dalton Transactions, 42, 2013, pp. 9198-9210.
William Humphrey, et al., "VMD: Visual Molecular Dynamics," J. Molecular Graphics, vol. 14, 1996, pp. 33-38.
Xiangyu Guo, et al., "Simultaneously Achieving High Activity and Selectivity Toward Two-Electron O2 Electroreduction: The Power of Single-Atom Catalysts," ACS Catalysis, 9, 2019, pp. 11042-11054.
Xiaorong Zhu, et al., "Activity Origin and Design Principles for Oxygen Reduction on Dual-Metal-Site Catalysts: A Combined Density Functional Theory and Machine Learning Study," J. Phys. Chem. Lett., 10, 2009, pp. 7760-7766.
Xiaoxia Han, et al., "Comparison of Machine Learning Algorithms in Screening Potential Additives to Ni/Al2O3 Methanation Catalysts for Improving the Anti-Coking Performance," ChemPubSoc. Europe, Chemistry Select, 4, 2019, pp. 11790-11795.
Xuhui Lin, et al., "A Theoretical Perspective of the Agostic Effect in Early Transition Metal Compounds," Coordination Chem. Rev., 419, 2020, 1-18, 18 pages.
Yan Zhao, et al., "Attractive Noncovalent Interactions in the Mechanism of Grubbs Second-Generation Ru Catalysts for Olefin Metathesis," Am. Chem. Soc., Organic Letters, vol. 9, No. 10, 2007, pp. 1967-1970.
Yan Zhao, et al., "The M06 Suite of Density Functionals for Main Group Thermochemistry, Thermochemical Kinetics, Noncovalent Interactions, Excited States, And Transition Elements: Two New Functionals and Systematic Testing of Four M06-Class Functionals and 12 Other Functionals," Theor. Chem. Account, 120, 2008, pp. 215-241.
Yernaidu Reddi, et al., "Harnessing Noncovalent Interactions in Dual-Catalytic Enantioselective Heck-Matsuda Arylation," J. Am. Chem. Soc., 141, 2019, pp. 998-1009.

Yihan Shao, et al., "Advances in Molecular Quantum Chemistry Contained in the Q-Chem 4 Program Package," Molecular Physics, vol. 113, No. 2, pp. 184-215, 2014.
Yuan Qi, et al., "Role of 1,2-Dimethoxyethane in the Transformation from Ethylene Polymerization to Trimerization Using Chromium Tris(2-ethylhexanoate)-Based Catalyst System: A DFT Study," Organometallics, 29, 2010, pp. 1588-1602.
Yuanyuan Wang, et al., "A Computationally Designed Rh(I)-Catalyzed Two-Component [5+2+!] Cycloaddition of Ene-vinylcyclopropanes and CO for the Synthesis of Cyclooctenones," J. Am. Chem. Soc., vol. 129, No. 33, 2007, pp. 10060-10061.
Yun Yang, et al., "Mechanistic DFT Study on Ethylene Trimerization of Chromium Catalysts Supported by a Versatile Pyrrole Ligand System," Organometallics, 33, 2014, pp. 2599-2607.
Yun Yang, et al., "Selective Ethylene Tri-/Tetramerization by in Situ-Formed Chromium Catalysts Stabilized by N,P-Based Ancillary Ligand Systems," ACS Catalysis, 3, 2013, pp. 2353-2361.
Yun Yang, et al., "Spin Surface Crossing Between Chromium(I)/Sextet and Chromium(III)/Quartet Without Deprotonation in SNS—Cr Mediated Ethylene Trimerization," Organometallics, 30, 2011, pp. 5297-5302.
Yury Minenkov, et al., "The Accuracy of DFT-Optimized Geometries of Functional Transition Metal Compounds: a Validation Study of Catalysts for Olefin Metathesis and Other Reactions in the Homogeneous Phase," Dalton Transactions, 41, 2012, pp. 5526-5541.
Yury Minenkov, et al., "The Nature of the Barrier to Phosphane Dissociation from Grubbs Olefin Metathesis Catalysts," Eur. J. Inorg. Chem., 2012, pp. 1507-1516.
Zachary W. Ulissi, et al., "Machine-Learning Methods Enable Exhaustive Search for Active Bimetallic Facets and Reveal Active Site Motifs for CO2 Reduction," ACS Catalysis, 7, 2017, pp. 6600-6608.
Zheng Li, et al., "Feature Engineering of Machine-Learning Chemisorption Models for Catalyst Design," Catalysis Today, 280, 2017, pp. 232-238.
Zhi-Xiang Yu, et al., "Why Trimerization? Computational Elucidation of the Origin of Selective Trimerization of Ethene Catalyzed by [TaCl3(CH3)2] and an Agostic-Assisted Hydride Transfer Mechanism," Angew. Chem. Int. Ed., Communications, vol. 42, No. 7, 2003, pp. 808-811.
Jesús Jover, et al., "The Computational Road to Better Catalysts," Chem. An Asian Journal, 9, 2014, pp. 1714-1723.
Joao Aires-de-Sousa, et al., "Prediction of Enantiomeric Excess in a Combinatorial Library of Catalytic Enantioselective Reactions," J. Comb. Chem., vol. 7, No. 2, 2005, pp. 298-301.
John T. Dixon, et al., "Advances in Selective Ethylene Trimerisation—a Critical Overview," Journal of Organometallic Chemistry, 689, 2004, pp. 3641-3668.
Jolene P. Reid, et al., "Comparing Quantitative Prediction Methods for the Discovery of Small-Molecule Chiral Catalysts," Nature Reviews, vol. 2, Oct. 2018, pp. 290-305.
Jorge Echeverría, et al., "Dihydrogen Contacts in Alkanes Are Subtle But Not Faint," Nature Chemistry, vol. 3, 2011, pp. 323-330.
Joseph T. Golab, "Making Industrial Decisions with Computational Chemistry," Enabling Science, ChemTech, 1998, pp. 17-23.
Jun Zhang, et al., "Highly Selective Chromium(III) Ethylene Trimerization Catalysts With [NON] and [NSN] Heteroscorpionate Ligands," Organometallics, vol. 27, No. 17, 2008, pp. 4277-4279.
Jungwun Hwang, et al., "Distance-Dependent Attractive and Repulsive Interactions of Bulky Alkyl Groups," Angewandte Chemie Int. Ed., Communications55, 2016, pp. 8086-8089.
Junya Ohyama, et al., "Data Driven Determination of Reaction Conditions in Oxidative Coupling of Methane Via Machine Learning," ChemPubSoc Europe, ChemCatChem, 11, 2019, pp. 4307-4313.
K. Weissermel, et al., Chapter 3 of Industrial Organic Chemistry, 5th Ed., "Olefins," Wiley-VCH Verlag Gmbh & Co., 2010, pp. 59-89.
K.E. Abdelfatah, et al., "Prediction of Transition-State Energies of Hydrodeoxygenation Reactions on Transition-Metal Surfaces Based on Machine Learning," J. Phys. Chem., C 2019, 123, 29804-29810.

(56) References Cited

OTHER PUBLICATIONS

K.N. Houk, et al., "Computational Prediction of Small-Molecule Catalysts," Commentary Insight, Nature, vol. 455, 2008, pp. 309-313.

Kamran T. Mahmudov, et al., "Noncovalent Interactions in Metal Complex Catalysis," Coordination Chem. Rev., 387, 2019, pp. 32-46.

Keisuke Takahashi, et al., "Rapid Estimation of Activation Energy in Heterogeneous Catalytic Reactions Via Machine Learning," J. Comp. Chem., 39, 2018, pp. 2405-2408.

Keisuke Takahashi, et al., "Unveiling Hidden Catalysts for the Oxidative Coupling of Methane Based on Combining Machine Learning With Literature Data,"ChemPubSoc Europe, ChemCatChem, 10, 2018, pp. 3223-3228.

Kerstin Freitag, et al., "Dizinc Cation [Zn2]2+ Trapped in a Homoleptic Metalloid Coordination Environment Stabilized by Dispersion Forces: [Zn2(GaCp*)6][BAr4F]2," ACS Publications, Inorganic Chemistry, 54, 2015, pp. 352-358.

Kirill A. Alferov, et al., "Chromium Catalysts for Selective Ethylene Oligomerization to 1-Hexene and 1-Octene: Recent Results," Applied Catalysis A, General 542, 2017, pp. 71-124.

Klaus Müller-Dethlefs, et al., "Noncovalent Interactions: A Challenge for Experiment and Theory," Chem. Rev., vol. 100, No. 1, 2000, pp. 143-167.

Konstantin P. Bryliakov, et al., "Noncovalent Interactions in o-Fluorinated Popst-titanocene Living Ethylene Polymerization Catalyst," Organometallics, vol. 29, No. 20, 2010, pp. 4428-4430.

Lando P. Wolters, et al., "Role of Steric Attraction and Bite-Angle Flexibility in Metal-Mediated C—H Bond Activation," ACS Catalysis, 5, 2015, pp. 5766-5775.

Laura E. Fernandez, et al., "Theoretical Design of Molecular Electrocatalysts With Flexible Pendant Amines for Hydrogen Production and Oxidation," The Journal of Physical Chemistry, Letters, 4, 2013, pp. 542-546.

Laura Falivene, et al., "Towards the Online Computer-Aided Design of Catalytic Pockets," Nature Chemistry, Perspective, vol. 11, 2019, pp. 872-879.

Le Zhang, et al., "Chromium-Based Ethylene Tetramerization Catalysts Supported by Silicon-Bridged Diphosphine Ligands: Further Combination of High Activity and Selectivity," ChemPubSoc Europe, ChemCatChem Communications, 9, 2017, pp. 76-79.

Lijuan Song, et al., "Role of London Dispersion Interactions in Ga-Substituted Dipnictenes," Am. Chem. Soc., Organometallics, 38, 2019, pp. 1640-1647.

Lixu Yang, et al., "How Much Do Van Der Waals Dispersion Forces Contribute to Molecular Recognition in Solution?," Nature Chemistry, vol. 5, Dec. 2013, pp. 1006-1010.

Lucy E. Bowen, et al., "One Electron Oxidation of Chromium N,N-bis(diarylphosphino)amine and bis(diarylphosphino) methane Complexes Relevant to Ethene Trimerisation and Tetramerisation," Dalton Transactions, The Royal Society of Chemistry, 2007, pp. 1160-1168.

M.J. Frisch, et al. Gaussian 09, revision D. 01. Gaussian, Inc., Wallingford, CT 2015, 20 pages.

M.J. Frisch, et al. Gaussian 16, Rev. A.01. Gaussian Inc.: Wallingford, CT 2016, 14 pages.

M.S.G. Ahlquist, et al., "Dispersion and Back-Donation Gives Tetracoordinate [Pd(PPh3)4]," Agnew. Chem. Int. Ed. , 60, 2011, 11794-11797.

Madison L. McCrea-Hendrick, et al., "Counterintuitive Interligand Angles in the Diaryls E{C6H3-2,6-(C6H2-2,4,6-iPr3)2] 2 (E=Ge, Sn, or Pb) and Related Species: The Role of London Dispersion Forces," Organometallics, 37, 2018, pp. 2075-2085.

Mads C. Nielsen, et al., "Computational Ligand Design for the Reductive Elimination of ArCF3 from a Small Bite Angle PdII Complex: Remarkable Effect of a Perfluoroalkyl Phosphine," Angewandte Chemie Int. Ed., 53, 2014, pp. 5903-5906.

Mahboubeh Kheirabadi, et al., "Spiroligozymes for Transesterifications: Design and Relationship of Structure to Activity," J. Am. Chem. Soc., 134, 2012, pp. 18345-18353.

Makoto Mitani, et al., "Living Polymerization of Ethylene Catalyzed by Titanium Complexes Having Fluorine-Containing Phenoxy-Imine Chelate Ligands," J. Am. Chem. Soc., 124, 2002, pp. 3327-3336.

Makoto Mitani, et al., "Unprecedented Living Olefin Polymerization Derived from an Attractive Interaction Between a Ligand and a Growing Polymer Chain," Chem. Eur. J., 9, 2003, pp. 2396-2403.

Manoj Kumar, et al., "Ligand Effects on the Regioselectivity of Rhodium-Catalyzed Hydroformylation: Density Functional Calculations Illuminate the Role of Long-Range Noncovalent Interactions," Organometallics, 33, 2014, pp. 4183-4191.

Marcel A. Strauss, et al., "Molecular Systems for the Quantification of London Dispersion Interactions," ChemPubSoc Europe, Europe J. Org. Chem., 2019, pp. 295-302.

Marisa C. Kozlowski, et al., "Quantum Mechanical Models Correlating Structure with Selectivity: Predicting the Enantioselectivity of β-Amino Alcohol Catalysts in Aldehyde Alkylation," J. Am. Chem. Soc., 125, 2003, pp. 6614-6615.

Markus Brusch, et al., "Understanding and Quantifying London Dispersion Effects in Organometallic Complexes," Acc. Chem. Res., 52, 2019, pp. 258-266.

Markus Reiher, et al., "Reparameterization of Hybrid Functionals Based on energy Differences of States of Different Multiplicity," Theor. Chem. Acc., 107, 2001, pp. 48-55.

Martin E. Bluhm, et al., "Chromium Imine and Amine Complexes as Homogeneous Catalysts for the Trimerisation and Polymerisation of Ethylene," Science Direct, Journal of Organometallic Chemistry, 690, 2005, pp. 713-721.

Masashi Yamakawa, et al., "CH/π Attraction: The Origin of Enantioselectivity in Transfer Hydrogenation of Aromatic Carbonyl Compounds Catalyzed by Chiral H6-Arene-Ruthenium(II) Complexes," Angew. Chem. Int. Ed., vol. 40, No. 15, 2001, pp. 2818-2821.

Mati Karelson, et al., "Quantum-Chemical Descriptors in QSAR/QSPR Studies," Chem. Rev., vol. 96, No. 3, 1996, pp. 1027-1043.

Matthew A. Kayala, et al., "Learning to Predict Chemical Reactions," Am. Chem. Soc., J. Chem. Info. & Modeling, 51, 2011, pp. 2209-2222.

Matthew K. Nielsen, et al., "Deoxyfluorination With Sulfonyl Fluorides: Navigating Reaction Space With Machine earning," J. Am. Chem. Soc., 140, 2018, pp. 5004-5008.

Matthew S. Sigman, et al., "The Development of Multidimensional Analysis Tools for Asymmetric Catalysis and Beyond," Accounts of Chemical Research, Amer. Chem. Soc., 49, 2016, pp. 1292-1301.

Maurizio Galimberti, et al., "Ethene/Propene Copolymerization With High Product of Reactivity Ratios from a Single Center, Metallocene-Based Catalytic System," Macromolecules, vol. 31, No. 11, 1998, pp. 3409-3416.

Maurizio Galimerti, et al., "Metallocenes for Ethene/Propene Copolymerization with High Product of Reactivity Ratios," Macromolecules, vol. 32, No. 24, 1999, pp. 7968-7976.

Md. Anwar Hossain, et al., "Spin-Crossover in Chromium-Catalyzed Ethylene Trimerization: Density Functional Theory Study," Bull. Korean Chem. Soc., vol. 35, No. 9, 2014, pp. 2835-2838.

Michael C.W. Chan, "Weak Attractive Ligand-Polymer and Related Interactions in Catalysis and Reactivity: Impact, Applications, and Modeling," Focus Reviews, Wiley InterScience, Chem. Asian J., 3, 2008, pp. 18-27.

Michael C.W. Chan, et al., "Neutron and X-Ray Diffraction and Spectroscopic Investigations of Intramolecular [C—H F—C] Contacts in Post-Metallocene Polyolefin Catalysts: Modeling Weak Attractive Polymer-Ligand Interactions," Full Paper, Chem. Eur. J. 12, 2006, pp. 2607-2619.

David Danovich, et al., "Understanding the Nature of the CH HC Interactions in Alkanes," Jour. Chem. Theory and Comp., 9, 2013, pp. 1977-1991.

David J. Liptrot, et al., "London Dispersion Forces in Sterically Crowded Inorganic and Organometallic Molecules," Nature Reviews, Chemistry, vol. 1, Art. No. 4, 2017, 12 pages.

David S. McGuiness, et al., "Cocatalyst Influence in Selective Oligomerization: Effect on Activity, Catalyst Stability, and 1-Hexene/1-Octene Selectivity in the Ethylene Trimerization and Tetramerization Reaction," Organometallics, 26, 2007, pp. 2561-2569.

(56) References Cited

OTHER PUBLICATIONS

David S. McGuiness, et al., "Ethylene Trimerization With Mixed-Donor Ligand (N,P,S) Chromium Complexes: Effect of Ligand Structure on Activity and Selectivity," Organometallics, 24, 2005, pp. 552-556.
David S. McGuiness, et al., "First Cr(III)-SNS Complexes and Their Use as Highly Efficient Catalysts for the Trimerization of Ethylene to 1-Hexene," J. Am. Chem. Soc., 125, 2003, pp. 5272-5273.
David S. McGuinness, "Olefin Oligomerization via Metallacycles: Dimerization, Trimerization, Tetramerization, and Beyond," Chemical Reviews, 111, 2011, pp. 2321-2341.
David S. McGuinness, et al., "Ethylene Trimerisation With Cr—PNP Catalysts: A Theoretical Benchmarking Study and Assessment of Catalyst Oxidation State," Aut. J. Chem, 67, 2014, pp. 1481-1490.
David S. Palmer, et al., "Random Forest Models to Predict Aqueous Solubility," J. Chem. Inf. Model., 47, 2007, pp. 150-158.
Dean J. Tantillo, "Faster, Catalyst! React! React! Exploiting Computational Chemistry for Catalyst Development and Design," Accounts of Chemical Research, 49, 2016, p. 1079.
Dean J. Tantillo, "Using Theory and Experiment to Discover Catalysts for Electrocyclizations," Angewandte Chemie Int. Ed., 48, 2009, pp. 31-32.
Derek J. Durand, et al., "Computational Ligand Descriptors for Catalyst Design," Chem. Reviews, 119, 2019, pp. 6561-6594.
Derek T. Ahneman, et al., "Predicting Reaction Performance in C—N Cross-Coupling Using Machine Learning," Organic Chemistry, Science 360, 2018, pp. 186-190.
Diana Yepes, et al., "Unveiling the Delicate Balance of Steric and Dispersion Interactions in Organocatalysis Using High-Level Computational Methods," J. Am. Chem. Soc., 142, 2020, pp. 3613-3625.
Doo-Hyun Kwon, et al., "Computational Transition-State Design Provides Experimentally Verified Cr(P,N) Catalysts for Control of Ethylene Trimerization and Tetramerization," ACS Catalysis, 8, 2018, pp. 1138-1142.
Eirik Lyngvi, et al., "Dispersion Makes the Difference: Bisligated Transition States Found for the Oxidative Addition of Pd(PtBu3)2 to Ar—OSO2R and Dispersion-Controlled Chemoselectivity in Reactions with Pd[P(iPr)(tBu2)]2," Organometallics, 34, 2015, pp. 805-812.
Elizabeth H. Krenske, et al., "Aromatic Interactions as Control Elements in Stereoselective Organic Reactions," NIH Public Access, Acc. Chem. Res., vol. 46, No. 4, 2013, pp. 979-989.
Eric Jones, et al., "SciPy: Open Source Tools for Python," Science Open, 2001.
Erin R. Johnson, et al., "Revealing Noncovalent Interactions," J. Am. Chem. Soc. Articles, 132, 2010, pp. 6498-6506.
Eugene S. Beh, et al., "Synthesis of 5,5-Bicyclic Amidines as Ligands for Thermally Stable Vapor Deposition Precursors," Organometallics, 36, 2017, pp. 1453-1456.
F. Dean Toste, et al., "Pursuit of Noncovalent Interactions for Strategic Site-Selective Catalysis," Accounts of Chemical Research, 50, 2017, pp. 609-615.
Fabian Pedregosa, et al., "Scikit-learn: Machine Learning in Python," Journal of Machine Learning Research, 12, 2011, pp. 2825-2830.
Farhan Ahmad Pasha, et al., "DFT Study on the Impact of the Methylaluminoxane Cocatalyst in Ethylene Oligomerization Using a Titanium-Based Catalyst," Organometallics, 34, 2015, pp. 426-431.
Feliu Maseras, et al., "Opposing Steric and Electronic Contributions in OsCl2H2(PPri3)2. A Theoretical Study of an Unusual Structure." New J. Chem, 1998, pp. 5-9.
Francesco Zaccaria, et al., "Accurate Prediction of Copolymerization Statistics in Molecular Olefin Polymerization Catalysis: The Role of Entropic, Electronic, and Steric Effects in Catalyst Comonomer Affinity," ACS Catalysis, 7, 2017, pp. 1512-1519.
Frank Biedermann, et al., "Experimental Binding Energies in Supramolecular Complexes," Chemical Reviews, ACS Publications, 116, 2016, pp. 5216-5300.
Gang Lu, et al., "Ligand-Substrate Dispersion Facilitates the Copper-Catalyzed Hydroamination of Unactivated Olefins," J. Am. Chem. Soc., 139, 2017, pp. 16548-16555.
Garima Jindal, et al., "Rational Design of Catalysts for Asymmetric Diamination Reaction Using Transition State Modeling," Organic & Biomolecular Chemistry, 12, 2014, pp. 2745-2753.
Gentoku Takasao, et al., "Machine Learning-Aided Structure Determination for TiCl4-Capped MgCl2 Nanoplate of Heterogeneous Ziegler-Natta Catalyst," ACS Catalysis, 9, 2019, pp. 2599-2609.
George J.P. Britovsek, et al., "A DFT Mechanistic Study on Ethylene Tri- and Tetramerization with Cr/PNP Catalysts: Single Versus Double Insertion Pathways," Chemistry A European Journal, Chem. Pub. Soc. Europe, 22, 2016, pp. 16891-16896, Wiley Online Library.
George J.P. Britovsek, et al., "Mechanistic Study of Ethylene Tri- and Tetramerisation with Cr/PNP Catalysts: Effects of Additional Donors," Royal Society of Chemistry, Catalysis Science & Technology, 6, 2016, pp. 8234-8241.
George J.P. Britovsek, et al., "Single- and Double-Coordination Mechanism in Ethylene Tri- and Tetramerizatio with Cr/ PNP Catalysts," ACS Catalysis, 5, 2015, pp. 4152-4166.
Giovanni Talarico, et al., ""Living" Propene Polymerization with Bis(phenoxyimine) Group 4 Metal Catalysts: New Strategies and Old Concepts," Organometallics, vol. 23, No. 25, 2004, pp. 5989-5993.
Giuliano Cecchin, et al., "Ziegler-Natta Catalysts," Kirk-Othmer Encyclopedia of Chemical Technology, vol. 26, John Wiley and Sons, pp. 1-53, copyright 2007.
Grace X. Gu, et al., "De novo Composite Design Based on Machine Learning Algorithm," Extreme Mechanics Letters, 18, 2018, pp. 19-28.
Gregory A. Landrum, et al., "Machine-Learning Models for Combinational Catalyst Discovery," Inst. Phys. Publ., Meas. Sci. Tech., 16, 2005, pp. 270-277.
Hanyu Gao, et al., "Using Machine Learning to Predict Suitable Conditions for Organic Reactions," ACS Central Science, 4, 2018, pp. 1465-1476.
Hao Wang, et al., "Iridium-Catalyzed Enantioselective C(sp3)-H Amidation Controlled by Attractive Noncovalent Interactions," J. Am. Chem. Soc., 141, 2019, pp. 7194-7201.
Haruyuki Makio, et al., "Development and Application of FI Catalysts for Olefin Polymerization: Unique Catalysis and Distinctive Polymer Formation," Acc. Chem. Res., vol. 42, No. 10, 2009, pp. 1532-1544.
Heiko Jacobsen, et al., "On the Accuracy of DFT Methods in Reproducing Ligand Substitution Energies for Transition Metal Complexes in Solution: The Role of Dispersive Interactions," Chem. Phys. Chem. 13, 2012, pp. 562-569.
Heiko Jacobsen, et al., "Reply to the comment by Grimme on: 'On the Accuracy of DFT Methods in Reproducing Ligand Substitution Energies for Transition Metal Complexes in Solution: The Role of Dispersive Interactions'," Chem. Phys. Chem. 13, 2012, pp. 1405-1406.
Helmut G. Alt and Alexander Koppl, "Effect of the Nature of Metallocene Complexes of Group IV Metals on Their Performance in Catalytic Ethylene and Propylene Polymerization," Laboratorium für Anorganische Chemie, Universität Bayreuth, D-95440 Bayreuth, Germany, Chem. Rev., 2000, 100 (4), pp. 1205-1221.
Indrek Kalvet, et al., "Selective Ortho-Functionalization of Adamantylarenes Enabled by Dispersion and an Air-Stable Palladium(I) Dimer," Angewandte Chemie Int. Ed., Communications, 59, 2020, pp. 7721-7725.
IUPAC Compendium of Chemical Terminology, 2nd Ed. 1997, pp. 1-1670.
J. Paul Hogan, et al., "History of Crystalline Polypropylene. In History of Polyolefins: The World's Most Widely Used Polymers," Springer Netherlands, 1986, pp. 103-115.
J. Philipp Wagner, et al., "London Dispersion in Molecular Chemistry-Reconsidering Steric Effects," Angewandte Chem. Int. Ed., Reviews, 54, 2015, pp. 12274-12296.
James C. Ianni, et al., "A Priori Theoretical Prediction of Selectivity in Asymmetric Catalysis: Design of Chiral Catalysts by Using

(56) References Cited

OTHER PUBLICATIONS

Quantum Molecular Interaction Fields," Angew. Chemie Int. Ed., Computational Models, 45, 2006, pp. 5502-5505.

James E. Radcliffe, et al., "Phosphanyl Methanimine (PCN) Ligands for the Selective Trimerization/Tetramerization of Ethylene with Chromium," ACS Catalysis, 5, 2015, pp. 7095-7098.

Jennifer N. Wei, et al., "Neural Networks for the Prediction of Organic Chemistry Reactions," ACS Central Science, 2, 2016, pp. 725-732.

Jesús Jover, et al., "Expansion of the Ligand Knowledge Base for Chelating P,P-Donor Ligands (LKB-PP)," Organometallics, 31, 2012, pp. 5302-5306.

Jesús Jover, et al., "Expansion of the Ligand Knowledge Base for Monodentate P-Donor Ligands (LKB_P)," Organometallics, vol. 29, No. 23, 2010, pp. 6245-6258.

International Search Report and Written Opinion issued in corresponding PCT Application No. PCT/US2022/074676, dated Jan. 10, 2023, 18 pp.

Partial International Search Report and Written Opinion issued in corresponding PCT Application No. PCT/US2022/074676, dated Nov. 14, 2022, 9 pp.

E. Aitola, et al., "Polymerization of Ethene with Zirconocene Catalysts: An Experimental and Quan6um Chemical Study of the Influence of Para-substituent in Benzyl in bis(@h/\5-(1-benzyl) indenyl} Zirconium Dichlorides," Journal of Organometallic Chemistry, Elsevier, Amsterdam, NL, vol. 690, No. 3, Jan. 28, 2005, pp. 773-783; XP027709037.

M.J. Schneider, et al., "Influence of Indenyl Ligand Substitution Pattern on Metallocene-Catalyzed Ethene Copolymerization With 1-Octene," Macromolecules, American Chemical Society, vol. 30, No. 11, Jun. 2, 1997, pp. 3164-3168; XP000691133.

\* cited by examiner

Strong attraction　　　　van der Waals　　　　Strong repulsion
(H-bond, halogen bond)　　interaction Indenyl Type Catalysts Halogens F     Cl     Br Hydrocarbon Alkoxy and carbonyl Amine, Phosphine and Thiol 4-Phenyl Indenyl Catalysts

—CH$_3$     —OCH$_3$     —CF$_3$

MODULATING CO-MONOMER SELECTIVITY USING NON-COVALENT DISPERSION INTERACTIONS IN GROUP 4 OLEFIN POLYMERIZATION CATALYSTS

CROSS REFERENCE TO RELATED APPLICATIONS

None.

TECHNICAL FIELD OF THE DISCLOSURE

This disclosure relates to computational methods for developing new catalyst systems, including metallocene-based catalyst systems for the co-polymerization of ethylene and an alpha ($\alpha$)-olefin.

BACKGROUND OF THE DISCLOSURE

Polyethylene is one of the most utilitarian and economically significant commodity chemicals and is produced on a massive scale (about 100 million tons/annum). Different types of polyethylene having unique material properties and suited for sundry applications can be produced through co-polymerization of ethylene with linear $\alpha$-olefins (alpha-olefins), such as propylene, 1-butene, 1-hexene, 1-octene, and the like. Such co-polymers may constitute lower density polymers than ethylene homopolymer and exhibit improved performance properties in specific applications.

Group 4 metallocene catalysts such as zirconocene catalysts are useful for polymerizing ethylene particularly with an $\alpha$-olefin co-monomer to generate a diverse assortment of polyethylenes. Incorporation of the olefin co-monomer into the growing polyethylene chain can impart a range of favorable properties to the resulting polymer, and factors such as the choice of co-monomer and the relative rate of co-monomer versus ethylene incorporation into the growing polyethylene chain can be used to adjust the polymer properties.

As a result, methods which may provide the ability to understand and modulate co-monomer selectivity in an olefin polymerization catalyst would be useful in tailoring the desired properties of the polyethylene. Therefore, there remains a need for new methods including new computational methods for the design and development of ethylene polymerization catalysts with an improved ability to adjust or modulate co-monomer selectivity. There is also a need for new computational methods which can be experimentally verified to better design new ethylene polymerization catalysts.

SUMMARY OF THE DISCLOSURE

This disclosure provides new methods for the design and development of ethylene polymerization catalysts, including Group 4 metallocene catalysts, which are based on an improved ability to adjust or modulate co-monomer selectivity into the growing polymer chain. Previously, only repulsive steric interactions have been considered in the design of new Group 4 catalysts, particularly zirconocene catalysts, in order to control $\alpha$-olefin co-monomer incorporation during catalysis. In an aspect, it has been unexpectedly discovered through computational analysis of catalysts that stabilizing non-covalent dispersion type interactions can be used to modulate co-monomer selectivity into the polyethylene chain. Adjusting these stabilizing non-covalent dispersion type interactions can, in turn, be used to tailor the catalyst design to provide the desired co-monomer incorporation into a polyethylene.

In one aspect, conventional designs of metallocene olefin polymerization catalysts emphasized the metal center and repulsive steric influences from cyclopentadienyl (Cp)-type ligands. In this disclosure, a catalyst design based on a transition state model and computationally screened ligands is provided that can identify new catalyst candidates for modulating co-monomer incorporation. For an experimentally validated test set of ethylene/propylene co-polymerization zirconocene catalysts, it has been discovered that non-covalent dispersion stabilization provides quantitative accuracy in predicting the relative selectivity of the particular catalyst design. Further analysis of these catalysts and their relative selectivities provided the unexpected realization of the influence of dispersion stabilization in transition state models on transition state $\Delta G^\ddagger$ values and accordingly on co-monomer incorporation rates. In an aspect, this disclosure provides a method of controlling ethylene/1-hexene selectivity in Group 4 metallocene olefin polymerization catalyst, for example in zirconocene catalysts, and further provides a method for designing a Group 4 metallocene olefin polymerization catalysts.

Computational screening of metallocene catalyst frameworks led to the identification of zirconocene ligands that either inhibit or enhance co-monomer 1-hexene incorporation during ethylene polymerization. The influence of dispersion interactions in transition-metal complex catalyzed reactions has not be recognized previously, as such interactions have been largely ignored as inconsequential.

Accordingly, in an aspect, this disclosure provides a method for designing a Group 4 metallocene olefin polymerization catalyst, the method comprising: (a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework; (b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an $\alpha$-olefin co-monomer molecule into the metal-hydrocarbyl ligand bond of the first metallocene catalyst framework; (c) determining, by at least one processor of a device, the relative energies of each of the first ground state model structure ($GS^A$), the first transition state model structure ($TS^{A1}$) and a dispersion energy (Disp $E^{A1}$) associated with $TS^{A1}$, and the second transition state model structure ($TS^{A2}$) and a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A2}-GS^A$), $\Delta\Delta G^{\ddagger A}$ ($TS^{A2}-TS^{A1}$), and an absolute difference in dispersion energies $|\Delta\text{Disp } E^A|$ calculated as $|\Delta(\text{Disp } E^{A2}-\text{Disp } E^{A1})|$ for migratory insertion of the ethylene molecule versus the $\alpha$-olefin molecule in the first metallocene catalyst framework; (d) repeating steps (a)-(c) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ and a dispersion energy (Disp $E^{B1}$) associated with $TS^{B1}$, and $TS^{B2}$ and a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta \Delta G^{\ddagger B}$ ($TS^{B2}-TS^{B1}$), and an absolute difference in dispersion energies $|\Delta \text{Disp } E^B|$ calculated as $|\Delta(\text{Disp } E^{B2}-\text{Disp } E^{B1})|$ for migratory insertion of the ethylene molecule versus the α-olefin molecule in the second metallocene catalyst framework; and (e) identifying the first test substituent of the second metallocene catalyst framework as (1) enhancing α-olefin co-monomer incorporation into a polyethylene co-polymer relative to the first metallocene catalyst framework when $\Delta \Delta G^{\ddagger B} < \Delta \Delta G^{\ddagger A}$, when $|\Delta \text{Disp } E^B| > |\Delta \text{Disp } E^A|$, or a combination thereof, or (2) enhancing ethylene incorporation into a polyethylene co-polymer relative to the first metallocene catalyst framework when $\Delta \Delta G^{\ddagger B} > \Delta \Delta G^{\ddagger A}$, when $|\Delta \text{Disp } E^B| < |\Delta \text{Disp } E^A|$, or a combination thereof.

This method and the information provided by the method can allow the skilled person to identify, design, and prioritize catalyst structures for use as olefin polymerization catalysts where a target co-monomer selectivity is desired. Steps (a) through (c) of the method immediately above can be repeated again using a third metallocene catalyst framework analogous to that described immediately above, in which at least one of the $\eta^5$-cycloalkadienyl ligands comprises a second test substituent, which can be identified as a co-monomer incorporator or a co-monomer rejecter relative to the first metallocene catalyst framework and/or the second metallocene catalyst framework.

According to another aspect, the present disclosure provides a method of calculating and comparing the number of stabilizing, non-covalent (dispersion-type) interactions (NCI) in different transition states which also can allow the skilled person to identify, design, and prioritize catalyst structures for use as olefin polymerization catalysts where a target co-monomer selectivity is desired. For example, in an aspect, there is provided a method for designing a Group 4 metallocene olefin polymerization catalyst, the method comprising: (a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework; (b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an α-olefin co-monomer molecule into the metal-hydrocarbyl ligand bond of the first metallocene catalyst framework; (c) determining, by at least one processor of a device, the relative energies of each of the first ground state model structure ($GS^A$), the first transition state model structure ($TS^{A1}$) including a dispersion energy (Disp $E^{A1}$) associated with $TS^{A1}$, and the second transition state model structure ($TS^{A2}$) including a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A2}-GS^A$), and $\Delta \Delta G^{\ddagger A}$ ($TS^{A2}-TS^{A1}$) for migratory insertion of the ethylene molecule versus the α-olefin molecule in the first metallocene catalyst framework; (d) determining, by at least one processor of a device, the number of stabilizing, non-covalent (dispersion-type) interactions (NCI) within a distance of from 2.5 Å to 4.0 Å, inclusive, between (1) the ethylene molecule and the substituted or unsubstituted $\eta^5$-cycloalkadienyl ligands in the first transition state model structure $TS^{A1}$ ($NCI^{A1}$), and (2) the α-olefin molecule and the substituted or unsubstituted $\eta^5$-cycloalkadienyl ligands in the second transition state model structure $TS^{A2}$ ($NCI^{A2}$), and difference between the number of these NCI interactions ($\Delta NCI^A$); (e) repeating steps (a)-(d) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ including a dispersion energy (Disp $E^{B1}$) associated with $TS^{B1}$, $TS^{B2}$ including a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta \Delta G^{\ddagger B}$ ($TS^{B2}-TS^{B1}$), and the number of stabilizing, non-covalent (dispersion-type) interactions in $TS^{B1}$ ($NCI^{B1}$) and $TS^{B2}$ ($NCI^{B2}$), and difference between the numbers of these NCI interactions ($\Delta NCI^B$), for migratory insertion of the ethylene molecule versus the α-olefin molecule in the second metallocene catalyst framework; and (f) identifying the first test substituent of the second metallocene catalyst framework as (1) enhancing α-olefin co-monomer incorporation into a polyethylene co-polymer relative to the first metallocene catalyst framework when $\Delta \Delta G^{\ddagger B} < \Delta \Delta G^{\ddagger A}$, when $\Delta NCI^B > \Delta NCI^A$, or a combination thereof, or (2) enhancing ethylene incorporation into a polyethylene co-polymer relative to the first metallocene catalyst framework when $\Delta \Delta G^{\ddagger B} > \Delta \Delta G^{\ddagger A}$, when $\Delta NCI^B < \Delta NCI^A$, or a combination thereof.

Steps (a) through (d) of the method immediately above also may be repeated again using a third metallocene catalyst framework analogous to that described immediately above, in which at least one of the $\eta^5$-cycloalkadienyl ligands comprises a second test substituent, which can be identified as a co-monomer incorporator or a co-monomer rejecter relative to the first metallocene catalyst framework and/or the second metallocene catalyst framework.

These and other embodiments and aspects of the processes, methods, compositions, and catalyst systems are described more fully in the Detailed Description and claims and further disclosure such as the Examples provided herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures form part of the present specification and are included to further demonstrate certain aspects of the present disclosure. The invention may be better understood by reference to one or more of these figures in combination with the detailed description of specific aspects presented herein.

FIG. 6A provides an NCI visualization of a catalyst scaffold comprising an unsubstituted indenyl framework (L1), illustrating a 1-hexene migratory insertion into the Zr—Pr (zirconium-propyl) bond of the [μ-Me$_2$Si(η$^5$-C$_9$H$_6$)$_2$Zr] (6) catalyst scaffold.

FIG. 6B provides an NCI visualization of a catalyst scaffold comprising a 4-fluoro substituted indenyl framework (L2), illustrating a 1-hexene migratory insertion into the Zr—Pr (zirconium-propyl) bond of the [μ-Me$_2$Si(η$^5$-4-FC$_9$H$_5$)$_2$Zr] (6-F) catalyst scaffold.

FIG. 6C provides an NCI visualization of a catalyst scaffold comprising a 4-dicyclohexylamine substituted indenyl framework (L3), illustrating a 1-hexene migratory insertion into the Zr—Pr (zirconium-propyl) bond of the {-Me$_2$Si[η$^5$-4-N(C$_6$H$_{11}$)$_2$(C$_9$H$_6$)]$_2$Zr} (6-NCy$_2$, also 6-N(C$_6$H$_{11}$)$_2$) catalyst scaffold.

FIG. 6D provides an NCI visualization of a catalyst scaffold comprising a 4-methyl substituted indenyl framework (L4), illustrating a 1-hexene migratory insertion into the Zr—Pr (zirconium-propyl) bond of the [μ-Me$_2$Si(η$^5$-4-(3-CH$_3$C$_6$H$_4$)C$_9$H$_6$)$_2$Zr] (8-Me) catalyst scaffold.

DETAILED DESCRIPTION OF THE DISCLOSURE

Figure 1:
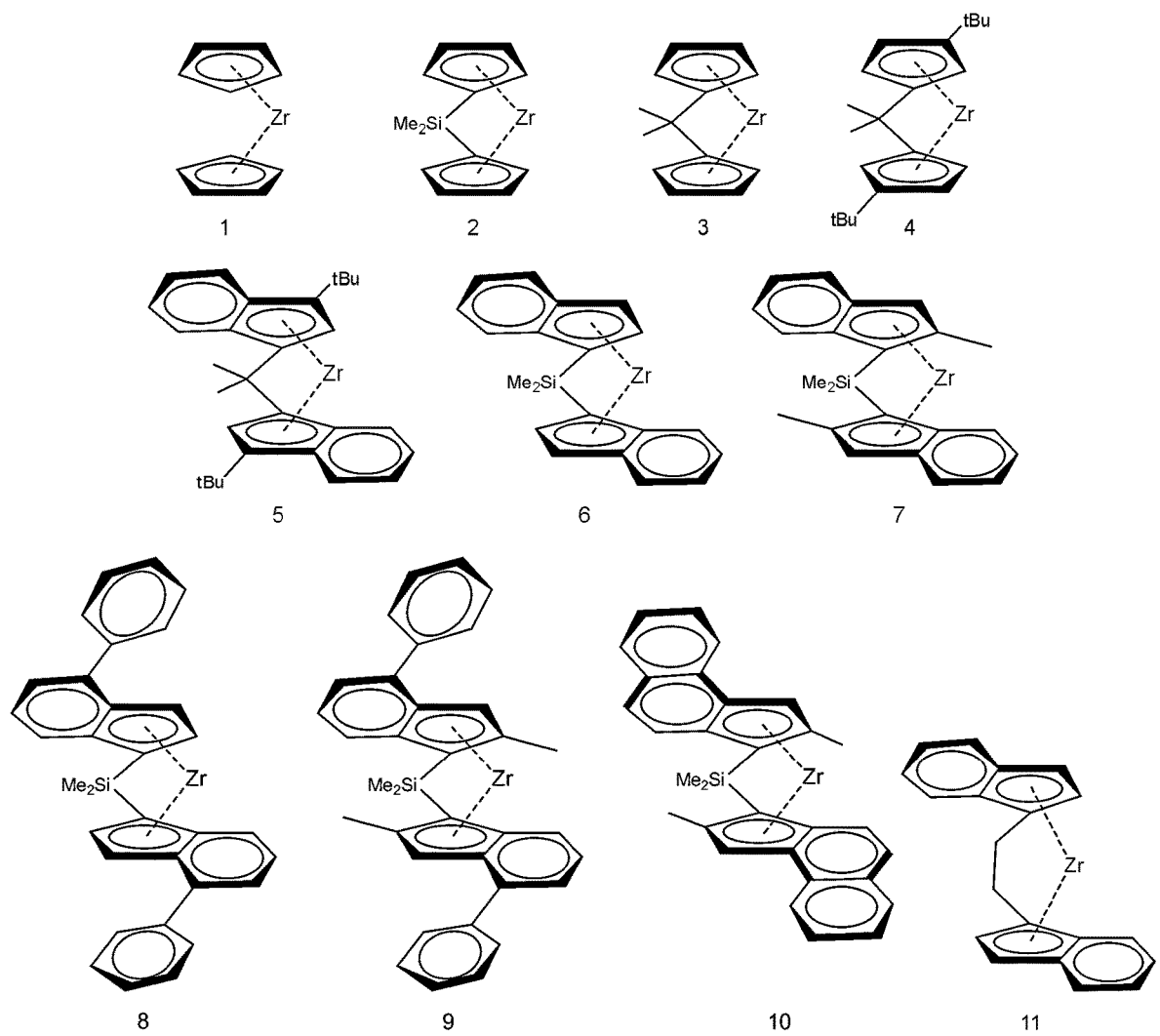
FIG. 1 illustrates an aspect of the disclosure showing representative zirconocene catalyst frameworks or scaffolds which were used in the methods disclosed herein.

Among other things, this disclosure provides new methods for the design and development of ethylene polymerization catalysts, including Group 4 metallocene catalysts such as zirconocene catalysts, which are based on an improved ability to adjust or modulate co-monomer selectivity into the growing polymer chain. In an aspect, it has been unexpectedly discovered through computational analysis of catalysts that stabilizing non-covalent dispersion type interactions can be used to modulate co-monomer selectivity into the polyethylene chain. By designing catalysts that incorporate a greater number of such stabilizing non-covalent dispersion type interactions, α-olefin co-monomer incorporation can be enhanced.

Definitions

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, 2$^{nd}$ Ed (1997) can be applied, as long as that definition does not conflict with any other disclosure or definition applied herein, or render indefinite or non-enabled any claim to which that definition is applied.

To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example, a method can comprise several recited steps (and other non-recited steps) but utilize a catalyst composition preparation consisting of specific steps but utilize a catalyst composition comprising recited components and other non-recited components. While compositions, processes, and computational methods are described in terms of "comprising" various components or steps, the compositions, processes, and computational methods can also "consist essentially of" or "consist of" the various components or steps.

The terms "a," "an," and "the" are intended, unless specifically indicated otherwise, to include plural alternatives, e.g., at least one. For instance, the disclosure of "an organoaluminum compound" is meant to encompass one organoaluminum compound, or mixtures or combinations of more than one organoaluminum compound unless otherwise specified.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethyl-propane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified or unless the context requires otherwise, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. In an aspect, the context could require other ranges or limitations, for example, when the subject carbon-containing group is an aryl group or an alkenyl group, the lower limit of carbons in these subject groups is six carbon atoms and two carbon atoms, respectively. Moreover, other identifiers or qualifying terms may be utilized to indicate the presence or absence of a particular substituent, a particular regiochemistry and/or stereochemistry, or the presence of absence of a branched underlying structure or backbone, and the like.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing that a bond angle can be from 900 to 100°, Applicant's intent is to recite individually 90°, 91°, 92°, 93°, 94°, 95°, 96°, 99°, 98°, 99°, and 100°, including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means ±15% of the stated value, ±10% of the stated value, 5% of the stated value, 3% of the stated value, ±2% of the stated value, or +1% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference or prior disclosure that Applicant may be unaware of at the time of the filing of the application.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

Specific chemical groups may be specified according to the atom which is bonded to the metal or bonded to another chemical moiety as a substituent, such as an "oxygen-bonded group," which is also called an "oxygen group." For example, an oxygen-bonded group includes species such as hydrocarbyloxide (—OR where R is a hydrocarbyl group, also termed hydrocarboxy), alkoxide (—OR where R is an alkyl group), aryloxide (—OAr where Ar is an aryl group), or substituted analogs thereof, which function as ligands or substituents in the specified location. Therefore, an alkoxide group and an aryloxide group are each a subgenus of a hydrocarbyloxide (hydrocarbyloxy) group. A similar definition applies to chemical groups which may be specified according to the atom which is bonded to the metal or bonded to another chemical moiety as a substituent, in which the free valence is situated on a heteroatom (non-carbon atom), such as a "sulfur group," "nitrogen group," "phosphorus group," "arsenic group," "silicon group," "germanium group," "tin group," "lead group," "boron group," "aluminum group," and the like.

A chemical "group" also may be described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. For example, an "alkyl group" formally can be derived by removing one hydrogen atom from an alkane, while an "alkanediyl group" (also referred to as a "alkylene group") formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," which encompasses an "alkyl group," an "alkanediyl group," and materials have three or more hydrogen atoms, as necessary for the situation, removed from the alkane. The disclosure that a substituent, ligand, or other chemical moiety can constitute a particular "group" implies that the known rules of chemical structure and bonding are followed when that group is employed as described. When describing a group as being "derived by," "derived from," "formed by," or "formed from," such terms are used in a formal sense and are not intended to reflect any specific synthetic method or procedure, unless specified otherwise or the context requires otherwise.

The term "organyl group" is used herein in accordance with the definition set forth by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, (among others known to those having ordinary skill in the art) as members. When bonded to a transition metal, an "organyl group," "organylene group," or "organic group" can be further described according to the usual η (eta-x) nomenclature, in which x is an integer corresponding to the number of atoms which are coordinated to the transition metal or are expected to be coordinated to the transition metal, for example, according to the 18-electron rule.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

The term "hydrocarbyl" group is used herein in accordance with the definition specified by IUPAC as follows: a univalent group formed by removing a hydrogen atom from a hydrocarbon (that is, a group containing only carbon and hydrogen). Non-limiting examples of hydrocarbyl groups include ethyl, phenyl, tolyl, propenyl, cyclopentyl, and the like. The term "hydrocarbylene" group is also used herein in accordance with the definition specified by IUPAC as follows: a "hydrocarbylene" group refers to a divalent group formed by removing two hydrogen atoms from a hydrocarbon or a substituted hydrocarbon, the free valencies of which are not engaged in forming a double bond. By way of example and comparison, examples of hydrocarbyl and hydrocarbylene groups include, respectively: aryl and arylene; alkyl and alkanediyl (or "alkylene"); cycloalkyl and cycloalkanediyl (or "cycloalkylene"); aralkyl and aralkanediyl (or "aralkylene"); and so forth. For example, an "arylene" group is used in accordance with IUPAC definition to refer to a bivalent group derived from arenes by removal of a hydrogen atom from two ring carbon atoms, which may also be termed an "arenediyl" group. Examples of hydrocarbylene groups include but are not limited to: 1,2-phenylene; 1,3-phenylene; 1,2-propandiyl; 1,3-propandiyl; 1,2-ethandiyl; 1,4-butandiyl; 2,3-butandiyl; and methylene (—CH$_2$—).

The term "heterohydrocarbyl" group is used herein to refer to a univalent group, which can be linear, branched or cyclic, formed by removing a single hydrogen atom from a heteroatom of a parent "heterohydrocarbon" molecule, the heterohydrocarbon molecule being one in which at least one carbon atom is replaced by a heteroatom. Therefore, a "heteroatom" refers to a non-carbon atom such as oxygen, sulfur, nitrogen, phosphorus, silicon, and the like. Examples of "heterohydrocarbyl" groups formed by removing a single hydrogen atom from a heteroatom of a heterohydrocarbon molecule include, for example: [1] a hydrocarbyloxide group, for example, an alkoxide (—OR) group such as tert-butoxide or aryloxide (—OAr) group such as a substituted or unsubstituted phenoxide formed by removing the hydrogen atom from the hydroxyl (OH) group of a parent alcohol or a phenol molecule; [2] a hydrocarbylsulfide group, for example, an alkylthiolate (—SR) group or arylthiolate (—SAr) group formed by removing the hydrogen atom from the hydrogensulfide (—SH) group of an alkylthiol or arylthiol; [3] a hydrocarbylamino group, for example, an alkylamino (—NHR) group or arylamino (—NHAr) group formed by removing a hydrogen atom from the amino (—NH$_2$) group of an alkylamine or arylamine molecule; and [4] a trihydrocarbylsilyl group such as trialkylsilyl (—SiR$_3$) or triarylsilyl (—SiAr$_3$) group.

An "aliphatic" compound is a class of acyclic or cyclic, saturated or unsaturated, carbon compounds, excluding aromatic compounds, e.g., an aliphatic compound is a non-aromatic organic compound. An "aliphatic group" is a generalized group formed by removing one or more hydrogen atoms (as necessary for the particular group) from a carbon atom of an aliphatic compound. Aliphatic compounds and therefore aliphatic groups can contain organic functional group(s) and/or atom(s) other than carbon and hydrogen.

The term "olefin" is used herein in accordance with the definition specified by IUPAC: acyclic and cyclic hydrocarbons having one or more carbon-carbon double bonds apart from the formal ones in aromatic compounds. Thus, the term "olefin" includes aliphatic and aromatic, acyclic and cyclic, and/or linear and branched compounds having at least one carbon-carbon double bond that is not part of an aromatic ring or ring system unless specifically stated otherwise. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise. With respect to the olefin oligomerization reactions of this disclosure, the computational and reaction studies are conducted with ethylene, so use of the term "olefin" generally refers to ethylene, unless the context of the disclosure allows or requires otherwise.

According to the context of the disclosure, and unless otherwise specified, the abbreviations which designate a carbon count, such as "C6" or "C$_6$", can be used to refer to all hydrocarbon compounds having the specified number of carbon atoms, such as six carbon atoms designated here.

An "aromatic group" refers to a generalized group formed by removing one or more hydrogen atoms (as necessary for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms by trivalent or divalent heteroatoms, in such a way as to maintain the continuous pi-electron system characteristic of aromatic systems and a number of out-of-plane pi-electrons corresponding to the Hückel rule (4n+2)). While arene compounds and heteroarene compounds are mutually exclusive members of the group of aromatic compounds, a compound that has both an arene group and a heteroarene group that compound generally is considered a heteroarene compound. Aromatic compounds, arenes, and heteroarenes may be mono- or polycyclic unless otherwise specified. Examples of arenes include, but are not limited to, benzene, naphthalene, and toluene, among others. Examples of heteroarenes include, but are not limited to furan, pyridine, and methylpyridine, among others. As disclosed herein, the term "substituted" may be used to describe an aromatic group wherein any non-hydrogen moiety formally replaces a hydrogen in that group, and is intended to be non-limiting.

An arene is an aromatic hydrocarbon, with or without side chains (e.g., benzene, toluene, or xylene, among others). An "aryl group" is a group derived from the formal removal of a hydrogen atom from an aromatic hydrocarbon ring carbon atom from an arene compound. One example of an "aryl group" is ortho-tolyl (o-tolyl), the structure of which is shown here.

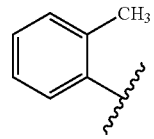 [SMILES: *c1ccccc1C]

The arene can contain a single aromatic hydrocarbon ring (e.g., benzene or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane).

A "heterocyclic compound" is a cyclic compound having at least two different elements as ring member atoms. For example, heterocyclic compounds may comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups may be either aliphatic or aromatic.

An "aralkyl group" is an aryl-substituted alkyl group having a free valance at a non-aromatic carbon atom, for example, a benzyl group and a 2-phenylethyl group are examples of an "aralkyl" group.

A "halide" has its usual meaning; therefore, examples of halides include fluoride, chloride, bromide, and iodide The term "co-catalyst" is used generally herein to refer to compounds such as organoaluminum compounds, organoboron compounds, organozinc compounds, organomagnesium compounds, organolithium compounds, and the like, that can constitute one component of a catalyst composition, when used, for example, with the Group 4 metallocene compounds such as zirconocenes of the disclosure. The term "co-catalyst" is used regardless of the actual function of the compound or any chemical mechanism by which the compound may operate.

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the transition metal catalyst compound(s), any olefin monomer used in the catalytic reaction, and the like. Therefore, the terms "catalyst composition," "catalyst mixture." "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, are used interchangeably throughout this disclosure.

An "organoaluminum compound," is used to describe any compound that contains an aluminum-carbon bond. Thus, organoaluminum compounds include, but are not limited to, hydrocarbyl aluminum compounds such as trihydrocarbyl-, dihydrocarbyl-, or monohydrocarbylaluminum compounds; hydrocarbylaluminum halide compounds; hydrocarbylalumoxane compounds; and aluminate compounds which contain an aluminum-organyl bond such as tetrakis(p-tolyl) aluminate salts. An "organoboron" compound, an "organozinc compound," an "organomagnesium compound," and an "organolithium compound" are used in an analogous fashion to describe any compound that contains a direct metal-carbon bond between an organic group and the recited metal.

References to gaseous, liquid, and/or solid materials refer to the physical state of the material at 25° C. and atmospheric pressure.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Unless otherwise specified, the terms contacted, combined, and "in the presence of" refer to any addition sequence, order, or concentration for contacting or combining two or more components of the polymerization process. Combining or contacting of polymerization components, according to the various methods described herein, can occur in one or more contact zones under suitable contact conditions such as temperature, pressure, contact time, flow rates, etc. The contact zone can be disposed in a vessel (e.g., storage tank, tote, container, mixing vessel, reactor, etc.), a length of pipe (e.g., tee, inlet, injection port, or header for combining component feed lines into a common line), or any other suitable apparatus for bringing the components into contact. The processes can be carried out in a batch or continuous process as can be suitable for a given embodiment.

Use of the term "optionally" with respect to any element of a claim is intended to mean that the subject element is required, or alternatively, is not required. Both alternatives are intended to be within the scope of the claim.

Processes described herein can utilize steps, features, compounds and/or equipment which are independently described herein. The processes described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes described herein can have multiple steps, features (e.g., reagent ratios, formation conditions, among other considerations), and/or multiple compounds and/or compositions using no descriptor or sometimes having the same general identifier. Consequently, it should be noted that the processes described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the processes without detracting from the general disclosure.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Method Description In designing new catalysts, although there has been no single general strategy for computational catalyst design or optimization, one approach which has emerged uses ground-state ligand properties to develop structure-activity relationships. This approach has the advantage of being rapid and identifying chemical connections between seemingly unrelated ligands, however, this approach does not generally lead to the prediction and experimental testing of specific catalysts. Similarly, numerical or data science analysis approaches such as multivariate linear regression and machine learning methods, also generally do not identify chemical principles that enable further catalyst designs. Even quantum mechanical calculations which may screen and rank new catalysts are often limited by the computational resource costs required to calculate large structures and can be ineffective in cases where many conformations exist and there is no clear method to prioritize ligand screening. Therefore, cases in which specific organometallic catalyst predictions have been made followed by experimental realization are elusive.

Non-hydrogen bonding non-covalent dispersion interactions are instantaneously induced attractive dipole-dipole interactions due to electronic fluctuation, and are typically modelled by electronic excitation (electron correlation) to generate the induced dipoles. In transition-metal catalysis, our notion that large ligands have the potential to act as stabilizing (especially those with $\pi$-systems), rather than steric repulsive agents, through stabilizing non-covalent dispersion type interactions provided a design platform for new olefin polymerization catalysts with enhanced co-monomer selectivity.

The inclusion of dispersion interaction energies in olefin migratory insertion transition states, was found to result in significantly tighter correlation with experiment with the metallocenes catalysts has not been recognized previously, and this aspect generally has been discouraged and taught away from in prior studies. For example, some studies showed that the inclusion of semiempirical dispersion resulted in an even greater deviation from experiment for gas phase ligand dissociation energies. See: Weymuth, T.; Couzijn, E. P. A.; Chen, P.; Reiher, M. New Benchmark Set of Transition-Metal Coordination Reactions for the Assessment of Density Functionals. *J. Chem. Theory Comput.* 2014, 10 (8), 3092-3103; Husch, T.; Freitag, L.; Reiher, M. Calculation of Ligand Dissociation Energies in Large Transition-Metal Complexes. *J. Chem. Theory Comput.* 2018, 14 (5), 2456-2468. Others suggested that including explicit dispersion results in overstabilization for BDA and COD ligand substitution by phosphines on Fe and Ru metal centers (BDA=benzylideneacetone, COD=cyclooctadiene). See Jacobsen, H.; Cavallo, L. On the Accuracy of DFT Methods in Reproducing Ligand Substitution Energies for Transition Metal Complexes in Solution: The Role of Dispersive Interactions. *ChemPhysChem* 2012, 13 (2), 562-569. Still others showed that solvation rather than dispersion was the largest factor for deviation from experiment. See: Grimme, S. Comment on: "On the Accuracy of DFT Methods in Reproducing Ligand Substitution Energies for Transition Metal Complexes in Solution: The Role of Dispersive Interactions" by H. Jacobsen and L. Cavallo. *ChemPhysChem* 2012, 13 (6), 1407-1409; Jacobsen, H.; Cavallo, L. Reply to the Comment by Grimme on: "On the Accuracy of DFT Methods in Reproducing Ligand Substitution Energies for Transition Metal Complexes in Solution: The Role of Dispersive Interactions." *ChemPhysChem* 2012, 13 (6), 1405-1406.

Scheme 1 outlines and illustrates at (A) the use of metallocenes as ethylene/linear $\alpha$-olefin (1-alkene) co-monomer polyethylene polymerization catalysts and the goal of developing new catalyst designs to enable modulation of branching to form short-chain branched polyethylene. Scheme 1 also outlines and illustrates at (B) the computational screening of new metallocene catalysts which provide one or more stabilizing non-covalent dispersion type interactions which can enhance co-monomer selectivity and incorporation into the polyethylene chain.

Scheme 1

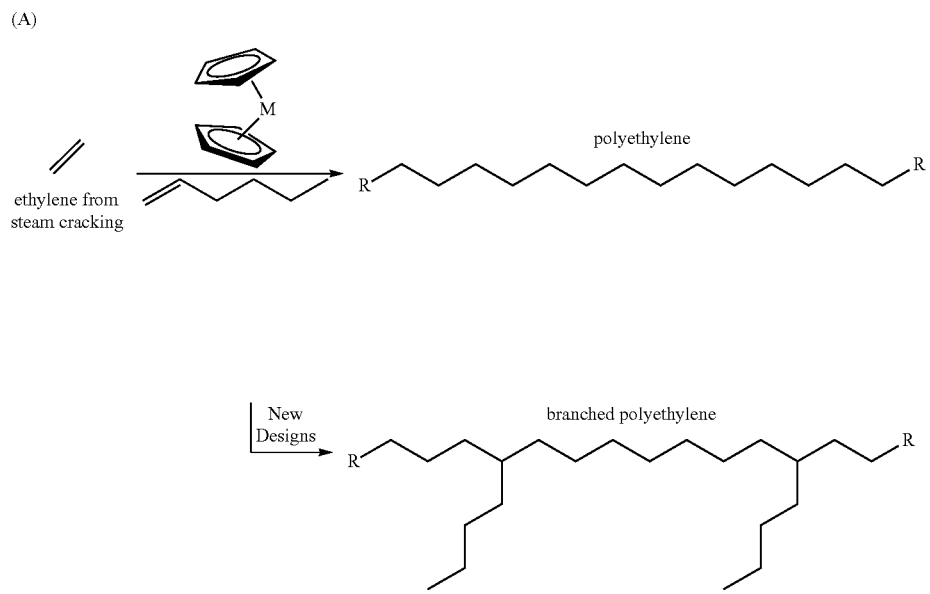

(B)

No Dispersion TS

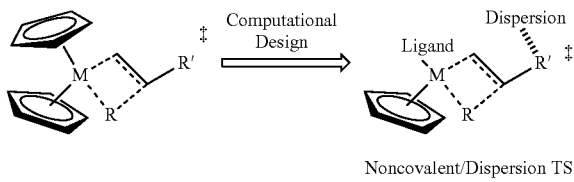

Noncovalent/Dispersion TS

Previous or conventional designs of metallocene olefin polymerization catalysts have centered around the metal center and the repulsive steric influences from the cycloalkadienyl (cyclopentadienyl-type) ligands. In contrast, the general catalyst design disclosed herein is based upon a transition state model which can computationally screen ligands in order to identify new catalyst candidates which can modulate co-monomer incorporation. In an aspect, it has been found for an experimentally validated test set of ethylene and propylene co-polymerization using zirconocene catalysts that determining non-covalent dispersion stabilization can provide quantitative accuracy in providing and validating co-monomer selectivity. In still a further aspect of the disclosure, computational screening may lead to the identification of Group 4 metallocene ligands, particularly zirconocene ligands, which either inhibit or enhance co-monomer such as 1-hexene incorporation during ethylene polymerization. This discovery provides a novel recognition, development, and use of non-covalent dispersion type interactions for catalyzed reactions.

Figure 2A:
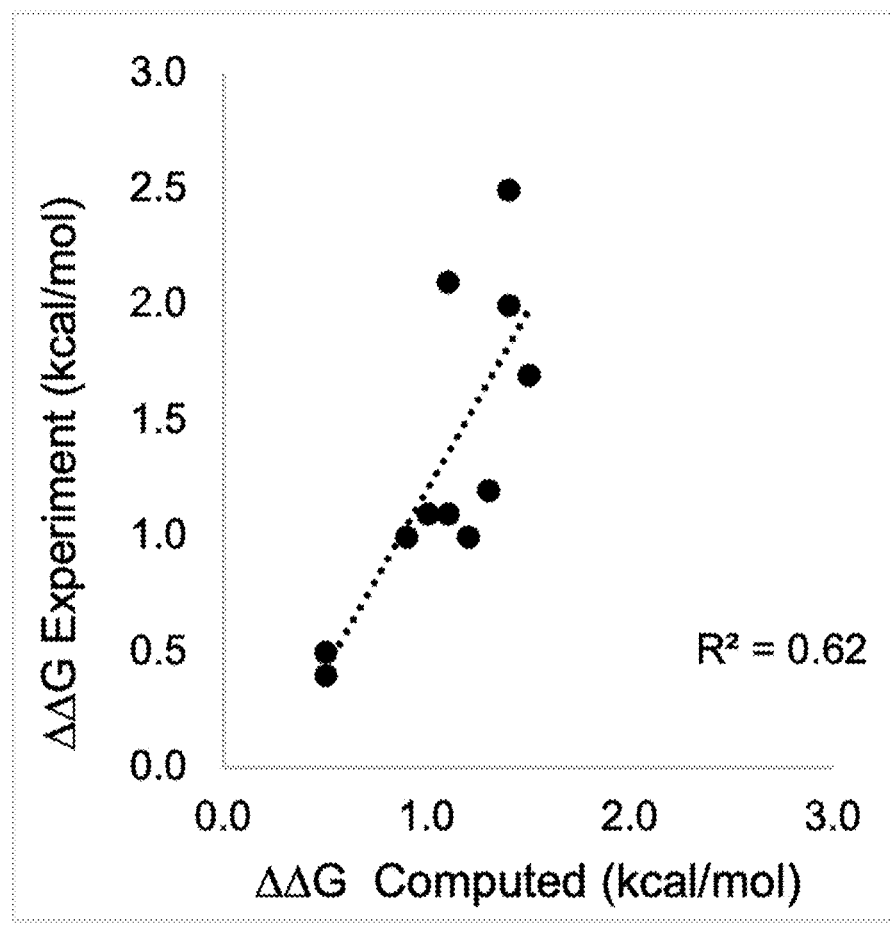
FIG. 2A illustrates an aspect of the disclosure, demonstrating the results of this B3LYP+D3BJ computational method, which includes a dispersion correction. This plot shows the correlation of the computed $\Delta \Delta G$ values against experimental $\Delta \Delta G$ values for a range of zirconocene catalysts such as disclosed herein; see Scheme 1.
Figure 2B:
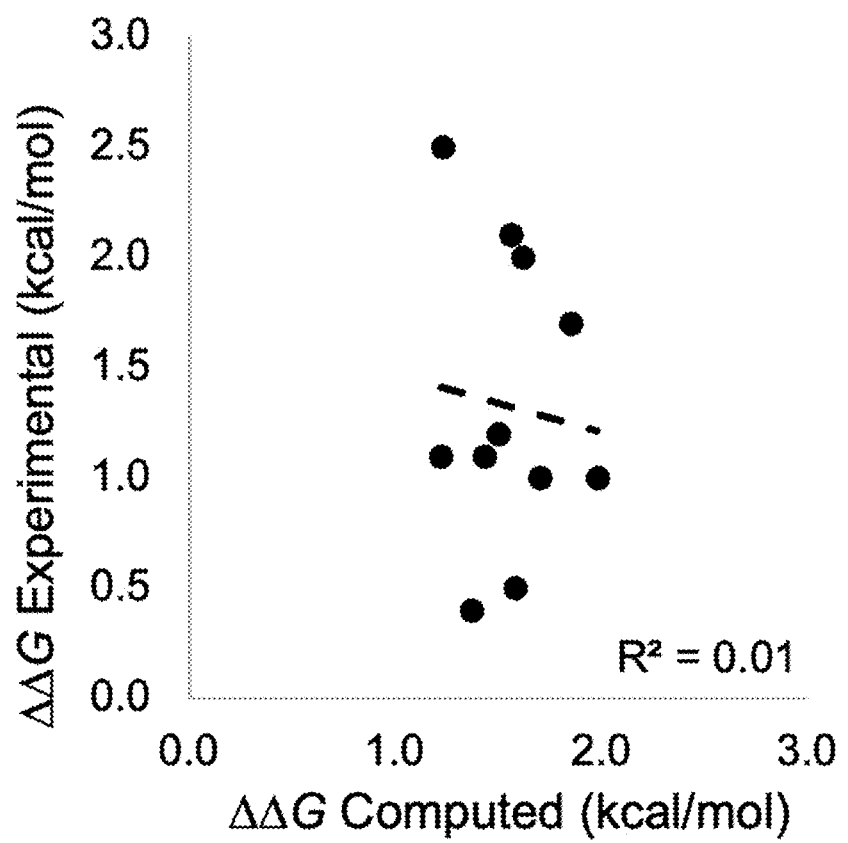
FIG. 2B illustrates an aspect of the disclosure, demonstrating the results of the B3LYP computational method without the dispersion correction for zirconocene catalysts as shown in Table 1. This plot demonstrates the lack of correlation when the dispersion correction (D3BJ) was disabled, and B3LYP was used in the absence of Grimme's D3 dispersion and Becke-Johnson (BJ) dampening. In this plot, the linear correlation with experiment disappears.

The methods of this disclosure employ accurate, experimentally calibrated density-functional theory (DFT) calculations to enable sound computational design of the new metallocene catalysts. In an aspect, after extensive testing it was found that using B3LYP in combination with Grimme's D3 dispersion ("D3") and Becke-Johnson dampening ("BJ") provided ethylene and propylene co-monomer insertion barrier heights that very reasonably matched experiment. This aspect is illustrated in FIG. 2A, where the results of this B3LYP+D3BJ method are demonstrated. FIG. 2A correlates the computed ΔΔG values against experimental ΔΔG values for a range of zirconocene catalysts such as disclosed herein; see Scheme 1. When the dispersion correction was disabled by using only B3LYP in the absence of Grimme's D3 dispersion and Becke-Johnson (BJ) dampening, the linear correlation with experiment disappeared as illustrated in FIG. 2B.

Scheme 2 below illustrates a general outline of an ethylene polymerization mechanism with metallocene catalyst, initially forming a metallocene-ethyl (or "metal-ethyl") intermediate from the migratory insertion of an ethylene molecule into a metal-hydride bond. The mechanism branches from the resulting metal-ethyl intermediate to either (1) continue incorporation of ethylene by a migratory insertion of another ethylene molecule (lower pathway) or (2) incorporate an α-olefin (CH$_2$═CHR) such as propylene, 1-butene, 1-hexene, or 1-octene, which results in an alkyl chain branch from the main, growing polyethylene backbone. Transition states for these two pathways are illustrated in Scheme 2. This methods of this disclosure allow modulating the selectivity of this process to favor one pathway or the other.

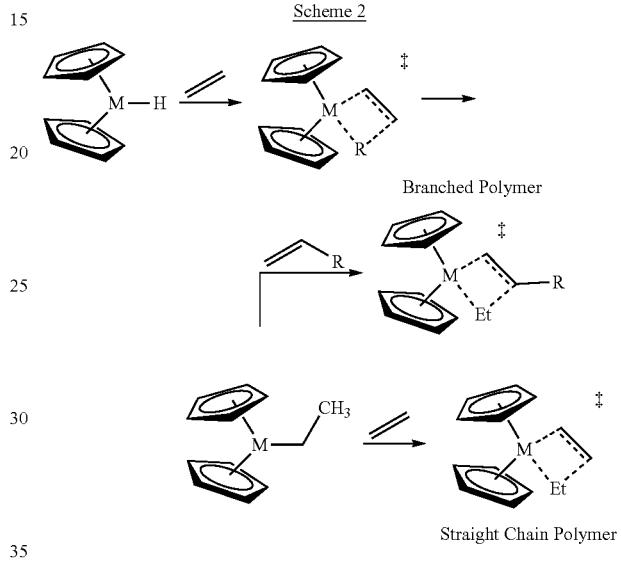

Scheme 2

The identification and influence of dispersion forces on the selectivity for the incorporation of propylene versus ethylene during polymerization were investigated, and while not intending to be theory bound, it was believed that larger linear α-olefins, such as 1-hexene, would be significantly more impacted by dispersion and other non-hydrogen bonding, non-covalent stabilizing interactions than would propylene. The metallocene cyclopentadienyl-type ligands seemed to provide an practical scaffold to design new ligands in which the resulting cyclopentadienyl-type ligand incorporate functional groups to enhance dispersion interactions. See, for example, Scheme 1(B).

Figure 3A:
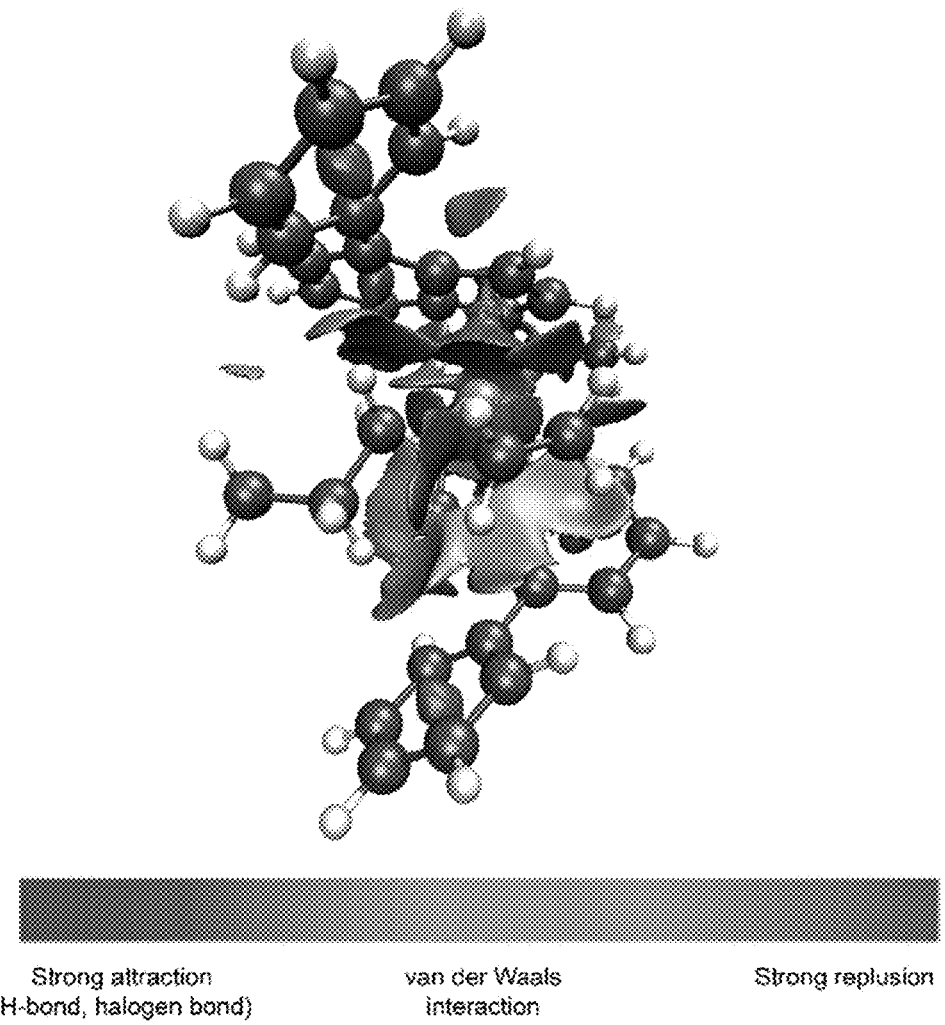
FIG. 3A illustrates a graphic using the NCI visualization technique described by Yang (*J. Am. Chem. Soc.* 2010, 132 (18), 6498-6506), demonstrating the non-covalent interactions for an ethylene migratory insertion transition state, for ethylene insertion into a Zr—Pr (zirconium-propyl) bond. This can be compared to the propylene migratory insertion transition state of FIG. 3B. The catalytic site in this figure is catalyst 8 (see FIG. 1). The interaction color keys are provided, showing the cool colors (blue) represent a strong attractive forces such as a hydrogen bond that might involve a heteroatom, warm colors (red) represent strong repulsive forces, and the intermediate green colors represent the van der Waals attractive forces in effect.
Figure 3B:
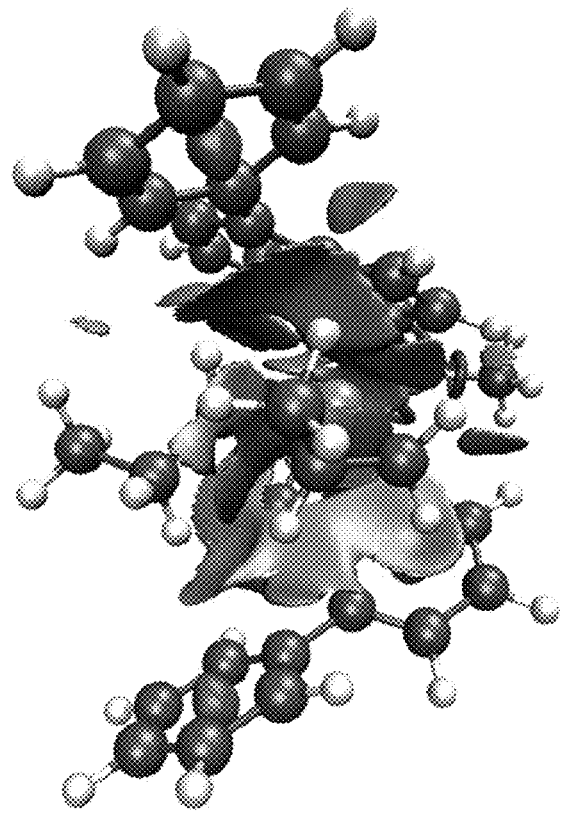
FIG. 3B illustrates a graphic using the NCI visualization technique described by Yang (*J. Am. Chem. Soc.* 2010, 132 (18), 6498-6506), demonstrating the non-covalent interactions for a propylene migratory insertion transition state, for propylene insertion into a Zr—Pr (zirconium-propyl) bond. This can be compared to the ethylene migratory insertion transition state of FIG. 3A. The catalytic site in this figure is catalyst 8 (see FIG. 1). The interaction color keys are provided, showing the cool colors (blue) represent a strong attractive forces such as a hydrogen bond that might involve a heteroatom, warm colors (red) represent strong repulsive forces, and the intermediate green colors represent the van der Waals attractive forces in effect.
Figure 3B:

To investigate our belief that dispersion interactions act as a significant difference operator between ethylene and propylene migratory insertion transition states, we also used the non-covalent interaction (NCI) visualization technique described by Yang et al. (see Johnson, E. R.; Keinan, S.; Mori Sánchez, P.; Contreras García, J.; Cohen, A. J.; Yang, W. *J. Am. Chem. Soc.* 2010, 132 (18), 6498-6506. The results of this visualization method are presented in the non-covalent interaction (NCI) graphics of FIG. 3A and FIG. 3B, which compare the NCI plots for an ethylene migratory insertion transition state (FIG. 3A) to a propylene migratory insertion transition state (FIG. 3B).

This NCI technique examined regions of the electron density where the reduced density gradient vanishes at low electron densities. Repulsive and attractive interactions are determined from the sign of the second eigenvalue of the electron density Hessian. NCIs are visualized in three dimensions, and dispersion interactions are revealed and visualized by green color. Therefore, cool colors (blue)

represent a strong attractive forces such as a hydrogen bond that would involve a heteroatom, warm colors (red) represent strong repulsive forces, and the intermediate green color represents the NCI van der Waals type attractive forces. FIG. 3A and FIG. 3B display NCI plots for the ethylene and propylene insertion transition-state structures for catalyst 8, for insertion into a Zr—Pr (zirconium-propyl) bond. Consistent with the B3LYP+D3BJ calculations described herein, distinct dispersion interactions, shown in green, are observed between the methyl group of the incoming propylene and the aryl group of the ligand, which are not present in the ethylene transition state.

With our identification of dispersion forces as a selectivity feature for controlling co-monomer incorporation, we hypothesized that this effect could be amplified for 1-hexene compared to propylene. In one aspect, new catalysts which provide ethylene/1-hexene selectivity modulation resulting from stabilizing dispersion-type interactions were computationally designed. Consistent with the computed results for ethylene/propylene selectivity, in all designs we assumed rapid equilibration of ethylene and 1-hexene coordination, which enabled direct comparison of transition-state energies as an estimate of selectivity. Generally, each pair-wise dispersion/non-covalent interaction was found to be worth approximately 1 kcal/mol, and because of the relatively small energy difference in transition states, several dispersion interactions may result in a significant impact on selectivity.

In one aspect, FIG. 1 illustrates representative zirconocene catalyst frameworks or scaffolds which were used in the methods disclosed herein. These metallocene frameworks in their unsubstituted forms shown in FIG. 1 were compared to the analogous substituted metallocene frameworks and ΔΔG‡ values for the transition states of ethylene versus α-olefin co-monomer were calculated. This method and the results are demonstrated in detail herein for catalyst scaffolds 6 and 8 of FIG. 1. Therefore, in an aspect, new catalysts based on catalyst scaffolds 6 and 8 illustrated below were computationally designed.

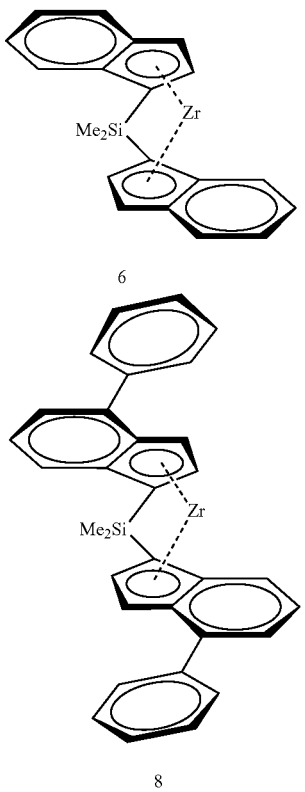

These two ligand types were selected because they have substitution positions that can potentially interact to a significant extent with the n-butyl group of a coordinated 1-hexene. Therefore, 6 and 8 were examined and compared with their substituted analogs designated as 6-R and 8-R, shown below, where R represents a range of substituents.

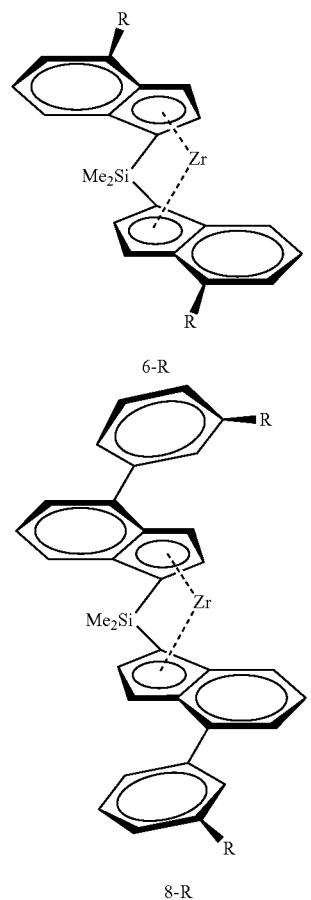

Catalyst scaffold 6 also provides an example of a so-called co-monomer "rejector" where the computed and experimental ΔΔG‡ values for the transition states of ethylene versus co-monomer are relatively large. For the ethylene/1-hexene co-polymerization, the ΔΔG‡ value is 2.41 kcal/mol, corresponding to 16.1 1-hexene/1000 total carbons, indicating that only a small amount of 1-hexene will be incorporated into the ethylene polymer. This ΔΔG‡ ultimately results in a very small number or concentration of butyl branches in the poly(ethylene-co-1-hexene). In contrast, catalyst 8 has a much smaller ΔΔG‡ value for ethylene/1-hexene co-polymerization of 1.58 kcal/mol, corresponding to 52.6 1-hexene/1000 total carbons, and this small energy difference between transition states suggests a larger amount of 1-hexene co-monomer will be incorporated into the ethylene polymer during catalysis.

Figure 4A:
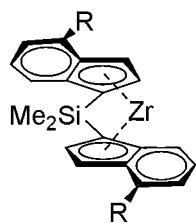
FIG. 4A illustrates new ligand and catalyst designs according to aspects of this disclosure incorporating dispersion interactions. This figure illustrates substituents R to the indenyl-type ligand of catalyst scaffold 6 to examine dispersion type interactions with ethylene and an α-olefin co-monomer.
Figure 4A:
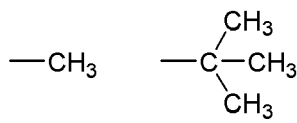
Figure 4A:
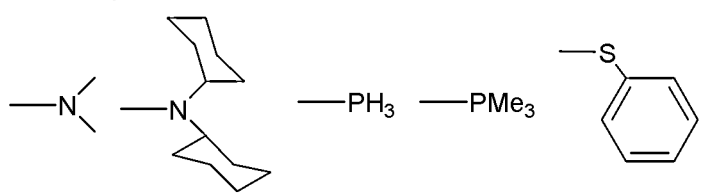
Figure 4A:
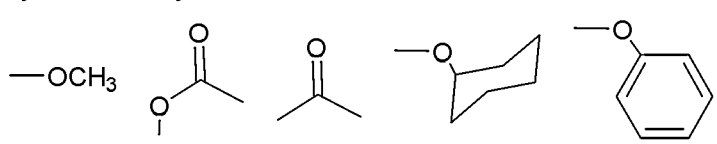
Figure 4B:
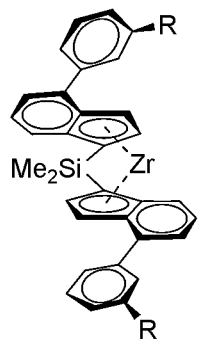
FIG. 4B illustrates new ligand and catalyst designs according to aspects of this disclosure incorporating dispersion interactions. This figure illustrates substituents R to the 4-phenyl-indenyl type ligand of catalyst scaffold 8 to examine dispersion type interactions with ethylene and an α-olefin co-monomer.
Figure 4B:
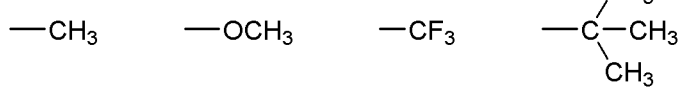

The functional groups attached to the 6 and 8 to provide 6-R and 8-R for computational analysis were selected for their ability to enhance dispersion or were selected as representative of groups that would likely not enhance dispersion interactions; see FIG. 4A and FIG. 4B. Thus, FIG. 4A and FIG. 4B illustrate new ligand and catalyst designs according to aspects of this disclosure incorporating dispersion interactions. FIG. 4A illustrates substituents R to the indenyl-type ligand of catalyst scaffold 6, and FIG. 4B illustrates substituents R to the 4-phenyl-indenyl type ligand of catalyst scaffold 8 which are used to examine dispersion type interactions with ethylene and an α-olefin co-monomer.

Consistent with the hypothesis that non-covalent interactions may be important in olefin co-monomer selectivity, several functionalized forms for catalyst scaffolds 6 and 8 that enhanced dispersion (non-covalent interactions) were identified on the basis of an unexpected and surprising method of determining the extent of non-covalent dispersion-type interactions. Specifically, it was discovered that determining the number of CH—H, CH—X (X=F, Cl, Br, N, O), and CH-π interactions between the olefin substrate and the catalyst scaffold ligands that are present within a distance range of from 2.5 Å to 4.0 Å, and comparing the total number of these dispersion-type interactions in the ethylene versus 1-hexene transition states for migratory insertion into a Zr—Pr (zirconium-propyl) bond, specific substitutions in the functionalized forms for catalyst scaffolds 6 and 8 that enhanced dispersion and thereby enhance co-monomer incorporation could be identified. This "direct counting" method provides an estimate of dispersion stabilization, because it was unexpected found that each additional dispersion-type non-covalent interaction boosted the transition state stabilization which was observed in a corresponding boost in α-olefin co-monomer incorporation.

Figure 5:
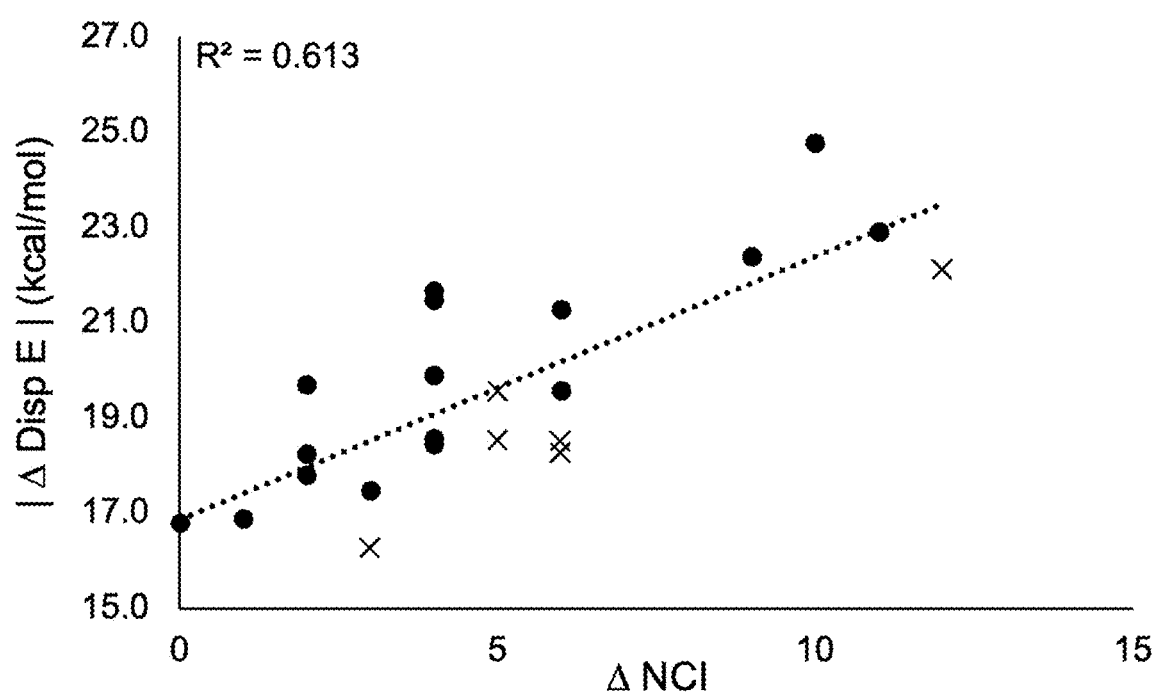
FIG. 5 illustrates aspects of the disclosure in a plot which demonstrates the relationship between the difference in the number of non-covalent interactions (ΔNCI) and the absolute difference in dispersion energy (|ΔDisp E|) comparing ethylene and 1-hexene transition states, for R-substituted indenyl-type ligands of catalyst scaffold 6 and R-substituted 4-phenyl-indenyl type ligand of catalyst scaffold 8. Dispersion energy differences are in kcal/mol. The circles (●) plot catalysts where ΔΔG$^‡$ values (comparing ethylene and 1-hexene transition states for insertion into a zirconium propyl bond) of the R-substituted scaffolds are smaller than the corresponding ΔΔG$^‡$ value without the R functional group, which would lead to enhanced 1-hexene selectivity and hence 1-hexene incorporation. The cross (x) symbols plot catalysts where ΔΔG$^‡$ values (comparing ethylene and 1-hexene transition states for insertion into a zirconium propyl bond) of the R-substituted scaffolds are larger than the corresponding ΔΔG$^‡$ value without the R functional group, which would lead to decreased 1-hexene selectivity, that is, 1-hexene rejection and enhanced ethylene selectivity.
Figure 6A:
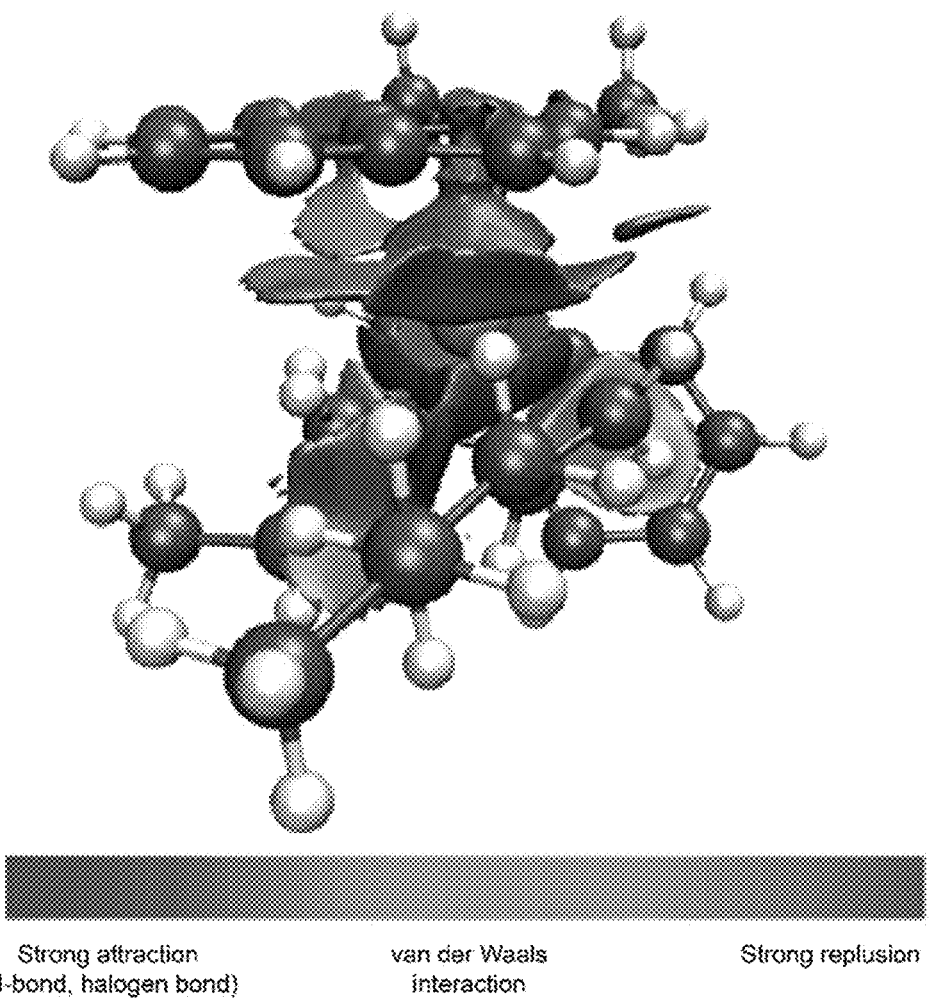
FIG. 6A through FIG. 6D illustrate graphics using the NCI visualization technique described by Yang (*J. Am. Chem. Soc.* 2010, 132 (18), 6498-6506), demonstrating the non-covalent interactions for 1-hexene migratory insertion transition states in a substituted zirconocene catalyst frameworks, for 1-hexene insertion into a Zr—Pr (zirconium-propyl) bond. The interactions are colored according to the color keys in each of FIG. 6A through FIG. 6D, where the cool colors (blue) represent a strong attractive forces such as a hydrogen bond that might involve a heteroatom, warm colors (red) represent strong repulsive forces, and the intermediate green colors represent the van der Waals attractive forces in effect. Quantitative data for the FIG. 6A through FIG. 6D transitions states are in Table 2.
Figure 6B:
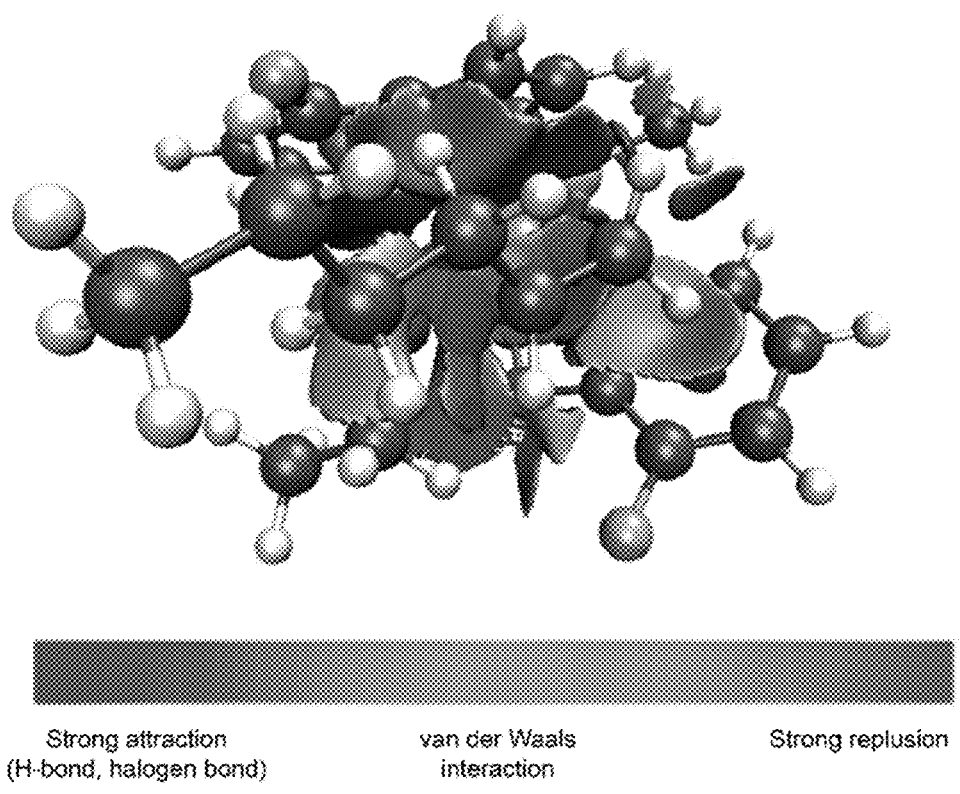
Figure 6C:
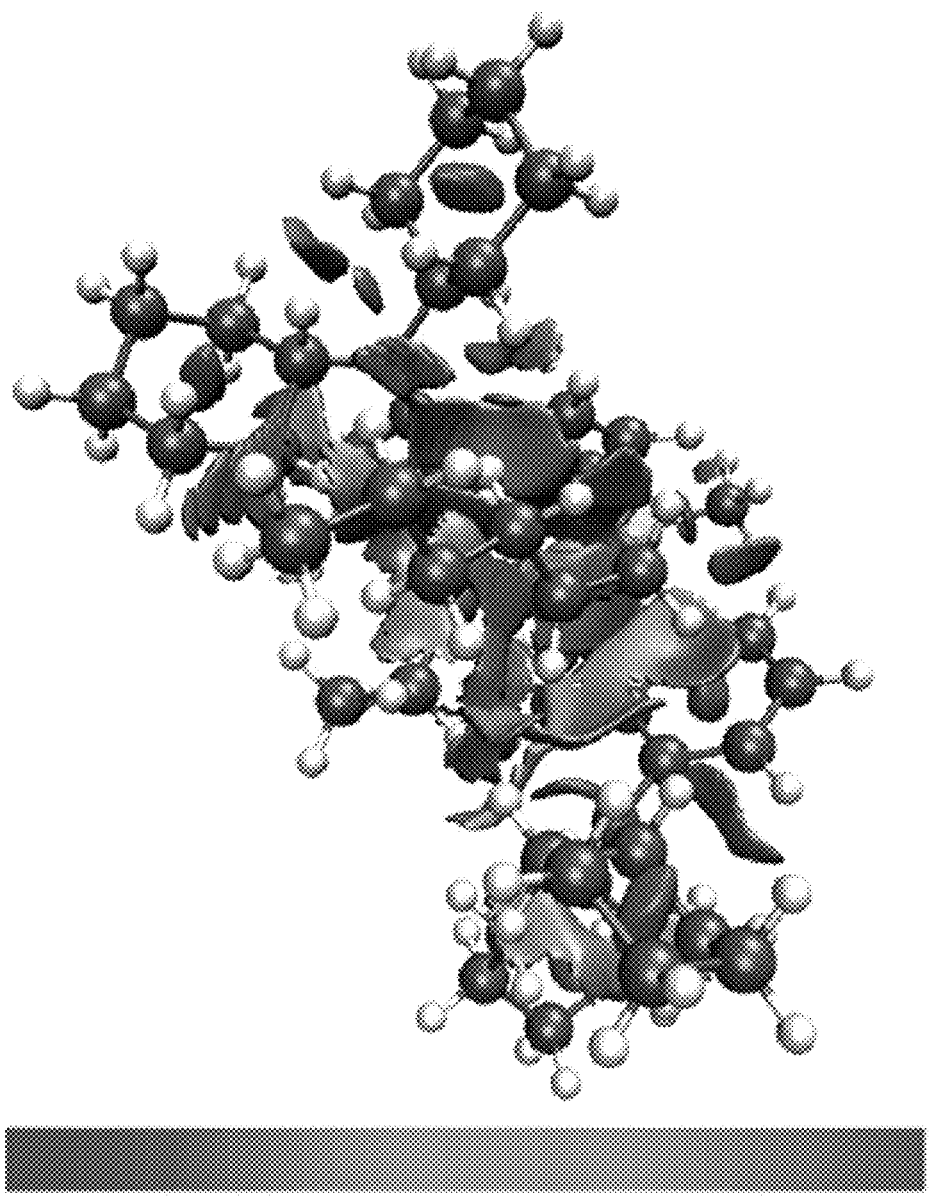
Figure 6D:
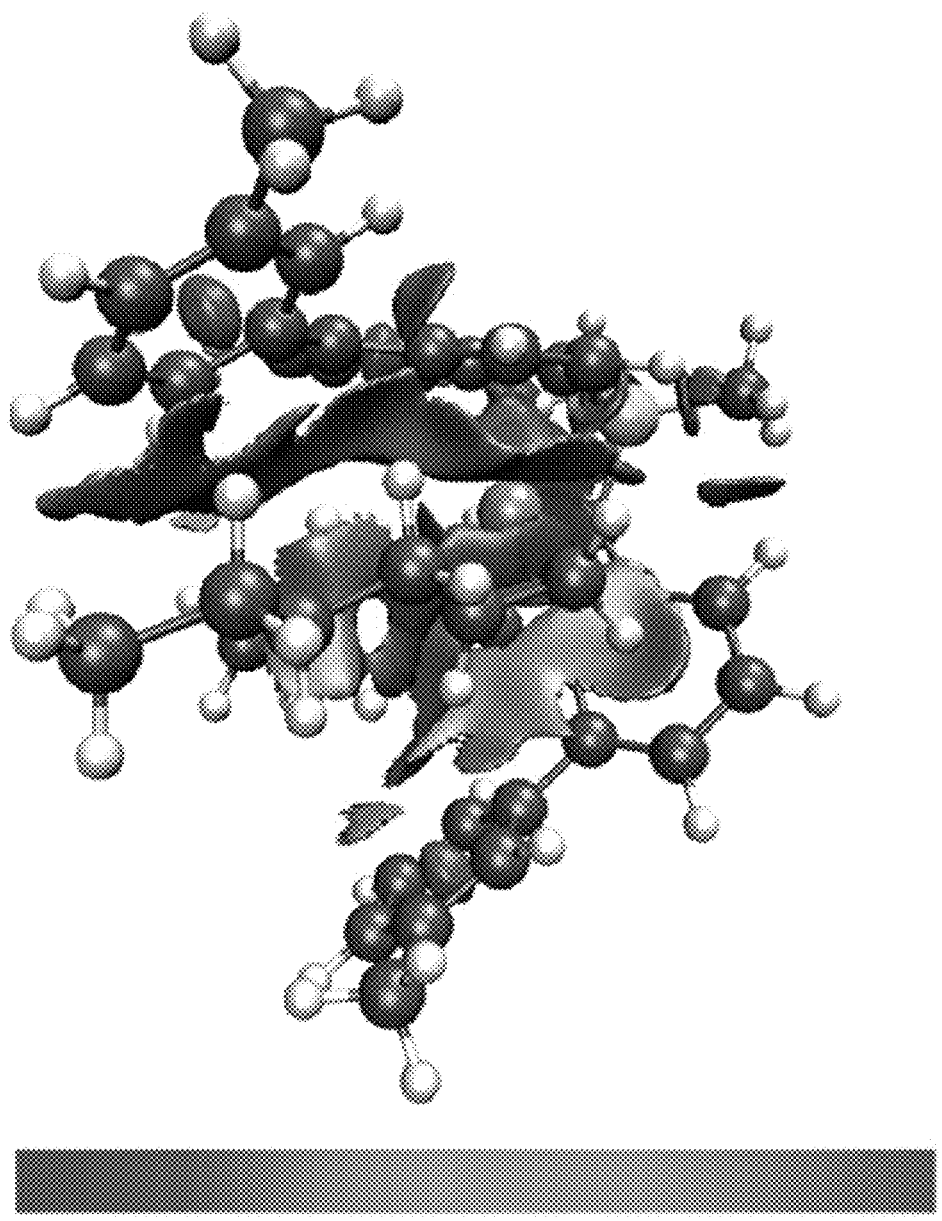

To demonstrate that the direct counting method provides an estimate of dispersion stabilization, for each new catalyst ethylene and 1-hexene migratory insertion transition state, FIG. 5 plots the difference in total dispersion energy (determined with and without the D3(BJ) correction (|Δ Disp E$^\ddagger$|)) versus the counted non-covalent interactions (ΔNCI) that are present within a distance range of from 2.5 Å to 4.0 Å, as described herein. Thus, FIG. 5 demonstrates the relationship between the difference in the number of non-covalent interactions (ΔNCI) and the absolute difference in dispersion energy (|ΔDisp E|) comparing ethylene and 1-hexene transition states for insertion into a zirconium-propyl bond, for R-substituted indenyl-type ligands of catalyst scaffold 6 and R-substituted 4-phenyl-indenyl type ligand of catalyst scaffold 8. Dispersion energy differences are in kcal/mol. The circles (●) plot catalysts where ΔΔG$^\ddagger$ values (comparing ethylene and 1-hexene transition states for insertion into a zirconium propyl bond) of the R-substituted scaffolds are smaller than the corresponding ΔΔG$^\ddagger$ value without the R functional group, which would lead to enhanced 1-hexene selectivity and hence 1-hexene incorporation. The cross (x) symbols plot catalysts where ΔΔG$^\ddagger$ values (comparing ethylene and 1-hexene transition states for insertion into a zirconium propyl bond) of the R-substituted scaffolds are larger than the corresponding ΔΔG$^\ddagger$ value without the R functional group, which would lead to decreased 1-hexene selectivity, that is, 1-hexene rejection and enhanced ethylene selectivity.

Table 1 also provides the ΔΔG$^\ddagger$, ΔNCI, and |Δ Disp E$^\ddagger$| values which are illustrated in FIG. 5, along with the calculated 1-hexenes incorporation per 1000 total carbons (1-Hex/1000 TC) for the difference between 1-hexene and ethylene transition states for the selected substituent R. The order of results presented in Table 1 is with R=H (unsubstituted) first followed by increasing ΔΔG$^\ddagger$ values. The ΔΔG$^\ddagger$ and |Δ Disp E$^\ddagger$| values are in kcal/mol. As illustrated by the qualitative linear correlation shown in FIG. 5, the greater difference in the number of interactions can be correlated with an increased difference in dispersion energy between the ethylene and 1-hexene transition states. This surprising result demonstrates that enhancement of non-covalent interactions can be rationally designed in these zirconocene-type catalysts as a method of enhancing α-olefin co-monomer incorporation. Consistent with our findings, three of the four catalysts with the largest dispersion energies provided a significant shift towards co-monomer incorporation.

For example, the three catalysts based on catalyst scaffold 8 have between 22-25 kcal/mol more dispersion stabilization in their 1-hexene transition states as compared to their ethylene transition states. This energy difference resulted in an overall lower ΔΔG$^\ddagger$ values (0.82 to 1.24 kcal/mol) with the exception of the CF$_3$ substituted version (1.77 kcal/mol), suggesting greater 1-hexene incorporation (85.4 to 155.4 1-hexene/1000 total carbons). This results demonstrates that significant shifts in selectivity may be possible through the sum of many weak dispersion interactions. FIG. 5 and Table 1 also reveal that the new catalysts based on the core of catalyst scaffold 8 provided more possible dispersion interactions (9-12 more interactions for the 1-hexene transition states) than new catalysts based on the core of catalyst scaffold 6 (1-6 more interactions for the 1-hexene transition states). Therefore some ligand scaffolds provide more advantageous frameworks for inserting new dispersion interactions.

TABLE 1

Computational results for ΔΔG$^\ddagger$, 1-hexenes incorporation per 1000 total carbons (1-Hex/1000 TC), ΔNCI, and |Δ Disp E$^\ddagger$| for the difference between 1-hexene and ethylene transition states for the selected substituent R in catalyst scaffolds 6 and 8. ΔΔG$^\ddagger$ and |Δ Disp E$^\ddagger$| are reported in kcal/mol.

|  | R | ΔΔG$^\ddagger$ | 1-Hex/1000 TC | ΔNCI | |ΔDisp E$^\ddagger$| |
|---|---|---|---|---|---|
| 4-phenyl- | H | 1.58 | 52.6 | 4 | 21.48 |
| indenyl | t-Butyl | 0.82 | 155.4 | 10 | 24.78 |
| Catalyst | CH$_3$ | 0.99 | 122.0 | 9 | 22.39 |
| scaffold 8 | OCH$_3$ | 1.24 | 85.4 | 11 | 22.91 |
|  | CF$_3$ | 1.71 | 43.7 | 12 | 22.11 |
| Indenyl | H | 2.41 | 16.1 | 0 | 16.8 |
| Catalyst | OPh | 0.95 | 129.1 | 4 | 21.68 |
| scaffold 6 | F | 0.98 | 123.7 | 1 | 16.88 |
|  | SPh | 1.18 | 93.0 | 4 | 19.89 |
|  | Cl | 1.29 | 79.5 | 2 | 17.79 |
|  | OCH$_3$ | 1.37 | 71.0 | 4 | 18.45 |
|  | Br | 1.41 | 67.0 | 2 | 18.24 |
|  | OCy | 1.64 | 48.3 | 6 | 19.58 |
|  | CH$_3$ | 2.01 | 28.5 | 3 | 17.48 |
|  | Propellane | 2.02 | 28.1 | 2 | 19.7 |
|  | NCy$_2$ | 2.18 | 22.4 | 6 | 21.28 |
|  | OCOCH$_3$ | 2.34 | 17.8 | 4 | 18.57 |
|  | COCH$_3$ | 2.71 | 10.5 | 5 | 18.52 |
|  | PH$_3$ | 4.05 | 1.6 | 6 | 18.25 |
|  | NMe$_2$ | 4.45 | 0.9 | 5 | 19.54 |
|  | PMe$_3$ | 5.94 | 0.1 | 3 | 16.26 |
|  | t-Butyl | 6.97 | 0.0 | 6 | 18.51 |

The computational analysis described herein demonstrates another advantage in being able to analyze dispersion interactions in transition states in addition to any repulsive interactions introduced by the substituents that enhance dispersion. In an aspect, this disclosure demonstrates that dispersion interactions can be designed to enhance co-monomer incorporation; however, it may be possible that the introduction of groups which enhance dispersion interactions and selectivity for 1-hexene incorporation could induce repulsive type interactions, which may energetically exceed and overwhelm any dispersion effects. Indeed, the difficulty in making an a priori determination of the steric demand of a functional or ancillary group in a transition state has been described (Wagner, J. P.; Schreiner, P. R. London Dispersion in Molecular Chemistry—Reconsidering Steric Effects. *Angew. Chemie—Int. Ed.* 2015, 54 (42), 12274-12296) and can make rational catalyst design difficult. Therefore, the computational analysis described herein demonstrates another advantage in being able to determine how many dispersion interactions are possible in transition states in addition to determining whether the dispersion is overall more favorable than repulsive interactions based on Gibbs energies.

This aspect of analyzing dispersion interactions in transition states in addition to any repulsive interactions can be demonstrated by the date in Table 1. For example, catalyst scaffold 8 in Table 1 can be substituted with a t-butyl group which provides a high value of six (6) for calculated $\Delta$NCI (non-covalent interactions) and a $|\Delta$Disp $E^\ddagger|$ of 18.51 kcal/mol, but also a large $\Delta\Delta G^\ddagger$ of 6.97 kcal/mol, leading to a calculated 0 (zero) 1-hexene co-monomers incorporated per 1000 total carbon atoms. In contrast, the unsubstituted analog of catalyst 8 has a calculated $\Delta$NCI of 0 and a $|\Delta$Disp $E^\ddagger|$ of 16.80 kcal/mol, respectively, with a $\Delta\Delta G^\ddagger$ of 2.41 kcal/mol, leading to a calculated 16.1 1-hexene co-monomers incorporated per 1000 total carbon atoms.

In addition to counting the number of non-covalent interactions, for representative examples of the new zirconocene catalysts, a qualitative examination of 3D pictures of the NCI plots was carried out, and quantitative absolutely localized molecular orbital energy decomposition calculations (ALMO-EDA) were performed. See: Horn, P. R.; Mao, Y.; Head-Gordon, M. Probing Non-Covalent Interactions with a Second Generation Energy Decomposition Analysis Using Absolutely Localized Molecular Orbitals. *Phys. Chem. Chem. Phys.* 2016, 18 (33), 23067-23079. The ALMO-EDA method provides the ability to not only access the total dispersion energy in a transition state, but also the other key physical components, such as electrostatic interactions, Pauli repulsion, and orbital (charge transfer) interactions.

Table 2 collects the $\Delta\Delta G^\ddagger$ (kcal/mol) for 1-hexene versus ethylene migratory insertion into the Zr—Pr (zirconium-propyl) bond, $\Delta$NCI for 1-hexene versus ethylene migratory insertion into the Zr—Pr bond, and ALMO-EDA calculation results for 1-hexene transition states of the catalyst scaffolds 6 and 8 with selected substituents R. Specifically, Table 2 data is presented for catalyst scaffolds [$\mu$-Me$_2$Si($\eta^5$-C$_9$H$_6$)$_2$Zr] (6), [$\mu$-Me$_2$Si($\eta^5$-4-FC$_9$H$_5$)$_2$Zr] (6-F), {$\mu$-Me$_2$Si[$\eta^5$-4-N(C$_6$H$_{11}$)$_2$(C$_9$H$_6$)]2Zr} (6-NCy$_2$, also 6-N(C$_6$HH)$_2$), and [$\mu$-Me$_2$Si($\eta^5$-4-(3-CH$_3$C$_6$H$_4$)C$_9$H$_6$)$_2$Zr](8-Me). Therefore, in Table 2 and FIG. 6A through FIG. 6D, L1 is unsubstituted indenyl, L2 is indenyl substituted with fluorine, L3 is indenyl substituted with dicyclohexylamine, and L4 is 4-phenyl indenyl substituted with methyl. From this analysis, these transition states were observed to clearly illustrate the interplay between repulsive steric type interactions and stabilizing dispersion interactions and the resulting effect on $\Delta\Delta G^\ddagger$. The steric repulsion in Table 2 is the sum of the electrostatic and Pauli terms.

FIG. 6A through FIG. 6D illustrate graphics using the NCI visualization technique, which demonstrate the non-covalent interactions for 1-hexene migratory insertion transition states in a substituted zirconocene catalyst frameworks. The interactions are colored according to the key in FIG. 3A and FIG. 3B, thus, the cool colors (blue) represent a strong attractive forces such as a hydrogen bond that might involve a heteroatom, warm colors (red) represent strong repulsive forces, and the intermediate green colors represent the van der Waals attractive forces in effect. Quantitative data for the FIG. 6A through FIG. 6D transitions states are in Table 2.

TABLE 2

Absolutely localized molecular orbital energy decomposition analysis results, $\Delta\Delta G^\ddagger$ (1-hexene-ethylene) values, and difference in the number of non-covalent interactions in the 1-hexene and ethylene transition states ($\Delta$NCI). All energies are in kcal/mol.

| Catalyst Scaffold | Ligand | $\Delta\Delta G^\ddagger$ | $\Delta$ NCI | Electrostatic | Pauli | Steric $^A$ | Disp $^B$ |
|---|---|---|---|---|---|---|---|
| 6 | L1 = unsubstituted indenyl | 2.41 | 0 | −81.97 | 140.33 | 58.36 | −17.50 |
| 6-F | L2 = indenyl substituted with fluorine | 1.78 | 2 | −82.98 | 141.78 | 58.80 | −17.89 |
| 6-NCy$_2$ | L3 = indenyl substituted with dicyclohexylamine | 3.57 | 6 | −90.39 | 160.80 | 70.41 | −26.51 |
| 8-Me | L4 = 4-phenyl indenyl with methyl groups | 0.99 | 11 | −82.17 | 142.46 | 60.29 | −25.12 |

$^A$ Steric repulsion is the sum of the electrostatic and Pauli repulsion terms.
$^B$ Disp dispersion as used here is not the same as $\Delta$Disp $E^\ddagger$ in Table 1, but rather Disp energies are only for the 1-hexene transition state and the interaction between the 1-hexene transition-state fragment and the catalyst transition-state fragment.

The energy values presented in Table 2 are for only the 1-hexene transition state and the interaction between the 1-hexene transition-state fragment and the catalyst transition-state fragment. Therefore, the dispersion energy (Disp) in Table 2 is not the same as the dispersion difference ($\Delta$Disp $E^\ddagger$) presented in Table 1. The impact of steric repulsion can be quantified using the Pauli repulsion and electrostatic terms from the ALMO-EDA calculations, where the steric repulsion is calculated as the sum of Pauli and electrostatic terms.

As the Table 2 data illustrate, the unsubstituted indenyl ligand (L1) has the lowest amount of destabilization due to steric repulsion as well as the least amount of stabilization from dispersion. In comparison, L2, which has a similar amount of destabilization from steric repulsion and stabilization from dispersion, has a smaller $\Delta\Delta G^\ddagger$ resulting in increased selectivity from 1-hexene (16.1 1-Hex/1000TC (L1) versus 123.7 1-Hex/1000TC (L2)). The L3 ligand has the greatest amount of stabilization from dispersion, however, it also has the greatest amount of destabilization due to steric repulsion. Because the stabilization from dispersion is offset by the destabilizing repulsion, the 1-hexene TS (transition state) is destabilized relative to the ethylene, indicated by the larger $\Delta\Delta G^\ddagger$. On the other hand, L4 has an amount of destabilization due to steric repulsion comparable to L1 and L2, but ~7 kcal/mol greater stabilization from dispersion. In this L4 example, because of the increased stabilization resulting from dispersion, 1-hexene TS is stabilized relative to the ethylene TS, resulting in a lower $\Delta\Delta G^\ddagger$ and greater incorporation of 1-hexene (122.0 1-Hex/1000TC). Therefore, in an aspect, this analysis of the Table 2 data highlights how the incorporation of dispersion in catalyst designs can be accomplished with functional group selections which minimize the impact of destabilizing steric repulsion while maximizing the stabilization gained from increased dispersion.

Accordingly, in the B3LYP computational analysis disclosed herein which compared B3LYP+D3BJ and then disabled the dispersion correction by using only B3LYP, this dispersion deletion analysis and NCI visualization analysis revealed that despite a very subtle methyl group induced difference in for ethylene versus propylene transition states, transition-state dispersion interactions for ethylene versus propylene have a significant impact on α-olefin co-monomer selectivity with zirconocene catalysts. This discovery allowed the use of stabilizing non-covalent dispersion interactions as a design feature for ethylene/1-hexene copolymerization and a method for tuning selectivity for α-olefin co-monomer incorporation.

The computational design of new catalysts derived from the catalyst scaffolds of FIG. 1 such as catalysts 6 and 8 demonstrated that the amount of interactions and total stabilizing dispersion interactions can be greatly modulated by the ligand structure, which provides a platform to control co-monomer incorporation selectivity and develop catalysts with co-monomer insertion or rejection pathways. By providing the direct ability to design and control the co-monomer insertion rate according to the methods disclosed herein, the development of improved polyethylene resins with advantaged properties and improved performance can be achieved.

Accordingly, this disclosure provides for a method for designing a Group 4 metallocene olefin polymerization catalyst, in which the method may comprise:
(a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework;
(b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an α-olefin co-monomer molecule into the metal-hydrocarbyl ligand bond of the first metallocene catalyst framework;
(c) determining, by at least one processor of a device, the relative energies of each of the first ground state model structure ($GS^A$), the first transition state model structure ($TS^{A1}$) and a dispersion energy (Disp $E^{A1}$) associated with $TS^{A1}$, and the second transition state model structure ($TS^{A2}$) and a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A2}-GS^A$), $\Delta\Delta G^{\ddagger A}$ ($TS^{A2}-TS^{A1}$), and an absolute difference in dispersion energies $|\Delta\text{Disp } E^A|$ calculated as $|\Delta(\text{Disp } E^{A2}-\text{Disp } E^{A1})|$ for migratory insertion of the ethylene molecule versus the α-olefin molecule in the first metallocene catalyst framework;
(d) repeating steps (a)-(c) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ and a dispersion energy (Disp $E^{B1}$) associated with $TS^{B1}$, and $TS^{B2}$ and a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta\Delta G^{\ddagger B}$ ($TS^{B2}-TS^{B1}$), and an absolute difference in dispersion energies $|\Delta\text{Disp } E^B|$ calculated as $|\Delta(\text{Disp } E^{B2}-\text{Disp } E^{B1})|$ for migratory insertion of the ethylene molecule versus the α-olefin molecule in the second metallocene catalyst framework; and
(e) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B} < \Delta\Delta G^{\ddagger A}$, when $|\Delta\text{Disp } E^B| > |\Delta\text{Disp } E^A|$, or a combination thereof, or (2) enhancing ethylene incorporation into a polyethylene co-polymer relative to the first metallocene catalyst framework when $\Delta\Delta G^{\ddagger B} > \Delta\Delta G^{\ddagger A}$, when $|\Delta\text{Disp } E^B| < |\Delta\text{Disp } E^A|$, or a combination thereof.

In this aspect, this method can further comprise the steps of:
(f) repeating steps (a)-(c) using a third metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, the relative energies of each of a $GS^C$, $TS^{C1}$ and a dispersion energy (Disp $E^{C1}$) associated with $TS^{C1}$, and $TS^{C2}$ and a dispersion energy (Disp $E^{C2}$) associated with $TS^{C2}$, and determining values for $\Delta G^{\ddagger C1}$ ($TS^{C1}-GS^C$), $\Delta G^{\ddagger C2}$ ($TS^{C2}-GS^C$), $\Delta\Delta G^{\ddagger C}$ ($TS^{C2}-TS^{C1}$), and an absolute difference in dispersion energies $|\Delta\text{Disp } E^C|$ calculated as $|\Delta(\text{Disp } E^{C2}-\text{Disp } E^{C1})|$ for migratory insertion of the ethylene molecule versus the α-olefin molecule in the third metallocene catalyst framework; and
(g) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C} < \Delta\Delta G^{\ddagger A}$, when $|\Delta\text{Disp } E^C| > |\Delta\text{Disp } E^A|$, or a combination thereof, (2) enhancing ethylene incorporation into a polyethylene co-polymer relative to the first metallocene catalyst framework when $\Delta\Delta G^{\ddagger C} > \Delta\Delta G^{\ddagger A}$, when $|\Delta\text{Disp } E^C| < |\Delta\text{Disp } E^A|$, or a combination thereof, (3) enhancing α-olefin co-monomer incorporation into a polyethylene co-polymer relative to the second metallocene catalyst framework when $\Delta\Delta G^{\ddagger C} < \Delta\Delta G^{\ddagger B}$, when |$\Delta$Disp $E^C$|>|$\Delta$Disp $E^B$|, or a combination thereof, or (4) enhancing ethylene incorporation into a polyethylene co-polymer relative to the second metallocene catalyst framework when $\Delta\Delta G^{\ddagger C} > \Delta\Delta G^{\ddagger B}$, when |$\Delta$Disp $E^C$|<|$\Delta$Disp $E^B$|, or a combination thereof.

In this fashion, a series of substituents can be examined and ranked according to their ability to enhance α-olefin co-monomer incorporation into a polyethylene co-polymer relative to ethylene, and can serve to tune the catalyst for the desired co-monomer content.

In accordance with a further aspect, this disclosure provides a method for designing a Group 4 metallocene olefin polymerization catalyst, the method comprising:

(a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework;

(b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an α-olefin co-monomer molecule into the metal-hydrocarbyl ligand bond of the first metallocene catalyst framework;

(c) determining, by at least one processor of a device, the relative energies of each of the first ground state model structure ($GS^A$), the first transition state model structure ($TS^{A1}$) including a dispersion energy (Disp $E^{A1}$) associated with $TS^{A1}$, and the second transition state model structure ($TS^{A2}$) including a dispersion energy (Disp $E^{A2}$) associated with $TS^{A2}$, and determining values for $\Delta G^{\ddagger A1}$ ($TS^{A1} - GS^A$), $\Delta G^{\ddagger A2}$ ($TS^{A2} - GS^A$), and $\Delta\Delta G^{\ddagger A}$ ($TS^{A2} - TS^{A1}$) for migratory insertion of the ethylene molecule versus the α-olefin molecule in the first metallocene catalyst framework;

(d) determining, by at least one processor of a device, the number of stabilizing, non-covalent (dispersion-type) interactions (NCI) within a distance of from 2.5 Å to 4.0 Å, inclusive, between (1) the ethylene molecule and the substituted or unsubstituted $\eta^5$-cycloalkadienyl ligands in the first transition state model structure $TS^{A1}$ ($NCI^{A1}$), and (2) the α-olefin molecule and the substituted or unsubstituted $\eta^5$-cycloalkadienyl ligands in the second transition state model structure $TS^{A2}$ ($NCI^{A2}$), and difference between the number of these NCI interactions ($\Delta NCI^A$);

(e) repeating steps (a)-(d) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ including a dispersion energy (Disp $E^{B1}$) associated with $TS^{B1}$, $TS^{B2}$ including a dispersion energy (Disp $E^{B2}$) associated with $TS^{B2}$, and determining values for $\Delta G^{\ddagger B1}$ ($TS^{B1} - GS^B$), $\Delta G^{\ddagger B2}$ ($TS^{B2} - GS^B$), $\Delta\Delta G^{\ddagger B}$ ($TS^{B2} - TS^{B1}$), and the number of stabilizing, non-covalent (dispersion-type) interactions in $TS^{B1}$ ($NCI^{B1}$) and $TS^{B2}$ ($NCI^{B2}$), and difference between the numbers of these NCI interactions ($\Delta NCI^B$), for migratory insertion of the ethylene molecule versus the α-olefin molecule in the second metallocene catalyst framework; and (f) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B} < \Delta\Delta G^{\ddagger A}$, when $\Delta NCI^B > \Delta NCI^A$, or a combination thereof, or (2) enhancing ethylene incorporation into a polyethylene co-polymer relative to the first metallocene catalyst framework when $\Delta\Delta G^{\ddagger B} > \Delta\Delta G^{\ddagger A}$, when $\Delta NCI^B < \Delta NCI^A$, or a combination thereof.

In this aspect, this method can further comprise the steps of:

(g) repeating steps (a)-(d) using a third metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, the relative energies of each of a $GS^C$, $TS^{C1}$ including a dispersion energy (Disp $E^{C1}$) associated with $TS^{C1}$, and $TS^{C2}$ including a dispersion energy (Disp $E^{C2}$) associated with $TS^{C2}$, and determining values for $\Delta G^{\ddagger C1}$ ($TS^{C1} - GS^C$), $\Delta G^{\ddagger C2}$ ($TS^{C2} - GS^C$), $\Delta\Delta G^{\ddagger C}$ ($TS^{C2} - TS^{C1}$), and the number of stabilizing, non-covalent (dispersion-type) interactions in $TS^{C1}$ ($NCI^{C1}$) and $TS^{C2}$ ($NCI^{C2}$), and difference between the numbers of these NCI interactions ($\Delta NCI^C$), for migratory insertion of the ethylene molecule versus the α-olefin molecule in the second metallocene catalyst framework; and (h) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C} < \Delta\Delta G^{\ddagger A}$, when $\Delta NCI^C > \Delta NCI^A$, or a combination thereof, (2) enhancing ethylene incorporation into a polyethylene co-polymer relative to the first metallocene catalyst framework when $\Delta\Delta G^{\ddagger C} > \Delta\Delta G^{\ddagger A}$, when $\Delta NCI^C < \Delta NCI^A$ or a combination thereof, (3) enhancing α-olefin co-monomer incorporation into a polyethylene co-polymer relative to the second metallocene catalyst framework when $\Delta\Delta G^{\ddagger C} < \Delta\Delta G^{\ddagger B}$, when $\Delta NCI^C > \Delta NCI^B$, or a combination thereof, or (4) enhancing ethylene incorporation into a polyethylene co-polymer relative to the second metallocene catalyst framework when $\Delta\Delta G^{\ddagger C} > \Delta\Delta G^{\ddagger B}$, when $\Delta NCI^C < \Delta NCI^B$, or a combination thereof.

When catalyst frameworks are being examined or ranked for their α-olefin co-monomer incorporation into a polyethylene co-polymer according to the number of dispersion-type interactions (NCI), the number of non-covalent dispersion-type interactions $NCI^A$, $NCI^B$, and $NCI^C$ within a distance of from 2.5 Å to 4.0 Å can comprise the number of CH—H, CH—X (X=F, Cl, Br, N, O), and CH-π interactions between the ethylene molecule or the α-olefin molecule and the substituted or unsubstituted $\eta^5$-cycloalkadienyl ligands and the first test substituent of the first metallocene catalyst framework or second metallocene catalyst framework within a distance range of 2.5 to 4.0 Å.

Therefore, this disclosure provides for identifying the first test substituent of the second metallocene catalyst framework, the second test substituent of the third metallocene catalyst framework, or both the first test substituent and the second test substituent as enhancing α-olefin co-monomer incorporation or enhancing ethylene incorporation into the polyethylene co-polymer based upon (a) comparing the relative energies of $\Delta\Delta G^{\ddagger A}$, $\Delta\Delta G^{\ddagger B}$, and/or $\Delta\Delta G^{\ddagger C}$, as appropriate, (b) comparing the relative energies of $|\Delta\text{Disp E}^A|$, $|\Delta\text{Disp E}^B|$ and/or $|\Delta\text{Disp E}^C|$, (c) based upon $\Delta\text{NCI}^A$, $\Delta\text{NCI}^B$, and/or $\Delta\text{NCI}^C$, or combinations of these parameters. For example, if examining the first test substituent of the second metallocene catalyst framework relative to first metallocene catalyst framework containing one or two independently selected substituted or unsubstituted $\eta^5$-cycloalkadienyl ligands, comparisons are made between $\Delta\Delta G^{\ddagger A}$ and $\Delta\Delta G^{\ddagger B}$, $|\Delta\text{Disp E}^A|$ and $|\Delta\text{Disp E}^B|$, $\Delta\text{NCI}^A$ and $\Delta\text{NCI}^B$, or any combination thereof. If examining the second test substituent of the third metallocene catalyst framework relative to first metallocene catalyst framework containing one or two independently selected substituted or unsubstituted $\eta^5$-cycloalkadienyl ligands, comparisons are made between $\Delta\Delta G^{\ddagger A}$ and $\Delta\Delta G^{\ddagger C}$, $|\Delta\text{Disp E}^A|$ and $|\Delta\text{Disp E}^C|$, $\Delta\text{NCI}^A$ and $\Delta\text{NCI}^C$, or any combination thereof. If examining the second test substituent of the third metallocene catalyst framework relative to the first test substituent of the second metallocene catalyst framework, comparisons are made between $\Delta\Delta G^{\ddagger B}$ and $\Delta\Delta G^{\ddagger C}$, $|\Delta\text{Disp E}^B|$ and $|\Delta\text{Disp E}^C|$, $\Delta\text{NCI}^B$ and $\Delta\text{NCI}^C$, or any combination thereof.

As explained further herein, such as in the Examples section, in designing a Group 4 metallocene olefin polymerization catalyst according to this disclosure, the energies of any one or more of the ground state model structures ($GS^A$, $GS^B$, $GS^C$) and any one or more of the transition state model structures ($TS^{A1}$, $TS^{A2}$, $TS^{B1}$, $TS^{B2}$, $TS^{C1}$, $TS^{C2}$) can be calculated as a B3LYP single point energy calculation with a D3BJ correction (B3LYP+D3BJ) using a density functional theory (DFT). In addition, any one or more of the dispersion energies (Disp $E^A$, Disp $E^B$, Disp $E^C$) can be calculated as the difference between a B3LYP single point energy calculation with and without a D3BJ correction using a density functional theory (DFT). Further, any of the number of stabilizing, non-covalent (dispersion-type) interactions ($NCI^{A1}$, $NCI^{A2}$, $NCI^{B1}$, $NCI^{B2}$, $NCI^{C1}$, $NCI^{C2}$) can be calculated using absolutely localized molecular orbital energy decomposition analysis (ALMO-EDA) of the respective transition state model structures ($TS^{A1}$, $TS^{A2}$, $TS^{B1}$, $TS^{B2}$, $TS^{C1}$, and $TS^{C2}$).

Any test substituents can be used with the metallocene catalysts according to the methods of this disclosure, and these methods also allow comparing substituted metallocenes with unsubstituted metallocenes. In an aspect, the first test substituent, the second test substituent, or any additional test substituents can be selected from: a halide (F, Cl, or Br); a $C_1$-$C_{10}$ heterohydrocarbyl group comprising a heteroatom selected from halide (F, Cl, or Br), N, O, P, or S; a $C_1$-$C_{10}$ aliphatic group; or a $C_6$-$C_{10}$ aromatic group. Any combinations of these substituents can be used in these tests, including multiple occurrences of the same substituent. For example, a mono-halide substituted metallocene can be compared with a di-halide substituted metallocene, and the like. Examples of test substituents can include but are not limited to F, Cl, Br, substituted or unsubstituted $C_1$-$C_6$ alkyl, substituted or unsubstituted $C_6$-$C_{10}$ aryl, $C_1$-$C_6$ alkoxide, —OC(O)R$^1$, —CH$_2$C(O)R$^1$, —NR$^{12}$, —PH$_3$, PR$^{13}$, or —SR$^1$, wherein R$^1$ is independently selected from a $C_1$-$C_6$ alkyl or a $C_6$-$C_{10}$ aryl. For example, test substituents can comprise or can be selected from F, Cl, Br, —CH$_3$, —CMe$_3$, —C(CH$_2$)$_3$CH, —CF$_3$, —OMe, —OC(O)Me, —CH$_2$C(O)Me, —OC$_6$H$_{11}$, —OPh, —NMe$_2$, —N(C$_6$H$_{11}$)$_2$, PH$_3$, PMe$_3$, —SC$_6$H$_{11}$, or —SPh.

The catalyst "framework" or "scaffold" used in developing the methods of this disclosure can comprise or can be selected from a metallocene catalyst framework based on titanium, zirconium, or hafnium, that is a Group 4 metallocene catalyst framework. The first or "baseline" metallocene catalyst framework for comparing other substituted metallocenes can comprise a Group 4 metal bonded to a hydrocarbyl ligand and to one or two independently selected substituted or unsubstituted $\eta^5$-cycloalkadienyl ligands. The second, third, or any subsequent metallocene catalyst frameworks comprise the same Group 4 metal, hydrocarbyl ligand, and the one or two $\eta^5$-cycloalkadienyl ligands present in the first or "baseline" metallocene catalyst framework, in addition to one or more substituents present somewhere on the $\eta^5$-cycloalkadienyl ligand(s) that are being tested and compared to the first metallocene. Examples of the substituted or unsubstituted $\eta^5$-cycloalkadienyl ligands can include, but are not limited to, cyclopentadienyl, indenyl, and fluorenyl, which can be linked by a bridging group or unlinked. Further, the $\eta^5$-cycloalkadienyl ligand(s) can be substituted or unsubstituted in the first baseline metallocene but are substituted in the second, third, or any subsequent metallocene catalyst frameworks.

In the disclosed method, any substituent can be used in the second, third, or any subsequent metallocene catalyst frameworks for comparison with the first metallocene catalyst. For example, the substituted or unsubstituted $\eta^5$-cycloalkadienyl ligands, absent the first test substituent and absent the second test substituent, can be selected independently from cyclopentadienyl, methylcyclopentadienyl, t-butylcyclopentadienyl, indenyl, 4-phenyl-indenyl, 2-methylindenyl, 3-t-butylindenyl, 2-methyl-4-phenylindenyl, fluorenyl, or 2-methylfluorenyl.

In a further aspect of the disclosed method for designing a Group 4 metallocene olefin polymerization catalyst, the first metallocene catalyst framework can comprise two independently selected substituted or unsubstituted $\eta^5$-cycloalkadienyl ligands. Moreover, the first metallocene catalyst framework can comprise or can be selected from two independently selected substituted or unsubstituted $\eta^5$-cycloalkadienyl ligands which are bridged by a linking group of the formula (1) >ER$^1$R$^2$, wherein E is C or Si, R$^1$ is hydrogen or a $C_1$-$C_{12}$ hydrocarbyl group, and R$^2$ is hydrogen, a $C_1$-$C_{12}$ hydrocarbyl group, or a $C_3$-$C_{10}$ alkenyl group having a terminal C═C double bond, or (2) CR$^{12}$CR$^2$—, wherein R$^1$ and R$^2$ are selected independently from hydrogen or a $C_1$-$C_6$ hydrocarbyl group. In one aspect, the first metallocene catalyst framework can comprise two independently selected substituted or unsubstituted $\eta^5$-cycloalkadienyl ligands which are bridged by a linking group of the formula >CMe$_2$, —CH$_2$CH$_2$, >SiMe$_2$, or >CH[(CH$_2$)$_2$CH═CH$_2$]. Examples of zirconocene catalyst frameworks or scaffolds which can be used in the methods disclosed herein are illustrated in FIG. 1.

Any hydrocarbyl ligand can be used for the computations of this disclosure, and examples of the hydrocarbyl ligand used for the calculations can be a $C_1$-$C_6$ hydrocarbyl ligand, or alternatively a $C_1$-$C_4$ hydrocarbyl ligand, or alternatively an ethyl (C$_2$) ligand. In another aspect of this disclosure, any α-olefin co-monomer can be used in these computations. For example, the α-olefin co-monomer can comprise or can be selected from propylene, 1-butene, 1-pentene, 1-hexene, 1-heptene, 1-octene, or styrene.

According to another aspect, the first metallocene catalyst framework can comprise one substituted or unsubstituted $\eta^5$-cycloalkadienyl ligand and can further comprises an anionic ligand in addition to the hydrocarbyl ligand which constitutes the growing polymer chain. In this aspect, the first metallocene catalyst framework can comprise one substituted or unsubstituted $\eta^5$-cycloalkadienyl ligand and further comprise an anionic ligand selected from halide, hydride, a $C_1$-$C_{20}$ hydrocarbyl group, a $C_1$-$C_{20}$ heterohydrocarbyl group, tetrahydroborate, or $OBR^{A2}$ or $OSO_2R^A$ wherein $R^A$ is independently a $C_1$-$C_{12}$ hydrocarbyl group. For example, the first metallocene catalyst framework can comprise one substituted or unsubstituted $\eta^5$-cycloalkadienyl ligand and further comprise an anionic ligand selected from F, Cl, Br, a hydride, a $C_1$-$C_{12}$ hydrocarbyl group, a $C_1$-$C_{12}$ hydrocarbyloxide group, a $C_1$-$C_{12}$ hydrocarbylamino group, $C_1$-$C_{12}$ dihydrocarbylamino, or a trihydrocarbylsilyl group wherein each hydrocarbyl is independently a $C_1$-$C_{12}$ hydrocarbyl group. The second, third, or any subsequent metallocene catalyst frameworks can constitute the same ligands as the first metallocene, but are then further substituted for computational comparisons with the first metallocene.

The method for designing a Group 4 metallocene olefin polymerization catalyst according to this disclosure can further comprise the step of synthesizing the Group 4 metallocene catalyst comprising the one or two independently selected $\eta^5$-cycloalkadienyl ligands, wherein at least one of the $\eta^5$-cycloalkadienyl ligands comprises the first test substituent or the second test substituent or any subsequent test substituent. According the method for designing the Group 4 metallocene olefin polymerization catalyst may also further comprise the steps of: (a) providing a Group 4 metallocene catalyst comprising the one or two independently selected $\eta^5$-cycloalkadienyl ligands, wherein at least one of the $\eta^5$-cycloalkadienyl ligands comprises the first test substituent or the second test substituent; and (b) contacting the Group 4 metallocene catalyst with ethylene and an α-olefin co-monomer molecule under polymerization conditions to form a polyethylene co-polymer.

Regarding specific zirconocene catalyst systems that can be designed, in an aspect, this disclosure provides a catalyst system for polymerizing olefins, the catalyst system comprising:
a zirconocene catalyst comprising two $\eta^5$-cycloalkadienyl ligands independently selected from a substituted or an unsubstituted $\eta^5$-cyclopentadienyl ligand or a substituted or an unsubstituted $\eta^5$-indenyl ligand, wherein the two $\eta^5$-cycloalkadienyl ligands are optionally bridged by a linking group; and
one of the $\eta^5$-cycloalkadienyl ligands is substituted with at least one substituent which imparts enhanced dispersion-type interactions in a transition state for a migratory insertion of an α-olefin co-monomer molecule into a metal-hydrocarbyl ligand bond of the zirconocene catalyst versus a migratory insertion of the α-olefin co-monomer molecule into a metal-hydrocarbyl ligand bond of a zirconocene catalyst comprising the corresponding unsubstituted $\eta^5$-cycloalkadienyl ligands.

According to a further aspect, this disclosure provides a catalyst system for polymerizing olefins, the catalyst system comprising:
a zirconocene catalyst comprising two $\eta^5$-cycloalkadienyl ligands independently selected from a substituted or an unsubstituted $\eta^5$-cyclopentadienyl ligand or a substituted or an unsubstituted $\eta^5$-indenyl ligand, wherein the two $\eta^5$-cycloalkadienyl ligands are optionally bridged by a linking group; and
one of the $\eta^5$-cycloalkadienyl ligands is substituted with at least one substituent which imparts enhanced number of stabilizing, non-covalent (dispersion-type) interactions (NCI) within a distance of from 2.5 Å to 4.0 Å, inclusive, between the α-olefin molecule and the at least one substituent in a transition state for a migratory insertion of an α-olefin co-monomer molecule into a metal-hydrocarbyl ligand bond of the zirconocene catalyst versus a migratory insertion of the α-olefin co-monomer molecule into a metal-hydrocarbyl ligand bond of a zirconocene catalyst comprising the corresponding unsubstituted $\eta^5$-cycloalkadienyl ligands.

In an aspect, this catalyst systems for polymerizing olefins according to this disclosure can comprise zirconocene catalysts, which can comprise one of the following structures:

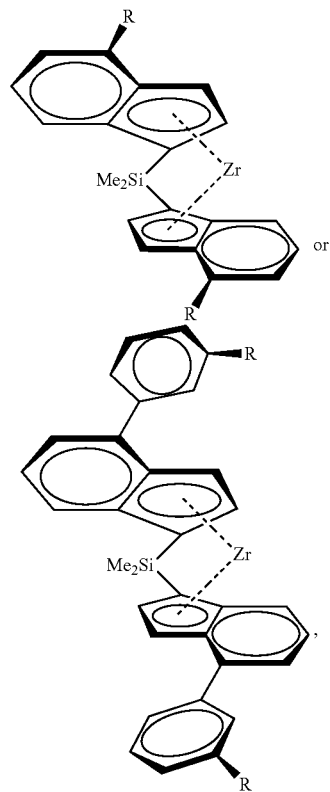

wherein:
R can be selected independently from F, Cl, Br, $C_1$-$C_6$ alkyl, $C_6$-$C_{10}$ aryl, $C_1$-$C_6$ alkoxide, —OC(O)R$^1$, —CH$_2$C(O)R$^1$, —NR$^{12}$, —PH$_3$, PR$^{13}$, or —SR$^1$, and wherein R$^1$ can be independently selected from a $C_1$-$C_6$ alkyl or a $C_6$-$C_{10}$ aryl, in the substituted $\eta^5$-cycloalkadienyl ligands; and
R is H in the corresponding unsubstituted $\eta^5$-cycloalkadienyl ligands.

In this aspect, R can be selected independently from F, Cl, Br, —CH$_3$, —CMe$_3$, —C(CH$_2$)$_3$CH, —CF$_3$, —OMe, —OC(O)Me, —CH$_2$C(O)Me, —OC$_6$H$_{11}$, —OPh, —NMe$_2$, —N(C$_6$H$_{11}$)$_2$, PH$_3$, PMe$_3$, —SC$_6$H$_{11}$, or —SPh, in the substituted $\eta^5$-cycloalkadienyl ligands.

This disclosure also provides for catalyst systems for polymerizing olefins, in which the catalyst system can comprise the Group 4 metallocene olefin polymerization catalyst comprising the Group 4 metal bonded to the hydrocarbyl ligand and to the one or two independently selected substituted or unsubstituted $\eta^5$-cycloalkadienyl ligands, according to any of the aspects described herein, in which at least one of the $\eta^5$-cycloalkadienyl ligands can comprise the first test substituent, the second test substituent, or any subsequent second test substituent, which can be identified as enhancing α-olefin co-monomer incorporation into a polyethylene co-polymer, relative to an α-olefin co-monomer incorporation of the first metallocene catalyst framework. If desired, at least one of the $\eta^5$-cycloalkadienyl ligands can comprise the first test substituent, the second test substituent, or any subsequent second test substituent, which can be identified as enhancing ethylene incorporation into a polyethylene co-polymer, relative to ethylene incorporation of the first metallocene catalyst framework.

In addition to a metallocene, the catalyst system of this disclosure can include any additional components that are needed for polymerizing olefins. For example, the catalyst system may further comprise:
(a) an activator comprising a solid oxide treated with an electron-withdrawing anion (activator-support), an organoboron compound, an organoborate compound, an ionizing ionic compound, an aluminoxane compound, or any combination thereof; and
(b) optionally, a co-catalyst comprising an organoaluminum compound, an organoboron compound, an organozinc compound, an organomagnesium compound, an organolithium compound, or any combination thereof.

In this aspect, the activator can comprises a solid oxide treated with an electron-withdrawing anion, and wherein:
the solid oxide can comprise silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, boehmite, heteropolytungstates, mixed oxides thereof, or any combination thereof; and
the electron-withdrawing anion can comprise fluoride, chloride, bromide, iodide, sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, trifluoroacetate, fluoroborate, fluorozirconate, fluorotitanate, or any combination thereof.

Further to this aspect, the activator can comprises a solid oxide treated with an electron-withdrawing anion, and wherein:
the solid oxide comprises alumina, silica-alumina, silica-coated alumina, or a mixture thereof, and
the electron-withdrawing anion comprises fluoride, sulfate, or phosphate.

Examples of activators include, but are not limited to, fluorided alumina, fluorided silica, fluorided silica-alumina, or fluorided silica-coated alumina (mullite).

According to a further aspect, the catalyst system for polymerizing olefins according to this disclosure can be present and can comprise alkyl aluminum compounds, such as trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, aluminoxanes, or any combination thereof.

EXAMPLES

General Methods. All structures were optimized using DFT (density-functional theory) and confirmed as transition states by frequency analysis in Gaussian 16 (Frisch, M. J.; Trucks, G. W.; Schlegel, H. B.; Scuseria, G. E.; Robb, M. A.; Cheeseman, J. R.; Scalmani, G.; Barone, V.; Petersson, G. A.; Nakatsuji, H.; et al. Gaussian16, Rev. B.01. Gaussian Inc.: Wallingford, C T 2016). The Becke 3-parameter exchange functional (Becke, A. D. Density-Functional Thermochemistry. III. The Role of Exact Exchange. *J. Chem. Phys.* 1993, 98 (7), 5648-5652) was combined with the correlation functional of Lee, Yang, and Parr (Gaussian version) (Lee, C.; Yang, W.; Parr, R. G. Development of the Colle-Salvetti Correlation-Energy Formula into a Functional of the Electron Density. *Phys. Rev. B* 1988, 37 (2), 785-789), the empirical dispersion correction of Grimme (D3) and the damping function of Becke and Johnson (Grimme, S.; Huenerbein, R.; Ehrlich, S. On the Importance of the Dispersion Energy for the Thermodynamic Stability of Molecules. *ChemPhysChem* 2011, 12 (7), 1258-1261; Grimme, S.; Hansen, A.; Brandenburg, J. G.; Bannwarth, C. Dispersion-Corrected Mean-Field Electronic Structure Methods. *Chem. Rev.* 2016, 116 (9), 5105-5154). The B3LYP+D3(BJ) functional was combined with the 6-31G** basis set for main group elements and LANL2DZ basis set and pseudo potential for Zr.

The free energies reported were computed at the B3LYP+D3(BJ)/Def2TZVPP//B3LYP+D3BJ/6-31G**[LANL2DZ] level of theory (see below for further details). The dispersion energy was computed as the difference between B3LYP single point calculations with and without the D3BJ correction. Temperature corrections were applied according to the experimental conditions (323.15K) and no pressure corrections were applied. Standard rigid rotor and harmonic oscillator approximations were used. Additional analysis of the dispersion interactions was performed using the NCI method (Johnson, E. R.; Keinan, S.; Mori Sánchez, P.; Contreras García, J.; Cohen, A. J.; Yang, W. NCI: Revealing Non-Covalent Interactions. *J. Am. Chem. Soc.* 2010, 132 (18), 6498-6506) as implemented in Multiwfn (Lu, T.; Chen, F. Multiwfn: A Multifunctional Wavefunction Analyze. *J. Comput. Chem.* 2012, 33 (5), 580-592) and visualized in VMD (Humphrey, W.; Dalke, A.; Schulten, K. VMD—Visual Molecular Dynamics. *J. Molec. Graph.* 1996, 13, 33-38). Additional absolutely localized molecular orbital energy decomposition analysis (ALMO-EDA) (Horn, P. R.; Mao, Y.; Head-Gordon, M. Probing Non-Covalent Interactions with a Second Generation Energy Decomposition Analysis Using Absolutely Localized Molecular Orbitals. *Phys. Chem. Chem. Phys.* 2016, 18 (33), 23067-23079) calculations were performed in QChem 5.2 (Shao, Y.; Gan, Z.; Epifanovsky, E.; Gilbert, A. T. B.; Wormit, M.; Kussmann, J.; Lange, A. W.; Behn, A.; Deng, J.; Feng, X.; et al. *Advances in Molecular Quantum Chemistry Contained in the Q-Chem 5.2 Program Package. Mol. Phys.* 2015, 113 (2), 184-215).

ALMO-EDA is used to compute interactions between molecular fragments. The interaction is broken into electrostatic, Pauli repulsive, dispersion, charge-transfer, and polarization terms. The Pauli repulsive and electrostatic terms can be combined to quantify the steric repulsion of the molecular fragments. These calculations assume a bare cation as discussed by Linnolahti (Laine, A.; Coussens, B. B.; Hirvi, J.

T.; Berthoud, A.; Friederichs, N.; Severn, J. R.; Linnolahti, M. Effect of Ligand Structure on Olefin Polymerization by a Metallocene/Borate Catalyst: A Computational Study. *Organometallics* 2015, 34 (11), 2415-2421). The growing polymer chain was modeled as a propyl chain and olefin insertions were modelled as front side insertions (Margl, P.; Deng, L.; Ziegler, T. General Aspects of Ethylene Polymerization by D0 and D0fn Transition Metals. *Top. Catal.* 1999, 7, 187-208) occurring in a 2,1-fashion.

Additional Computational Details. All DFT calculations were performed in Gaussian 16 revision B.01. Geometry optimizations were performed at the B3LYP+D3BJ/6-31G [LANL2DZ for Zr] (small) level of theory. Vibrational frequencies were computed to verify stationary points as first-order saddle points (transition states). The B3LYP+D3BJ functional was chosen because it most accurately reproduced the experimental co-polymerization ratios discussed in the main text. The electronic energies were further refined with single point calculations using the def2-TZVPP basis set (large). Final free energies reported are computed at the B3LYP+D3BJ/def2-TZVPP//B3LYP+D3BJ/6-31G [LANL2DZ] level of theory. Free energies are the sum of $E_{large} + \Delta E_{ZPE(small)} + \Delta U_{vib(small)} + \Delta U_{rot(small)} + \Delta U_{trans(small)} + nRT - T\Delta S_{vib(small)} - T\Delta S_{rot(small)} - T\Delta S_{trans(small)}$. E is the total SCF energy. $\Delta E_{ZPE}$(small) is the zero-point energy correction. $\Delta U_{vib(small)}$, $\Delta U_{rot(small)}$, and $\Delta U_{trans(small)}$ are thermal energy vibrational, rotational, and translational corrects. R is the gas constant and T is the temperature. $T\Delta S_{vib(small)}$, $T\Delta S_{rot(small)}$, and $T\Delta S_{trans(small)}$ are temperature dependent vibrational, rotational, and translation entropy corrections. No pressure corrections were applied, and standard harmonic oscillator and rigid rotor approximations were applied. As discussed herein, the dispersion energy was computed by performing small basis set single point calculations with the D3BJ correction turned off. The dispersion energy was computed as the difference in the SCF energies with and without the correction applied.

Absolutely localized molecular orbital energy decomposition analysis calculations (ALMO-EDA) calculations were performed in Q-Chem 5.2 at the B3LYP+D3BJ/6-31G [LANL2DZ] level of theory using the geometries computed using Gaussian16 at the B3LYP+D3BJ/6-31G [LANL2DZ] level of theory. In order to compute dispersion energy from ALMO-EDA a dispersion free density functional is specified, and these calculations used B3LYP. Molecular fragments used in the ALMO-EDA calculation were 1-hexene and the catalyst.

ASPECTS OF THE DISCLOSURE

These and other features of the invention can further include the various aspects, statements, embodiments, and features which are presented below.

Aspect 1. A method for designing a Group 4 metallocene olefin polymerization catalyst, the method comprising:
(a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework;
(b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an α-olefin co-monomer molecule into the metal-hydrocarbyl ligand bond of the first metallocene catalyst framework;
(c) determining, by at least one processor of a device, the relative energies of each of the first ground state model structure ($GS^A$), the first transition state model structure ($TS^{A1}$) and a dispersion energy (Disp $E^{A1}$) associated with $TS^{A1}$, and the second transition state model structure ($TS^{A2}$) and a dispersion energy (Disp $E^{A2}$) associated with $TS^{A2}$, and determining values for $\Delta G^{\ddagger A1}$ ($TS^{A1}$–$GS^A$), $\Delta G^{\ddagger A2}$ ($TS^{A2}$–$GS^A$), $\Delta\Delta G^{\ddagger A}$ ($TS^{A2}$–$TS^{A1}$), and an absolute difference in dispersion energies |$\Delta$Disp $E^A$| calculated as $\Delta$(Disp $E^{A2}$–Disp $E^{A1}$)| for migratory insertion of the ethylene molecule versus the α-olefin molecule in the first metallocene catalyst framework;
(d) repeating steps (a)-(c) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ and a dispersion energy (Disp $E^{B1}$) associated with $TS^{B1}$, and $TS^{B2}$ and a dispersion energy (Disp $E^{B2}$) associated with $TS^{B2}$, and determining values for $\Delta G^{\ddagger B1}$ ($TS^{B1}$–$GS^B$), $\Delta G^{\ddagger B2}$ ($TS^{B2}$–$GS^B$), $\Delta\Delta G^{\ddagger B}$ ($TS^{B2}$–$TS^{B1}$), and an absolute difference in dispersion energies |$\Delta$Disp $E^B$| calculated as |$\Delta$(Disp $E^{B2}$–Disp $E^{B1}$)| for migratory insertion of the ethylene molecule versus the α-olefin molecule in the second metallocene catalyst framework; and
(e) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B} < \Delta\Delta G^{\ddagger A}$, when |$\Delta$Disp $E^B$|>|$\Delta$Disp $E^A$|, or a combination thereof, or (2) enhancing ethylene incorporation into a polyethylene co-polymer relative to the first metallocene catalyst framework when $\Delta\Delta G^{\ddagger B} > \Delta\Delta G^{\ddagger A}$, when |$\Delta$Disp $E^B$|<|$\Delta$Disp $E^A$|, or a combination thereof.

Aspect 2. The method for designing a Group 4 metallocene olefin polymerization catalyst according to Aspect 1, further comprising the steps of:
(f) repeating steps (a)-(c) using a third metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, the relative energies of each of a $GS^C$, $TS^{C1}$ and a dispersion energy (Disp $E^{C1}$) associated with $TS^{C1}$, and $TS^{C2}$ and a dispersion energy (Disp $E^{C2}$) associated with $TS^{C2}$, and determining values for $\Delta G^{\ddagger C1}$ ($TS^{C1}$–$GS^C$), $\Delta G^{\ddagger C2}$ ($TS^{C2}$–$GS^C$), $\Delta\Delta G^{\ddagger C}$ ($TS^{C2}$–$TS^{C1}$), and an absolute difference in dispersion energies $\Delta$Disp $E^C$| calculated as |$\Delta$(Disp $E^C_2$–Disp $E^{C1}$)| for migratory insertion of the ethylene molecule versus the α-olefin molecule in the third metallocene catalyst framework; and (g) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C} < \Delta\Delta G^{\ddagger A}$, when $|\Delta\text{Disp } E^C| > \Delta\text{Disp } E^A|$, or a combination thereof, (2) enhancing ethylene incorporation into a polyethylene co-polymer relative to the first metallocene catalyst framework when $\Delta\Delta G^{\ddagger C} > \Delta\Delta G^{\ddagger A}$, when $|\Delta\text{Disp } E^C| < |\Delta\text{Disp } E^A|$, or a combination thereof, (3) enhancing α-olefin co-monomer incorporation into a polyethylene co-polymer relative to the second metallocene catalyst framework when $\Delta\Delta G^{\ddagger C} < \Delta\Delta G^{\ddagger B}$, when $|\Delta\text{Disp } E^C| > \Delta\text{Disp } E^B|$, or a combination thereof, or (4) enhancing ethylene incorporation into a polyethylene co-polymer relative to the second metallocene catalyst framework when $\Delta\Delta G^{\ddagger C} > \Delta\Delta G^{\ddagger B}$, when $|\Delta\text{Disp } E^C| < |\Delta\text{Disp } E^B|$, or a combination thereof.

Aspect 3. A method for designing a Group 4 metallocene olefin polymerization catalyst, the method comprising:

(a) selecting a first metallocene catalyst framework comprising a Group 4 metal bonded to a hydrocarbyl ligand and to one or two independently selected substituted or unsubstituted η$^5$-cycloalkadienyl ligands, and generating a first ground state model structure ($GS^A$) derived from the first metallocene catalyst framework;

(b) generating (1) a first transition state model structure ($TS^{A1}$) derived from the migratory insertion of an ethylene molecule into the metal-hydrocarbyl ligand bond of the first metallocene catalyst framework and (2) a second transition state model structure ($TS^{A2}$) derived from the migratory insertion of an α-olefin co-monomer molecule into the metal-hydrocarbyl ligand bond of the first metallocene catalyst framework;

(c) determining, by at least one processor of a device, the relative energies of each of the first ground state model structure ($GS^A$), the first transition state model structure ($TS^A$) including a dispersion energy (Disp $E^{A1}$) associated with $TS^{A1}$, and the second transition state model structure ($TS^{A2}$) including a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A2}-GS^A$), and $\Delta\Delta G^{\ddagger A}$ ($TS^{A2}-TS^{A1}$) for migratory insertion of the ethylene molecule versus the α-olefin molecule in the first metallocene catalyst framework;

(d) determining, by at least one processor of a device, the number of stabilizing, non-covalent (dispersion-type) interactions (NCI) within a distance of from 2.5 Å to 4.0 Å, inclusive, between (1) the ethylene molecule and the substituted or unsubstituted η$^5$-cycloalkadienyl ligands in the first transition state model structure $TS^{A1}$ ($NCI^{A1}$), and (2) the α-olefin molecule and the substituted or unsubstituted η$^5$-cycloalkadienyl ligands in the second transition state model structure $TS^{A2}$ ($NCI^{A2}$), and difference between the number of these NCI interactions ($\Delta NCI^A$);

(e) repeating steps (a)-(d) using a second metallocene catalyst framework comprising the Group 4 metal bonded to the hydrocarbyl ligand and to the one or two independently selected η$^5$-cycloalkadienyl ligands, wherein at least one of the η$^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, the relative energies of each of a $GS^B$, $TS^{B1}$ including a dispersion energy (Disp $E^{B1}$) associated with $TS^{B1}$, $TS^{B2}$ including a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta\Delta G^{\ddagger B}$ ($TS^{B2}-TS^{B1}$), and the number of stabilizing, non-covalent (dispersion-type) interactions in $TS^{B1}$ ($NCI^{B1}$) and $TS^{B2}$ ($NCI^{B2}$), and difference between the numbers of these NCI interactions ($\Delta NCI^B$), for migratory insertion of the ethylene molecule versus the α-olefin molecule in the second metallocene catalyst framework; and (f) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B} < \Delta\Delta G^{\ddagger A}$, when $\Delta NCI^B > \Delta NCI^A$, or a combination thereof, or (2) enhancing ethylene incorporation into a polyethylene co-polymer relative to the first metallocene catalyst framework when $\Delta\Delta G^{\ddagger B} > \Delta\Delta G^{\ddagger A}$, when $\Delta NCI^B < \Delta NCI^A$, or a combination thereof.

Aspect 4. The method for designing a Group 4 metallocene olefin polymerization catalyst according to Aspect 3, further comprising the steps of:

(g) repeating steps (a)-(d) using a third metallocene catalyst framework comprising the Group 4 metal bonded to the hydrocarbyl ligand and to the one or two independently selected η$^5$-cycloalkadienyl ligands, wherein at least one of the η$^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, the relative energies of each of a $GS^C$, $TS^{C1}$ including a dispersion energy (Disp $E^{C1}$) associated with $TS^{C1}$, and $TS^{C2}$ including a dispersion energy (Disp $E^{C2}$) associated with $TS^{C2}$, and determining values for $\Delta G^{\ddagger C1}$ ($TS^{C1}-GS^C$), $\Delta G^{\ddagger C2}$ ($TS^{C2}-GS^C$), $\Delta\Delta G^{\ddagger C}$ ($TS^{C2}-TS^{C1}$), and the number of stabilizing, non-covalent (dispersion-type) interactions in $TS^{C1}$ ($NCI^{C1}$) and $TS^{C2}$ ($NCI^{C2}$), and difference between the numbers of these NCI interactions ($\Delta NCI^C$), for migratory insertion of the ethylene molecule versus the α-olefin molecule in the second metallocene catalyst framework; and (h) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C} < \Delta\Delta G^{\ddagger A}$, when $\Delta NCI^C > \Delta NCI^A$, or a combination thereof, (2) enhancing ethylene incorporation into a polyethylene co-polymer relative to the first metallocene catalyst framework when $\Delta\Delta G^{\ddagger C} > \Delta\Delta G^{\ddagger A}$, when $\Delta NCI^C < \Delta NCI^A$ or a combination thereof, (3) enhancing α-olefin co-monomer incorporation into a polyethylene co-polymer relative to the second metallocene catalyst framework when $\Delta\Delta G^{\ddagger C} < \Delta\Delta G^{\ddagger B}$, when $\Delta NCI^C > \Delta NCI^B$, or a combination thereof, or (4) enhancing ethylene incorporation into a polyethylene co-polymer relative to the second metallocene catalyst framework when $\Delta\Delta G^{\ddagger C} > \Delta\Delta G^{\ddagger B}$, when $\Delta NCI^C < \Delta NCI^B$, or a combination thereof.

Aspect 5. The method for designing a Group 4 metallocene olefin polymerization catalyst according to any one of Aspects 3-4, wherein the number of non-covalent (dispersion-type) interactions $NCI^A$, $NCI^B$, and $NCI^C$ within a distance of from 2.5 Å to 4.0 Å comprises the number of CH—H, CH—X (X=F, Cl, Br, N, O), and CH-π interactions between the ethylene molecule or the α-olefin molecule and the substituted or unsubstituted $\eta^5$-cycloalkadienyl ligands and the first test substituent of the first metallocene catalyst framework or second metallocene catalyst framework within a distance range of 2.5 to 4.0 Å.

Aspect 6. The method for designing a Group 4 metallocene olefin polymerization catalyst according to any one of the preceding Aspects, wherein:
the first test substituent of the second metallocene catalyst framework is identified as enhancing α-olefin co-monomer incorporation or enhancing ethylene incorporation into the polyethylene co-polymer based upon the relative energies of $\Delta\Delta G^{\ddagger A}$ and $\Delta\Delta G^{\ddagger B}$; or
the second test substituent of the third metallocene catalyst framework is identified as enhancing α-olefin co-monomer incorporation or enhancing ethylene incorporation into the polyethylene co-polymer based upon the relative energies of two of $\Delta\Delta G^{\ddagger A}$, $\Delta\Delta G^{\ddagger B}$, and $\Delta\Delta G^{\ddagger C}$.

Aspect 7. The method for designing a Group 4 metallocene olefin polymerization catalyst according to any of Aspects 1-2, wherein:
the first test substituent of the second metallocene catalyst framework is identified as enhancing α-olefin co-monomer incorporation or enhancing ethylene incorporation into the polyethylene co-polymer based upon the relative energies of $|\Delta \text{Disp } E^A|$ and $|\Delta \text{Disp } E^B|$; or
the second test substituent of the third metallocene catalyst framework is identified as enhancing α-olefin co-monomer incorporation or enhancing ethylene incorporation into the polyethylene co-polymer based upon the relative energies of two of $|\Delta \text{Disp } E^A|$, $|\Delta \text{Disp } E^B|$ and $|\Delta \text{Disp } E^C|$.

Aspect 8. The method for designing a Group 4 metallocene olefin polymerization catalyst according to any of Aspects 3-5, wherein:
the first test substituent of the second metallocene catalyst framework is identified as enhancing α-olefin co-monomer incorporation or enhancing ethylene incorporation into the polyethylene co-polymer based upon $\Delta NCI^A$ and $\Delta NCI^B$; or
the second test substituent of the third metallocene catalyst framework is identified as enhancing α-olefin co-monomer incorporation or enhancing ethylene incorporation into the polyethylene co-polymer based upon $\Delta NCI^A$, $\Delta NCI^B$, and $\Delta NCI^C$.

Aspect 9. The method for designing a Group 4 metallocene olefin polymerization catalyst according to any one of the preceding Aspects, wherein the energies of any one or more of the ground state model structures ($GS^A$, $GS^B$, $GS^C$) and any one or more of the transition state model structures ($TS^{A1}$, $TS^{A2}$, $TS^{B1}$, $TS^{B2}$, $TS^{C1}$, $TS^{C2}$) is calculated as a B3LYP single point energy calculation with a D3BJ correction (B3LYP+D3BJ) using a density functional theory (DFT).

Aspect 10. The method for designing a Group 4 metallocene olefin polymerization catalyst according to any one of Aspects 1-2, 7, or 9, wherein the any one or more of the dispersion energies (Disp $E^A$, Disp $E^B$, Disp $E^C$) is calculated as the difference between a B3LYP single point energy calculation with and without a D3BJ correction using a density functional theory (DFT).

Aspect 11. The method for designing a Group 4 metallocene olefin polymerization catalyst according to any one of Aspects 3-5 or 8-9, wherein the any of the number of stabilizing, non-covalent (dispersion-type) interactions ($NCI^{A1}$, $NCI^{A2}$, $NCI^{B1}$, $NCI^{B2}$, $NCI^{C1}$, $NCI^{C2}$) are calculated using absolutely localized molecular orbital energy decomposition analysis (ALMO-EDA) of the respective transition state model structures ($TS^{A1}$, $TS^{A2}$, $TS^{B1}$, $TS^{B2}$, $TS^{C1}$, and $TS^{C2}$).

Aspect 12. The method for designing a Group 4 metallocene olefin polymerization catalyst according to any one of the preceding Aspects, wherein the first test substituent or the second test substituent is selected from: a halide (F, Cl, or Br); a $C_1$-$C_{10}$ heterohydrocarbyl group comprising a heteroatom selected from halide (F, Cl, or Br), N, O, P, or S; a $C_1$-$C_{10}$ aliphatic group; or a $C_6$-$C_{10}$ aromatic group.

Aspect 13. The method for designing a Group 4 metallocene olefin polymerization catalyst according to any one of the preceding Aspects, wherein the first test substituent or the second test substituent is selected from F, Cl, Br, substituted or unsubstituted $C_1$-$C_6$ alkyl, substituted or unsubstituted $C_6$-$C_{10}$ aryl, $C_1$-$C_6$ alkoxide, —OC(O)$R^1$, —CH$_2$C(O)$R^1$, —NR$^{12}$, —PH$_3$, PR$^{13}$, or —SR$^1$, wherein $R^1$ is independently selected from a $C_1$-$C_6$ alkyl or a $C_6$-$C_{10}$ aryl.

Aspect 14. The method for designing a Group 4 metallocene olefin polymerization catalyst according to any one of the preceding Aspects, wherein the first test substituent or the second test substituent is selected from F, Cl, Br, —CH$_3$, —CMe$_3$, —C(CH$_2$)$_3$CH, —CF$_3$, —OMe, —OC(O)Me, —CH$_2$C(O)Me, —OC$_6$H$_{11}$, —OPh, —NMe$_2$, —N(C$_6$H$_{11}$)$_2$, PH$_3$, PMe$_3$, —SC$_6$H$_{11}$, or —SPh.

Aspect 15. The method for designing a Group 4 metallocene olefin polymerization catalyst according to any one of the preceding Aspects, wherein the first metallocene catalyst framework comprises Ti, alternatively Zr, or alternatively Hf.

Aspect 16. The method for designing a Group 4 metallocene olefin polymerization catalyst according to any one of the preceding Aspects, wherein the hydrocarbyl ligand is a $C_1$-$C_6$ hydrocarbyl ligand, or alternatively a $C_1$-$C_4$ hydrocarbyl ligand, or alternatively an ethyl ($C_2$) ligand.

Aspect 17. The method for designing a Group 4 metallocene olefin polymerization catalyst according to any one of the preceding Aspects, wherein the α-olefin co-monomer comprises or is selected from propylene, 1-butene, 1-pentene, 1-hexene, 1-heptene, 1-octene, or styrene.

Aspect 18. The method for designing a Group 4 metallocene olefin polymerization catalyst according to any one of the preceding Aspects, wherein the substituted or unsubstituted $\eta^5$-cycloalkadienyl ligands are selected independently from cyclopentadienyl, indenyl, or fluorenyl.

Aspect 19. The method for designing a Group 4 metallocene olefin polymerization catalyst according to any one of the preceding Aspects, wherein the substituted or unsubstituted $\eta^5$-cycloalkadienyl ligands, absent the first test substituent and absent the second test substituent, are selected independently from cyclopentadienyl, methylcyclopentadienyl, t-butyl-cyclopentadienyl, indenyl, 4-phenyl-indenyl, 2-methylindenyl, 3-t-butylindenyl, 2-methyl-4-phenylindenyl, fluorenyl, or 2-methylfluorenyl.

Aspect 20. The method for designing a Group 4 metallocene olefin polymerization catalyst according to any one of the preceding Aspects, wherein the first metallocene catalyst framework comprises two independently selected substituted or unsubstituted $\eta^5$-cycloalkadienyl ligands.

Aspect 21. The method for designing a Group 4 metallocene olefin polymerization catalyst according to any one of the preceding Aspects, wherein the first metallocene catalyst framework comprises two independently selected substituted or unsubstituted $\eta^5$-cycloalkadienyl ligands which are bridged by a linking group of the formula (1) >ER$^1$R$^2$, wherein E is C or Si, R$^1$ is hydrogen or a $C_1$-$C_{12}$ hydrocarbyl group, and R$^2$ is hydrogen, a $C_1$-$C_{12}$ hydrocarbyl group, or a $C_3$-$C_{10}$ alkenyl group having a terminal C=C double bond, or (2) CR$^{12}$CR$^2$—, wherein R$^1$ and R$^2$ are selected independently from hydrogen or a $C_1$-$C_6$ hydrocarbyl group.

Aspect 22. The method for designing a Group 4 metallocene olefin polymerization catalyst according to any one of the preceding Aspects, wherein the first metallocene catalyst framework comprises two independently selected substituted or unsubstituted $\eta^5$-cycloalkadienyl ligands which are bridged by a linking group of the formula >CMe$_2$, —CH$_2$CH$_2$, >SiMe$_2$, or >CH[(CH$_2$)$_2$CH=CH$_2$].

Aspect 23. The method for designing a Group 4 metallocene olefin polymerization catalyst according to any one of the preceding Aspects, wherein the first metallocene catalyst framework comprises one of the following structures:

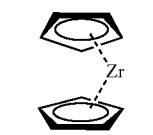

1

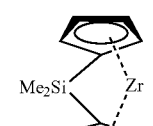

2

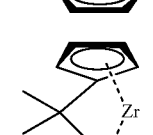

3

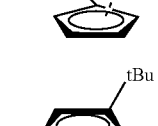

4

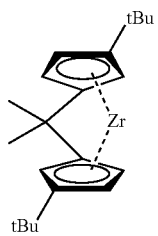

5

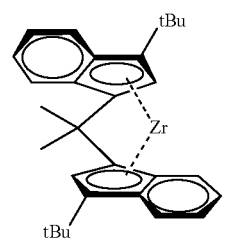

6

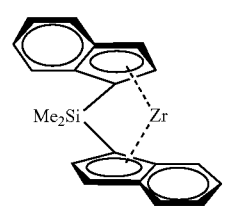

7

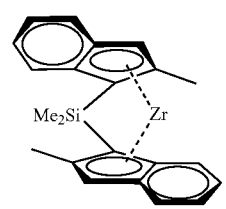

8

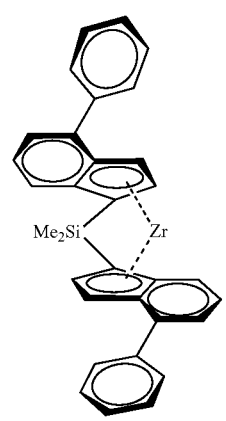

9

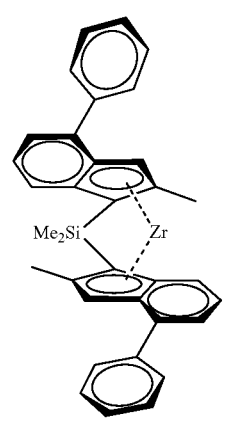

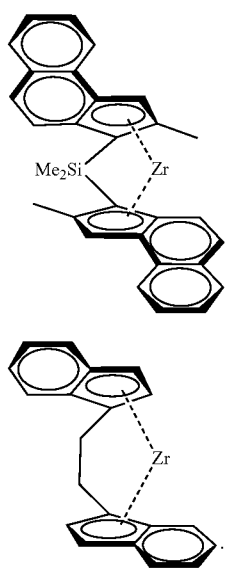

Aspect 24. The method for designing a Group 4 metallocene olefin polymerization catalyst according to any one of the preceding Aspects, wherein the first metallocene catalyst framework comprises one substituted or unsubstituted $\eta^5$-cycloalkadienyl ligand and further comprises an anionic ligand.

Aspect 25. The method for designing a Group 4 metallocene olefin polymerization catalyst according to any one of the preceding Aspects, wherein the first metallocene catalyst framework comprises one substituted or unsubstituted $\eta^5$-cycloalkadienyl ligand and further comprises an anionic ligand selected from halide, hydride, a $C_1$-$C_{20}$ hydrocarbyl group, a $C_1$-$C_{20}$ heterohydrocarbyl group, tetrahydroborate, or $OBR^{42}$ or $OSO_2R^A$ wherein $R^A$ is independently a $C_1$-$C_{12}$ hydrocarbyl group.

Aspect 26. The method for designing a Group 4 metallocene olefin polymerization catalyst according to any one of the preceding Aspects, wherein the first metallocene catalyst framework comprises one substituted or unsubstituted $\eta^5$-cycloalkadienyl ligand and further comprises an anionic ligand selected from F, Cl, Br, a hydride, a $C_1$-$C_{12}$ hydrocarbyl group, a $C_1$-$C_{12}$ hydrocarbyloxide group, a $C_1$-$C_{12}$ hydrocarbylamino group, $C_1$-$C_{12}$ dihydrocarbylamino, or a trihydrocarbylsilyl group wherein each hydrocarbyl is independently a $C_1$-$C_{12}$ hydrocarbyl group.

Aspect 27. The method for designing a Group 4 metallocene olefin polymerization catalyst according to any one of the preceding Aspects, further comprising the step of synthesizing the Group 4 metallocene catalyst comprising the one or two independently selected $\eta^5$-cycloalkadienyl ligands, wherein at least one of the $\eta^5$-cycloalkadienyl ligands comprises the first test substituent or the second test substituent.

Aspect 28. The method for designing a Group 4 metallocene olefin polymerization catalyst according to any one of the preceding Aspects, further comprising the steps of: providing a Group 4 metallocene catalyst comprising the one or two independently selected $\eta^5$-cycloalkadienyl ligands, wherein at least one of the $\eta^5$-cycloalkadienyl ligands comprises the first test substituent or the second test substituent; and contacting the Group 4 metallocene catalyst with ethylene and an α-olefin co-monomer molecule under polymerization conditions to form a polyethylene co-polymer.

Aspect 29. A catalyst system for polymerizing olefins, the catalyst system comprising: a zirconocene catalyst comprising two $\eta^5$-cycloalkadienyl ligands independently selected from a substituted or an unsubstituted $\eta^5$-cyclopentadienyl ligand or a substituted or an unsubstituted $\eta^5$-indenyl ligand, wherein the two $\eta^5$-cycloalkadienyl ligands are optionally bridged by a linking group; and one of the $\eta^5$-cycloalkadienyl ligands is substituted with at least one substituent which imparts enhanced dispersion-type interactions in a transition state for a migratory insertion of an α-olefin co-monomer molecule into a metal-hydrocarbyl ligand bond of the zirconocene catalyst versus a migratory insertion of the α-olefin co-monomer molecule into a metal-hydrocarbyl ligand bond of a zirconocene catalyst comprising the corresponding unsubstituted $\eta^5$-cycloalkadienyl ligands.

Aspect 30. A catalyst system for polymerizing olefins, the catalyst system comprising: a zirconocene catalyst comprising two $\eta^5$-cycloalkadienyl ligands independently selected from a substituted or an unsubstituted $\eta^5$-cyclopentadienyl ligand or a substituted or an unsubstituted $\eta^5$-indenyl ligand, wherein the two $\eta^5$-cycloalkadienyl ligands are optionally bridged by a linking group; and one of the $\eta^5$-cycloalkadienyl ligands is substituted with at least one substituent which imparts enhanced number of stabilizing, non-covalent (dispersion-type) interactions (NCI) within a distance of from 2.5 Å to 4.0 Å, inclusive, between the α-olefin molecule and the at least one substituent in a transition state for a migratory insertion of an α-olefin co-monomer molecule into a metal-hydrocarbyl ligand bond of the zirconocene catalyst versus a migratory insertion of the α-olefin co-monomer molecule into a metal-hydrocarbyl ligand bond of a zirconocene catalyst comprising the corresponding unsubstituted $\eta^5$-cycloalkadienyl ligands.

Aspect 31. The catalyst system for polymerizing olefins according to one of Aspects 29-30, wherein the zirconocene catalyst comprises one of the following structures:

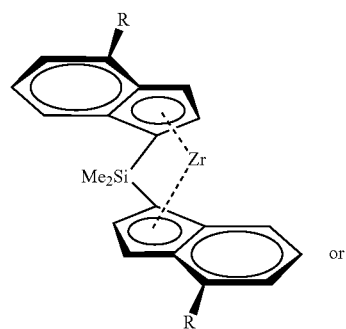

or

-continued

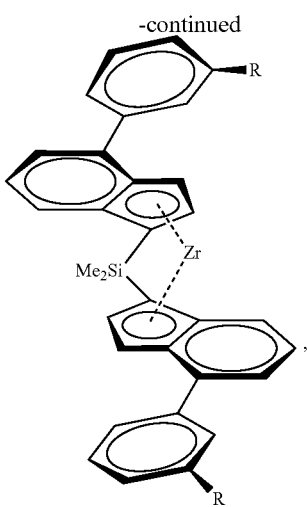

wherein:
R is selected independently from F, Cl, Br, $C_1$-$C_6$ alkyl, $C_6$-$C_{10}$ aryl, $C_1$-$C_6$ alkoxide, —OC(O)$R^1$, —CH$_2$C(O)$R^1$, —NR$^{12}$, —PH$_3$, PR$^{13}$, or —SR$^1$, and wherein $R^1$ is independently selected from a $C_1$-$C_6$ alkyl or a $C_6$-$C_{10}$ aryl, in the substituted $\eta^5$-cycloalkadienyl ligands; and
R is H in the corresponding unsubstituted $\eta^5$-cycloalkadienyl ligands.

Aspect 32. The catalyst system for polymerizing olefins according to Aspect 31, wherein R is selected independently from F, Cl, Br, —CH$_3$, —CMe$_3$, —C(CH$_2$)$_3$CH, —CF$_3$, —OMe, —OC(O)Me, —CH$_2$C(O)Me, —OC$_6$H$_{11}$, —OPh, —NMe$_2$, —N(C$_6$H$_{11}$)$_2$, PH$_3$, PMe$_3$, —SC$_6$H$_{11}$, or —SPh, in the substituted $\eta^5$-cycloalkadienyl ligands.

Aspect 33. A catalyst system for polymerizing olefins, comprising:
the Group 4 metallocene olefin polymerization catalyst comprising the Group 4 metal bonded to the hydrocarbyl ligand and to the one or two independently selected substituted or unsubstituted $\eta^5$-cycloalkadienyl ligands, according to any one of Aspects 1-28; and
wherein at least one of the $\eta^5$-cycloalkadienyl ligands comprises the first test substituent.

Aspect 34. The catalyst system for polymerizing olefins according to Aspect 33, wherein the first test substituent is identified as enhancing α-olefin co-monomer incorporation into a polyethylene co-polymer, relative to an α-olefin co-monomer incorporation of the first metallocene catalyst framework.

Aspect 35. A catalyst system for polymerizing olefins, comprising:
the Group 4 metallocene olefin polymerization catalyst comprises the Group 4 metal bonded to the hydrocarbyl ligand and to the one or two independently selected substituted or unsubstituted $\eta^5$-cycloalkadienyl ligands, according to any of Aspects 2 and 4-28; and
wherein at least one of the $\eta^5$-cycloalkadienyl ligands comprises the second test substituent.

Aspect 36. The catalyst system for polymerizing olefins according to Aspect 35, wherein the second test substituent is identified as enhancing α-olefin co-monomer incorporation into a polyethylene co-polymer, relative to an α-olefin co-monomer incorporation of the first metallocene catalyst framework.

Aspect 37. A catalyst system for polymerizing olefins according to any one of Aspects 33-36, wherein the catalyst system further comprises:
(a) an activator comprising a solid oxide treated with an electron-withdrawing anion (activator-support), an organoboron compound, an organoborate compound, an ionizing ionic compound, an aluminoxane compound, or any combination thereof; and
(b) optionally, a co-catalyst comprising an organoaluminum compound, an organoboron compound, an organozinc compound, an organomagnesium compound, an organolithium compound, or any combination thereof.

Aspect 38. The catalyst system for polymerizing olefins according to Aspect 37, wherein the activator comprises a solid oxide treated with an electron-withdrawing anion, and wherein: the solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, boehmite, heteropolytungstates, mixed oxides thereof, or any combination thereof; and
the electron-withdrawing anion comprises fluoride, chloride, bromide, iodide, sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, trifluoroacetate, fluoroborate, fluorozirconate, fluorotitanate, or any combination thereof.

Aspect 39. The catalyst system for polymerizing olefins according to Aspect 38, wherein:
the solid oxide comprises alumina, silica-alumina, silica-coated alumina, or a mixture thereof, and
the electron-withdrawing anion comprises fluoride, sulfate, or phosphate.

Aspect 40. The catalyst system for polymerizing olefins according to Aspect 37, wherein the activator comprises fluorided alumina, fluorided silica, fluorided silica-alumina, or fluorided silica-coated alumina (mullite).

Aspect 41. The catalyst system for polymerizing olefins according to any one of Aspects 37-40, wherein the co-catalyst is present and comprises trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

REFERENCES

The following references and any Supporting Information accompanying the following references may provide background information or other useful information related to the various aspects or embodiments of this disclosure. These references and any accompanying Supporting Information are incorporated herein by reference in their entireties.

REFERENCES (1) Ahn, S.; Hong, M.; Sundararajan, M.; Ess, D. H.; Baik, M.-H. Design and Optimization of Catalysts Based on Mechanistic Insights Derived from Quantum Chemical Reaction Modeling. Chem. Rev. 2019, 119, 6509-6560. https://doi.org/10.1021/acs.chemrev.9b00073.

(2) Poater, A.; Falivene, L.; Cavallo, L. Theoretical Attempts: "In Silico Olefin Metathesis"-How Can Computers Help in the Understanding of Metathesis Mechanisms and in Catalysts Development? Olefin Metathesis Theory Pract. 2014, 483-494. https://doi.org/10.1002/9781118711613.ch19.

(3) Ess, D. H.; Gagliardi, L.; Hammes-Schiffer, S. Introduction: Computational Design of Catalysts from Molecules to Materials. Chem. Rev. 2019, 119, 6507-6508.

(4) Durand, D. J.; Fey, N. Computational Ligand Descriptors for Catalyst Design. Chem. Rev. 2019, 119, 6561-6594.

(5) Reid, J. P.; Sigman, M. S. Comparing Quantitative Prediction Methods for the Discovery of Small-Molecule Chiral Catalysts. Nat. Rev. Chem. 2018, 2 (10), 290-305. https://doi.org/10.1038/s41570-018-0040-8.

(6) Ahneman, D. T.; Estrada, J. G.; Lin, S.; Dreher, S. D.; Doyle, A. G. Predicting Reaction Performance in C—N Cross-Coupling Using Machine Learning. Science (80-.). 2018, 360, 186-190.

(7) Nielsen, M. K.; Ahneman, D. T.; Riera, O.; Doyle, A. G. Deoxyfluorination with Sulfonyl Fluorides: Navigating Reaction Space with Machine Learning. J. Am. Chem. Soc. 2018, 140 (15), 5004-5008. https://doi.org/10.1021/jacs.8b01523.

(8) Aires-de-Sousa, J.; Gasteiger, J. Prediction of Enantiomeric Excess in a Combinatorial Library of Catalytic Enantioselective Reactions. J. Comb. Chem. 2005, 7 (2), 298-301. https://doi.org/10.1021/cc049961q.

(9) Wang, Y.; Wang, J.; Su, J.; Huang, F.; Jiao, L.; Liang, Y.; Yang, D.; Zhang, S.; Wender, P. A.; Yu, Z. X. A Computationally Designed Rh(I)-Catalyzed Two-Component [5+2+1] Cycloaddition of Ene-Vinylcyclopropanes and CO for the Synthesis of Cyclooctenones. J. Am. Chem. Soc. 2007, 129 (33), 10060-10061. https://doi.org/10.1021/ja072505w.

(10) Donoghue, P. J.; Helquist, P.; Norrby, P. O.; Wiest, O. Prediction of Enantioselectivity in Rhodium Catalyzed Hydrogenations. J. Am. Chem. Soc. 2009, 131 (2), 410-411. https://doi.org/10.1021/ja806246h.

(11) Rowley, C. N.; Woo, T. K. Computational Design of Ruthenium Hydride Olefin-Hydrogenation Catalysts Containing Hemilabile Ligands1,2. Can. J. Chem. 2009, 87 (7), 1030-1038. https://doi.org/10.1139/V09-077.

(12) Baik, M. H.; Mazumder, S.; Ricci, P.; Sawyer, J. R.; Song, Y. G.; Wang, H.; Evans, P. A. Computationally Designed and Experimentally Confirmed Diastereoselective Rhodium-Catalyzed Pauson-Khand Reaction at Room Temperature. J. Am. Chem. Soc. 2011, 133 (20), 7621-7623. https://doi.org/10.1021/ja107895g.

(13) Fernandez, L. E.; Horvath, S.; Hammes-Schiffer, S. Theoretical Design of Molecular Electrocatalysts with Flexible Pendant Amines for Hydrogen Production and Oxidation. J. Phys. Chem. Lett. 2013, 4 (3), 542-546. https://doi.org/10.1021/jz3020277.

(14) Nielsen, M. C.; Bonney, K. J.; Schoenebeck, F. Computational Ligand Design for the Reductive Elimination of ArCF3 from a Small Bite Angle PdII Complex: Remarkable Effect of a Perfluoroalkyl Phosphine. Angew. Chemie—Int. Ed. 2014, 53 (23), 5903-5906. https://doi.org/10.1002/anie.201400837.

(15) Bernales, V.; League, A. B.; Li, Z.; Schweitzer, N. M.; Peters, A. W.; Carlson, R. K.; Hupp, J. T.; Cramer, C. J.; Farha, O. K.; Gagliardi, L. Computationally Guided Discovery of a Catalytic Cobalt-Decorated Metal-Organic Framework for Ethylene Dimerization. J. Phys. Chem. C 2016, 120 (41), 23576-23583. https://doi.org/10.1021/acs.jpcc.6b07362.

(16) Kwon, D. H.; Fuller, J. T.; Kilgore, U. J.; Sydora, O. L.; Bischof, S. M.; Ess, D. H. Computational Transition-State Design Provides Experimentally Verified Cr(P,N) Catalysts for Control of Ethylene Trimerization and Tetramerization. ACS Catal. 2018, 8 (2), 1138-1142. https://doi.org/10.1021/acscatal.7b04026.

(17) Dobbin, C. An Industrial Chronology of Polyethylene. In Handbook of Industrial Polyethylene Technology; Spalding, M. A., Chatterjee, A. M., Eds.; Scrivener Publishing: Hoboken, NJ, USA, 2017; pp 3-24.

(18) Alt, H. G.; Köppl, A. Effect of the Nature of Metallocene Complexes of Group IV Metals on Their Performance in Catalytic Ethylene and Propylene Polymerization. Chem. Rev. 2000, 100 (4), 1205-1221. https://doi.org/10.1021/cr9804700.

(19) Kollman, P. A. Noncovalent Interactions. Acc. Chem. Res. 1977, 10 (10), 365-371. https://doi.org/10.1021/ar50118a003.

(20) Müller-Dethlefs, K.; Hobza, P. Noncovalent Interactions: A Challenge for Experiment and Theory. Chem. Rev. 2000, 100 (1), 143-167. https://doi.org/10.1021/cr9900331.

(21) Mahadevi, A. S.; Sastry, G. N. Cooperativity in Noncovalent Interactions. Chem. Rev. 2016, 116 (5), 2775-2825. https://doi.org/10.1021/cr500344e.

(22) Grimme, S. Density Functional Theory with London Dispersion Corrections. Wiley Interdiscip. Rev. Comput. Mol. Sci. 2011, 1 (2), 211-228. https://doi.org/10.1002/wcms.30.

(23) Bursch, M.; Caldeweyher, E.; Hansen, A.; Neugebauer, H.; Ehlert, S.; Grimme, S. Understanding and Quantifying London Dispersion Effects in Organometallic Complexes. Acc. Chem. Res. 2019, 52 (1), 258-266. https://doi.org/10.1021/acs.accounts.8b00505.

(24) Mahmudov, K. T.; Gurbanov, A. V.; Guseinov, F. I.; Guedes da Silva, M. F. C. Noncovalent Interactions in Metal Complex Catalysis. Coord. Chem. Rev. 2019, 387, 32-46. https://doi.org/10.1016/j.ccr.2019.02.011.

(25) Zaccaria, F.; Ehm, C.; Budzelaar, P. H. M.; Busico, V. Accurate Prediction of Copolymerization Statistics in Molecular Olefin Polymerization Catalysis: The Role of Entropic, Electronic, and Steric Effects in Catalyst Comonomer Affinity. ACS Catal. 2017, 7 (2), 1512-1519. https://doi.org/10.1021/acscatal.6b03458.

(26) Friederichs, N.; Wang, B.; Budzelaar, P. H. M.; Coussens, B. B. A Combined Experimental—Molecular Modeling Approach for Ethene-Propene Copolymerization with C2-Symmetric Metallocenes. J. Mol. Catal. A Chem. 2005, 242 (1-2), 91-104. https://doi.org/10.1016/j.molcata.2005.06.066.

(27) Zambelli, A.; Grassi, A.; Galimberti, M.; Mazzochi, R.; Piemontesi, F. Copolymerization of Ethylene with Propene in the Presence of Homogeneous Catalytic-Systems Based on Group-4 Metallocenes and Methylalumoxane—Implications of the Reactivity Ratios on the Reaction-Mechanism. Makromol. Chemie—Rapid Commun. 1991, 12 (8), 523-528.

(28) Galimberti, M.; Piemontesi, F.; Mascellani, N.; Camurati, I.; Fusco, O.; Destro, M. Metallocenes for Ethene/Propene Copolymerizations with High Product of Reactivity Ratios. Macromolecules 1999, 32 (24), 7968-7976. https://doi.org/10.1021/ma981961p.

(29) Galimberti, M.; Piemontesi, F.; Fusco, O.; Camurati, I.; Destro, M. Ethene/Propene Copolymerization with High Product of Reactivity Ratios from a Single Center, Metallocene-Based Catalytic System. Macromolecules 1998, 31 (11), 3409-3416. https://doi.org/10.1021/ma9717247.

(30) Kumar, M.; Chaudhari, R. V.; Subramaniam, B.; Jackson, T. A. Ligand Effects on the Regioselectivity of Rhodium-Catalyzed Hydroformylation: Density Functional Calculations Illuminate the Role of Long-Range Noncovalent Interactions. Organometallics 2014, 33 (16), 4183-4191. https://doi.org/10.1021/om500196g.

(31) Johnson, E. R.; Keinan, S.; Mori Sánchez, P.; Contreras García, J.; Cohen, A. J.; Yang, W. NCI: Revealing Non-Covalent Interactions. J. Am. Chem. Soc. 2010, 132 (18), 6498-6506. https://doi.org/10.1021/ja100936w.

(32) Weymuth, T.; Couzijn, E. P. A.; Chen, P.; Reiher, M. New Benchmark Set of Transition-Metal Coordination Reactions for the Assessment of Density Functionals. J. Chem. Theory Comput. 2014, 10 (8), 3092-3103. https://doi.org/10.1021/ct500248h.

(33) Husch, T.; Freitag, L.; Reiher, M. Calculation of Ligand Dissociation Energies in Large Transition-Metal Complexes. J. Chem. Theory Comput. 2018, 14 (5), 2456-2468. https://doi.org/10.1021/acs.jctc.8b00061.

(34) Jacobsen, H.; Cavallo, L. On the Accuracy of DFT Methods in Reproducing Ligand Substitution Energies for Transition Metal Complexes in Solution: The Role of Dispersive Interactions. ChemPhysChem 2012, 13 (2), 562-569. https://doi.org/10.1002/cphc.201100705.

(35) Grimme, S. Comment on: "On the Accuracy of DFT Methods in Reproducing Ligand Substitution Energies for Transition Metal Complexes in Solution: The Role of Dispersive Interactions" by H. Jacobsen and L. Cavallo. ChemPhysChem 2012, 13 (6), 1407-1409. https://doi.org/10.1002/cphc.201200094.

(36) Jacobsen, H.; Cavallo, L. Reply to the Comment by Grimme on: "On the Accuracy of DFT Methods in Reproducing Ligand Substitution Energies for Transition Metal Complexes in Solution: The Role of Dispersive Interactions." ChemPhysChem 2012, 13 (6), 1405-1406. https://doi.org/10.1002/cphc.201200165.

(37) Rönnholm, P.; Lill, S. O. N.; Gräfenstein, J.; Norrby, P. O.; Pettersson, M.; Hilmersson, G. Aggregation and Solvation of Chiral N, P-Amide Ligands in Coordinating Solvents: A Computational and NMR Spectroscopic Study. Chempluschem 2012, 77 (9), 799-806. https://doi.org/10.1002/cplu.201200033.

(38) McMullin, C. L.; Jover, J.; Harvey, J. N.; Fey, N. Accurate Modelling of Pd(0)+PhX Oxidative Addition Kinetics. Dalt. Trans. 2010, 39 (45), 10833-10836. https://doi.org/10.1039/c0dt00778a.

(39) McMullin, C. L.; Fey, N.; Harvey, J. N. Computed Ligand Effects on the Oxidative Addition of Phenyl Halides to Phosphine Supported Palladium(0) Catalysts. Dalt. Trans. 2014, 43 (36), 13545-13556. https://doi.org/10.1039/c4dt01758g.

(40) Hansen, A.; Bannwarth, C.; Grimme, S.; Petrovic, P.; Werlé, C.; Djukic, J. P. The Thermochemistry of London Dispersion-Driven Transition Metal Reactions: Getting the "Right Answer for the Right Reason." ChemistryOpen 2014, 3 (5), 177-189. https://doi.org/10.1002/open.201402017.

(41) Eisenschitz, R.; London, F. Über Das Verhältnis Der van Der Waalsschen Kräfte Zu Den Homöopolaren Bindungskräften. Zeitschrift fur Phys. 1930, 60, 491-527.

(42) Stone, A. J. The Theory of Intermolecular Forces, 2nd ed.; Oxford University Press, 2013.

(43) Maseras, F.; Eisenstein, O. Opposing Steric and Electronic Contributions in OsCl2H2(PPr3i)2. A Theoretical Study of an Unusual Structure. New J. Chem. 1998, 22 (1), 5-9. https://doi.org/10.1039/a706748h.

(44) Lin, C. Y.; Guo, J. D.; Fettinger, J. C.; Nagase, S.; Grandjean, F.; Long, G. J.; Chilton, N. F.; Power, P. P. Dispersion Force Stabilized Two-Coordinate Transition Metal-Amido Complexes of the —N(SiMe3)Dipp (Dipp=C6H3-2,6-Pr$^i_2$) Ligand: Structural, Spectroscopic, Magnetic, and Computational Studies. Inorg. Chem. 2013, 52 (23), 13584-13593. https://doi.org/10.1021/ic402105m.

(45) Wang, C.; Mo, Y.; Wagner, J. P.; Schreiner, P. R.; Jemmis, E. D.; Danovich, D.; Shaik, S. The Self-Association of Graphane Is Driven by London Dispersion and Enhanced Orbital Interactions. J. Chem. Theory Comput. 2015, 11 (4), 1621-1630. https://doi.org/10.1021/acs.jctc.5b00075.

(46) Wagner, J. P.; Schreiner, P. R. London Dispersion in Molecular Chemistry—Reconsidering Steric Effects. Angew. Chemie—Int. Ed. 2015, 54 (42), 12274-12296. https://doi.org/10.1002/anie.201503476.

(47) Hanninen, M. M.; Pal, K.; Day, B. M.; Pugh, T.; Layfield, R. A. A Three-Coordinate Iron-Silylene Complex Stabilized by Ligand-Ligand Dispersion Forces. Dalt. Trans. 2016, 45 (28), 11301-11305. https://doi.org/10.1039/c6dt02486f.

(48) Liptrot, D. J.; Power, P. P. London Dispersion Forces in Sterically Crowded Inorganic and Organometallic Molecules. Nat. Rev. Chem. 2017, 1. https://doi.org/10.1038/s41570-016-0004.

(49) Rekken, B. D.; Brown, T. M.; Fettinger, J. C.; Lips, F.; Tuononen, H. M.; Herber, R. H.; Power, P. P. Dispersion Forces and Counterintuitive Steric Effects in Main Group Molecules: Heavier Group 14 (Si—Pb) Dichalcogenolate Carbene Analogues with Sub-90 Interligand Bond Angles. J. Am. Chem. Soc. 2013, 135 (27), 10134-10148. https://doi.org/10.1021/ja403802a.

(50) Song, L.; Schoening, J.; Wölper, C.; Schulz, S.; Schreiner, P. R. Role of London Dispersion Interactions in Ga-Substituted Dipnictenes. Organometallics 2019, 38 (7), 1640-1647. https://doi.org/10.1021/acs.organomet.9b00072.

(51) McCrea-Hendrick, M. L.; Bursch, M.; Gullett, K. L.; Maurer, L. R.; Fettinger, J. C.; Grimme, S.; Power, P. P. Counterintuitive Interligand Angles in the Diaryls E{C6H3-2,6-(C6H2-2,4,6-IPr3)2}2 (E=Ge, Sn, or Pb) and Related Species: The Role of London Dispersion Forces. Organometallics 2018, 37 (13), 2075-2085. https://doi.org/10.1021/acs.organomet.8b00225.

(52) Bursch, M.; Caldeweyher, E.; Hansen, A.; Neugebauer, H.; Ehlert, S.; Grimme, S. Understanding and Quantifying London Dispersion Effects in Organometallic Complexes. Acc. Chem. Res. 2019, 52 (1), 258-266. https://doi.org/10.1021/acs.accounts.8b00505.

(53) Rösel, S.; Quanz, H.; Logemann, C.; Becker, J.; Mossou, E.; Cañadillas-Delgado, L.; Caldeweyher, E.; Grimme, S.; Schreiner, P. R. London Dispersion Enables the Shortest Intermolecular Hydrocarbon H . . . H Contact. J. Am. Chem. Soc. 2017, 139 (22), 7428-7431. https://doi.org/10.1021/jacs.7b01879.

(54) Yepes, D.; Neese, F.; List, B.; Bistoni, G. Unveiling the Delicate Balance of Steric and Dispersion Interactions in Organocatalysis Using High-Level Computational Methods. J. Am. Chem. Soc. 2020, 142 (7), 3613-3625. https://doi.org/10.1021/jacs.9b13725.

(55) Freitag, K.; Banh, H.; Gemel, C.; Jerabek, P.; Seidel, R. W.; Frenking, G.; Fischer, R. A. Dizinc Cation [Zn2]2+ Trapped in a Homoleptic Metalloid Coordination Envi-

(56) Pal, R.; Mebs, S.; Shi, M. W.; Jayatilaka, D.; Krzeszczakowska, J. M.; Malaspina, L. A.; Wiecko, M.; Luger, P.; Hesse, M.; Chen, Y. S.; et al. Linear MgCp*2 vs Bent CaCp*2: London Dispersion, Ligand-Induced Charge Localizations, and Pseudo-Pregostic C—H . . . Ca Interactions. Inorg. Chem. 2018, 57 (9), 4906-4920. https://doi.org/10.1021/acs.inorgchem.7b03079.

(57) Martinez, S. H.; Pan, S.; Cabellos, J. L.; Dzib, E.; Fernández-Herrera, M. A.; Merino, G. Importance of Dispersion on the Stability of the Concave-Bound CpM (M=Fe, Ru, Os) Complexes of Sumanene. Organometallics 2017, 36 (10), 2036-2041. https://doi.org/10.1021/acs.organomet.7b00282.

(58) Lin, X.; Wu, W.; Mo, Y. A Theoretical Perspective of the Agostic Effect in Early Transition Metal Compounds. Coord. Chem. Rev. 2020, 419, 213401. https://doi.org/10.1016/j.ccr.2020.213401.

(59) Haaland, A.; Scherer, W.; Ruud, K.; McGrady, G. S.; Downs, A. J.; Swang, O. On the Nature and Incidence of β-Agostic Interactions in Ethyl Derivatives of Early Transition Metals: Ethyltitanium Trichloride and Related Compounds. J. Am. Chem. Soc. 1998, 120 (15), 3762-3772. https://doi.org/10.1021/ja9737578.

(60) Lu, Q.; Neese, F.; Bistoni, G. Formation of Agostic Structures Driven by London Dispersion. Angew. Chemie—Int. Ed. 2018, 57 (17), 4760-4764. https://doi.org/10.1002/anie.201801531.

(61) Lu, Q.; Neese, F.; Bistoni, G. London Dispersion Effects in the Coordination and Activation of Alkanes in σ-Complexes: A Local Energy Decomposition Study. Phys. Chem. Chem. Phys. 2019, 21 (22), 11569-11577. https://doi.org/10.1039/c9c01309a.

(62) Grimme, S.; Djukic, J. P. The Crucial Role of Dispersion in the Cohesion of Nonbridged Binuclear Os→Cr and Os→W Adducts. Inorg. Chem. 2010, 49 (6), 2911-2919. https://doi.org/10.1021/ic9024662.

(63) Biedermann, F.; Schneider, H.-J. Experimental Binding Energies in Supramolecular Complexes. Chem. Rev. 2016, 116 (9), 5216-5300.

(64) Knowles, R. R.; Jacobsen, E. N. Attractive Noncovalent Interactions in Asymmetric Catalysis: Links between Enzymes and Small Molecule Catalysts. Proc. Natl. Acad. Sci. 2010, 107 (48), 20678-20685.

(65) Armstrong, A.; Boto, R. A.; Dingwall, P.; Contreras-García, J.; Harvey, M. J.; Mason, N. J.; Rzepa, H. S. The Houk-List Transition States for Organocatalytic Mechanisms Revisited. Chem. Sci. 2014, 5 (5), 2057-2071. https://doi.org/10.1039/c3sc53416b.

(66) Wheeler, S. E.; Seguin, T. J.; Guan, Y.; Doney, A. C. Noncovalent Interactions in Organocatalysis and the Prospect of Computational Catalyst Design. Ace. Chem. Res. 2016, 49 (5), 1061-1069.

(67) Krenske, E. H.; Houk, K. N. Aromatic Interactions as Control Elements in Stereoselective Organic Reactions. Acc. Chem. Res. 2013, 46 (4), 979-989.

(68) Walden, D. M.; Ogba, O. M.; Johnston, R. C.; Cheong, P. H. Y. Computational Insights into the Central Role of Nonbonding Interactions in Modern Covalent Organocatalysis. Acc. Chem. Res. 2016, 49 (6), 1279-1291. https://doi.org/10.1021/acs.accounts.6b00204.

(69) Toste, F. D.; Sigman, M. S.; Miller, S. J. Pursuit of Noncovalent Interactions for Strategic Site-Selective Catalysis. Acc. Chem. Res. 2017, 50 (3), 609-615. https://doi.org/10.1021/acs.accounts.6b00613.

(70) Neel, A. J.; Hilton, M. J.; Sigman, M. S.; Toste, F. D. Exploiting Non-Covalent R Interactions for Catalyst Design. Nature 2017, 543 (7647), 637-646. https://doi.org/10.1038/nature21701.

(71) Schreiner, P. R.; Chernish, L. V.; Gunchenko, P. A.; Tikhonchuk, E. Y.; Hausmann, H.; Serafin, M.; Schlecht, S.; Dahl, J. E. P.; Carlson, R. M. K.; Fokin, A. A. Overcoming Lability of Extremely Long Alkane Carbon-Carbon Bonds through Dispersion Forces. Nature 2011, 477 (7364), 308-311. https://doi.org/10.1038/nature10367.

(72) Fokin, A. A.; Chernish, L. V.; Gunchenko, P. A.; Tikhonchuk, E. Y.; Hausmann, H.; Serafin, M.; Dahl, J. E. P.; Carlson, R. M. K.; Schreiner, P. R. Stable Alkanes Containing Very Long Carbon-Carbon Bonds. J. Am. Chem. Soc. 2012, 134 (33), 13641-13650. https://doi.org/10.1021/ja302258q.

(73) Grimme, S.; Schreiner, P. R. Steric Crowding Can Stabilize a Labile Molecule: Solving the Hexaphenylethane Riddle. Angew. Chemie—Int. Ed. 2011, 50 (52), 12639-12642. https://doi.org/10.1002/anie.201103615.

(74) Danovich, D.; Shaik, S.; Neese, F.; Echeverría, J.; Aullón, G.; Alvarez, S. Understanding the Nature of the CH . . . HC Interactions in Alkanes. J. Chem. Theory Comput. 2013, 9 (4), 1977-1991. https://doi.org/10.1021/ct400070j.

(75) Wolters, L. P.; Koekkoek, R.; Bickelhaupt, F. M. Role of Steric Attraction and Bite-Angle Flexibility in Metal-Mediated C—H Bond Activation. ACS Catal. 2015, 5 (10), 5766-5775. https://doi.org/10.1021/acscatal.5b01354.

(76) Ahlquist, M. S. G.; Norrby, P. O. Dispersion and Back-Donation Gives Tetracoordinate [Pd(PPh 3)4]. Angew. Chemie—Int. Ed. 2011, 50 (49), 11794-11797. https://doi.org/10.1002/anie.201105928.

(77) Lyngvi, E.; Sanhueza, I. A.; Schoenebeck, F. Dispersion Makes the Difference: Bisligated Transition States Found for the Oxidative Addition of Pd(P-t-Bu3)2 to Ar—OSO2R and Dispersion-Controlled Chemoselectivity in Reactions with Pd[P(i-Pr)(t-Bu2)]2. Organometallics 2015, 34 (5), 805-812. https://doi.org/10.1021/om501199t.

(78) Minenkov, Y.; Occhipinti, G.; Heyndrickx, W.; Jensen, V. R. The Nature of the Barrier to Phosphane Dissociation from Grubbs Olefin Metathesis Catalysts. Eur. J. Inorg. Chem. 2012, No. 9, 1507-1516. https://doi.org/10.1002/ejic.201100932.

(79) Minenkov, Y.; Singstad, A.; Occhipinti, G.; Jensen, V. R. The Accuracy of DFT-Optimized Geometries of Functional Transition Metal Compounds: A Validation Study of Catalysts for Olefin Metathesis and Other Reactions in the Homogeneous Phase. Dalt. Trans. 2012, 41 (18), 5526-5541. https://doi.org/10.1039/c2dt12232d.

(80) Zhao, V.; Truhlar, D. G. Attractive Noncovalent Interactions in the Mechanism of Grubbs Second-Generation Ru Catalysts for Olefin Metathesis. Org. Lett. 2007, 9 (10), 1967-1970. https://doi.org/10.1021/ol705548.

(81) Sieffert, N.; Buhl, M. Noncovalent Interactions in a Transition-Metal Triphenylphosphine Complex: A Density Functional Case Study. Inorg. Chem. 2009, 48 (11), 4622-4624. https://doi.org/10.1021/ic900347e.

(82) Kalvet, I.; Deckers, K.; Funes-Ardoiz, I.; Magnin, G.; Sperger, T.; Kremer, M.; Schoenebeck, F. Selective Ortho-Functionalization of Adamantylarenes Enabled by Dispersion and an Air-Stable Palladium(I) Dimer. Angew. Chemie—Int. Ed. 2020, 59 (20), 7721-7725. https://doi.org/10.1002/anie.202001326.

(83) Yamakawa, M.; Yamada, I.; Noyori, R. CH/π Attraction: The Origin of Enantioselectivity in Transfer Hydrogenation of Aromatic Carbonyl Compounds Catalyzed by Chiral H6-Arene-Ruthenium(II) Complexes. Angew. Chemie—Int. Ed. 2001, 40 (15), 2818-2821. https://doi.org/10.1002/1521-3773(20010803)40:15<2818::AID-ANIE2818>3.0.CO;2-Y.

(84) Huber, R.; Passera, A.; Gubler, E.; Mezzetti, A. P-Stereogenic PN(H)P Iron(II) Catalysts for the Asymmetric Hydrogenation of Ketones: The Importance of Non-Covalent Interactions in Rational Ligand Design by Computation. Adv. Synth. Catal. 2018, 360 (15), 2900-2913. https://doi.org/10.1002/adsc.201800433.

(85) Mitani, M.; Tanaka, H.; Kojoh, S. I.; Matsugi, T.; Kashiwa, N.; Fujita, T.; Mohri, J. I.; Yoshida, Y.; Saito, J.; Ishii, S.; et al. Living Polymerization of Ethylene Catalyzed by Titanium Complexes Having Fluorine-Containing Phenoxy-Imine Chelate Ligands. J. Am. Chem. Soc. 2002, 124 (13), 3327-3336. https://doi.org/10.1021/ja0117581.

(86) Mitani, M.; Nakano, T.; Fujita, T. Unprecedented Living Olefin Polymerization Derived from an Attractive Interaction between a Ligand and a Growing Polymer Chain. Chem.—A Eur. J. 2003, 9 (11), 2396-2403. https://doi.org/10.1002/chem.200304661.

(87) Furuyama, R.; Mitani, M.; Mohri, J. I.; Mori, R.; Tanaka, H.; Fujita, T. Ethylene/Higher α-Olefin Copolymerization Behavior of Fluorinated Bis(Phenoxy-Imine) Titanium Complexes with Methylalumoxane: Synthesis of New Polyethylene-Based Block Copolymers. Macromolecules 2005, 38 (5), 1546-1552. https://doi.org/10.1021/ma0481104.

(88) Furuyama, R.; Saito, J.; Ishii, S.; Makio, H.; Mitani, M.; Tanaka, H.; Fujita, T. Fluorinated Bis(Phenoxy-Imine) Ti Complexes with MAO: Remarkable Catalysts for Living Ethylene and Syndioselective Living Propylene Polymerization. J. Organomet. Chem. 2005, 690 (20 SPEC. ISS.), 4398-4413. https://doi.org/10.1016/j.jorganchem.2005.03.060.

(89) Makio, H.; Fujita, S. Development and Application Fl Catalysis for Olefin Polymerization: Unique Catalysis and Distinctive Polymer Formation. Acc. Chem. Res. 2009, 42 (10), 1532-1544.

(90) Chan, M. C. W. Weak Attractive Ligand-Polymer and Related Interactions in Catalysis and Reactivity: Impact, Applications, and Modeling. Chem.—An Asian J. 2008, 3 (1), 18-27. https://doi.org/10.1002/asia.200700226.

(91) Kui, S. C. F.; Zhu, N.; Chan, M. C. W. Observation of Intramolecular C—H . . . F—C Contacts in Non-Metallocene Polyolefin Catalysts: Model for Weak Attractive Interactions between Polymer Chain and Noninnocent Ligand. Angew. Chemie—Int. Ed. 2003, 42 (14), 1628-1632. https://doi.org/10.1002/anie.200219832.

(92) Chan, M. C. W.; Kui, S. C. F.; Cole, J. M.; McIntyre, G. J.; Matsui, S.; Zhu, N.; Tam, K. H. Neutron and X-Ray Diffraction and Spectroscopic Investigations of Intramolecular [C—H . . . F—C] Contacts in Post-Metallocene Polyolefin Catalysts: Modeling Weak Attractive Polymer-Ligand Interactions. Chem.—A Eur. J. 2006, 12 (9), 2607-2619. https://doi.org/10.1002/chem.200501054.

(93) Talarico, G.; Busico, V.; Cavallo, L. "Living" Propene Polymerization with Bis(Phenoxyimine) Group 4 Metal Catalysts: New Strategies and Old Concepts. Organometallics 2004, 23 (25), 5989-5993. https://doi.org/10.1021/om049296y.

(94) Bryliakov, K. P.; Talsi, E. P.; Möller, H. M.; Baier, M. C.; Mecking, S. Noncovalent Interactions in O-Fluorinated Post-Titanocene Living Ethylene Polymerization Catalyst. Organometallics 2010, 29 (20), 4428-4430. https://doi.org/10.1021/om100729y.

(95) Lu, G.; Liu, R. Y.; Yang, Y.; Fang, C.; Lambrecht, D. S.; Buchwald, S. L.; Liu, P. Ligand-Substrate Dispersion Facilitates the Copper-Catalyzed Hydroamination of Unactivated Olefins. J. Am. Chem. Soc. 2017, 139 (46), 16548-16555. https://doi.org/10.1021/jacs.7b07373.

(96) Thomas, A. A.; Speck, K.; Kevlishvili, I.; Lu, Z.; Liu, P.; Buchwald, S. L. Mechanistically Guided Design of Ligands That Significantly Improve the Efficiency of CuH-Catalyzed Hydroamination Reactions. J. Am. Chem. Soc. 2018, 140 (42), 13976-13984. https://doi.org/10.1021/jacs.8b09565.

(97) Wang, H.; Park, Y.; Bai, Z.; Chang, S.; He, G.; Chen, G. Iridium-Catalyzed Enantioselective C(Sp3)-H Amidation Controlled by Attractive Noncovalent Interactions. J. Am. Chem. Soc. 2019, 141 (17), 7194-7201. https://doi.org/10.1021/jacs.9b02811.

(98) Fiammengo, R.; Bruinink, C. M.; Crego-Calama, M.; Reinhoudt, D. N. Noncovalent Secondary Interactions in Co(II)Salen Complexes: 02 Binding and Catalytic Activity in Cyclohexene Oxygenation. J. Org. Chem. 2002, 67 (24), 8552-8557. https://doi.org/10.1021/jo026118a.

(99) Echeverría, J.; Aullón, G.; Danovich, D.; Shaik, S.; Alvarez, S. Dihydrogen Contacts in Alkanes Are Subtle but Not Faint. Nat. Chem. 2011, 3 (4), 323-330. https://doi.org/10.1038/nchem.1004.

(100) Hwang, J.; Li, P.; Smith, M. D.; Shimizu, K. D. Distance-Dependent Attractive and Repulsive Interactions of Bulky Alkyl Groups. Angew. Chemie—Int. Ed. 2016, 55 (28), 8086-8089. https://doi.org/10.1002/anie.201602752.

(101) Reddi, Y.; Tsai, C. C.; Avila, C. M.; Toste, F. D.; Sunoj, R. B. Harnessing Noncovalent Interactions in Dual-Catalytic Enantioselective Heck-Matsuda Arylation. J. Am. Chem. Soc. 2019, 141 (2), 998-1009. https://doi.org/10.1021/jacs.8b11062.

(102) Malakar, S.; Shree Sowndarya, S. V.; Sunoj, R. B. A Quantification Scheme for Non-Covalent Interactions in the Enantio-Controlling Transition States in Asymmetric Catalysis. Org. Biomol. Chem. 2018, 16 (31), 5643-5652. https://doi.org/10.1039/c8ob01158c.

(103) Yang, L.; Adam, C.; Nichol, G. S.; Cockroft, S. L. How Much Do van Der Waals Dispersion Forces Contribute to Molecular Recognition in Solution? Nat. Chem. 2013, 5 (12), 1006-1010. https://doi.org/10.1038/nchem.1779.

(104) Strauss, M. A.; Wegner, H. A. Molecular Systems for the Quantification of London Dispersion Interactions. European J. Org. Chem. 2019, 2019 (2), 295-302. https://doi.org/10.1002/ejoc.201800970.

(105) Pollice, R.; Bot, M.; Kobylianskii, I. J.; Shenderovich, I.; Chen, P. Attenuation of London Dispersion in Dichloromethane Solutions. J. Am. Chem. Soc. 2017, 139 (37), 13126-13140. https://doi.org/10.1021/jacs.7b06997.

(106) Horn, P. R.; Mao, Y.; Head-Gordon, M. Probing Non-Covalent Interactions with a Second Generation Energy Decomposition Analysis Using Absolutely Localized Molecular Orbitals. Phys. Chem. Chem. Phys. 2016, 18 (33), 23067-23079. https://doi.org/10.1039/c6cp03784d.

(107) Frisch, M. J.; Trucks, G. W.; Schlegel, H. B.; Scuseria, G. E.; Robb, M. A.; Cheeseman, J. R.; Scalmani, G.; Barone, V.; Petersson, G. A.; Nakatsuji, H.; et al. Gaussian16, Rev. A.01. Gaussian Inc.: Wallingford, C T 2016.

(108) Becke, A. D. Density-Functional Thermochemistry. III. The Role of Exact Exchange. J. Chem. Phys. 1993, 98 (7), 5648-5652. https://doi.org/10.1063/1.464913.
(109) Lee, C.; Yang, W.; Parr, R. G. Development of the Colle-Salvetti Correlation-Energy Formula into a Functional of the Electron Density. Phys. Rev. B 1988, 37 (2), 785-789. https://doi.org/10.1103/PhysRevB.37.785.
(110) Grimme, S.; Huenerbein, R.; Ehrlich, S. On the Importance of the Dispersion Energy for the Thermodynamic Stability of Molecules. ChemPhysChem 2011, 12 (7), 1258-1261. https://doi.org/10.1002/cphc.201100127.
(111) Grimme, S.; Hansen, A.; Brandenburg, J. G.; Bannwarth, C. Dispersion-Corrected Mean-Field Electronic Structure Methods. Chem. Rev. 2016, 116 (9), 5105-5154. https://doi.org/10.1021/acs.chemrev.5b00533.
(112) Lu, T.; Chen, F. Multiwfn: A Multifunctional Wavefunction Analyze. J. Comput. Chem. 2012, 33 (5), 580-592.
(113) Humphrey, W.; Dalke, A.; Schulten, K. VMD—Visual Molecular Dynamics. J. Molec. Graph. 1996, 13, 33-38.
(114) Shao, Y.; Gan, Z.; Epifanovsky, E.; Gilbert, A. T. B.; Wormit, M.; Kussmann, J.; Lange, A. W.; Behn, A.; Deng, J.; Feng, X.; et al. Advances in Molecular Quantum Chemistry Contained in the Q-Chem 4 Program Package. Mol. Phys. 2015, 113 2), 184-215. https://doi.org/10.1080/00268976.2014.952696.
(115) Lane, A.; Coussens, B. B.; Hirvi, J. T.; Berthoud, A.; Friederichs, N.; Severn, J. R.; Linnolahti, M. Effect of Ligand Structure on Olefin Polymerization by a Metallocene/Borate Catalyst: A Computational Study. Organometallics 2015, 34 (11), 2415-2421. https://doi.org/10.1021/om501185x.
(116) Margl, P.; Deng, L.; Ziegler, T. General Aspects of Ethylene Polymerization by D0 and D0fn Transition Metals. Top. Catal. 1999, 7, 187-208.

We claim:

1. A method for designing a Group 4 metallocene olefin polymerization catalyst, the method comprising:
   (a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework;
   (b) generating (1) a first transition state model structure ($TS^{A1}$) derived from migratory insertion of an ethylene molecule into a metal-hydrocarbyl ligand bond of the first metallocene catalyst framework and (2) a second transition state model structure ($TS^{A2}$) derived from migratory insertion of an α-olefin co-monomer molecule into the metal-hydrocarbyl ligand bond of the first metallocene catalyst framework;
   (c) determining, by at least one processor of a device, relative energies of each of the first ground state model structure ($GS^A$), the first transition state model structure ($TS^{A1}$), a dispersion energy (Disp $E^{A1}$) associated with $TS^{A1}$, the second transition state model structure ($TS^{A2}$), and a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A1}-GS^A$), $\Delta\Delta G^{\ddagger A}$ ($TS^{A2}-TS^{A1}$) and an absolute difference in dispersion energies |$\Delta$Disp $E^A$| calculated as |$\Delta$(Disp $E^{A2}$–Disp $E^{A1}$)| for migratory insertion of the ethylene molecule versus the α-olefin co-monomer molecule in the first metallocene catalyst framework;
   (d) repeating steps (a)-(c) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^B$), and fourth transition state model structure ($TS^{B2}$), and determining, by at least one processor of a device, relative energies of each of a $GS^B$, $TS^{B1}$, a dispersion energy (Disp $E^{B1}$) associated with $TS^{B1}$, $TS^{B2}$, and a dispersion energy (Disp $E^{B2}$) associated with $TS^{B2}$, and determining values for $\Delta G^{\ddagger B1}$($TS^{B1}-GS^B$), $\Delta G^{\ddagger B2}$ ($TS^{B2}-GS^B$), $\Delta\Delta G^{\ddagger B}$ ($TS^{B2}-TS^{B1}$) and an absolute difference in dispersion energies |$\Delta$Disp $E^B$| calculated as |$\Delta$(Disp $E^{B2}$–Disp $E^{B1}$)| for migratory insertion of the ethylene molecule versus the α-olefin co-monomer molecule in the second metallocene catalyst framework; and
   (e) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B}<\Delta\Delta G^{\ddagger A}$, when |$\Delta$Disp $E^B$|>|$\Delta$Disp $E^A$|, or a combination thereof, or (2) enhancing ethylene incorporation into a polyethylene co-polymer relative to the first metallocene catalyst framework when $\Delta\Delta G^{\ddagger B}>\Delta\Delta G^{\ddagger A}$, when |$\Delta$Disp $E^B$|<|$\Delta$Disp $E^A$|, or a combination thereof.

2. The method for designing a Group 4 metallocene olefin polymerization catalyst according to claim 1, further comprising steps of:
   (f) repeating steps (a)-(c) using a third metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, relative energies of each of a $GS^C$, $TS^{C1}$, a dispersion energy (Disp $E^{C1}$) associated with $TS^{C1}$, $TS^{C2}$, and a dispersion energy (Disp $E^{C2}$) associated with $TS^{C2}$, and determining values for $\Delta G^{\ddagger C1}$ ($TS^{C1}-GS^C$), $\Delta G^{\ddagger C2}$ ($TS^{C2}-GS^C$), $\Delta\Delta G^{\ddagger C}$ ($TS^{C2}-TS^{C1}$) and an absolute difference in dispersion energies |$\Delta$Disp $E^C$| calculated as |$\Delta$(Disp $E^{C2}$–Disp $E^{C1}$)| for migratory insertion of the ethylene molecule versus the α-olefin co-monomer molecule in the third metallocene catalyst framework; and
   (g) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C}<\Delta\Delta G^{\ddagger A}$, when |$\Delta$Disp $E^C$|>|$\Delta$Disp $E^A$|, or a combination thereof, (2) enhancing ethylene incorporation into a polyethylene co-polymer relative to the first metallocene catalyst framework when $\Delta\Delta G^{\ddagger C}>\Delta\Delta G^{\ddagger A}$, when |$\Delta$Disp $E^C$|<|$\Delta$Disp $E^A$|, or a combination thereof, (3) enhancing α-olefin co-monomer incorporation into a polyethylene co-polymer relative to the second metallocene catalyst framework when $\Delta\Delta G^{\ddagger C}<\Delta\Delta G^{\ddagger B}$, when |$\Delta$Disp $E^C$|>|$\Delta$Disp $E^B$|, or a combination thereof, or (4) enhancing ethylene incorporation into a polyethylene co-polymer relative to the second metallocene catalyst framework when $\Delta\Delta G^{\ddagger C} > \Delta\Delta G^{\ddagger B}$, when $|\Delta \text{Disp } E^C| < |\Delta \text{Disp } E^B|$, or a combination thereof.

3. The method for designing a Group 4 metallocene olefin polymerization catalyst according to claim 1, wherein:
the first test substituent of the second metallocene catalyst framework is identified as enhancing α-olefin co-monomer incorporation or enhancing ethylene incorporation into the polyethylene co-polymer based upon the relative energies of $\Delta\Delta G^{\ddagger B} < \Delta\Delta G^{\ddagger A}$.

4. The method for designing a Group 4 metallocene olefin polymerization catalyst according to claim 1, wherein:
the first test substituent of the second metallocene catalyst framework is identified as enhancing α-olefin co-monomer incorporation or enhancing ethylene incorporation into the polyethylene co-polymer based upon the relative energies of $|\Delta\text{Disp } E^B| > |\Delta\text{Disp } E^A|$.

5. The method for designing a Group 4 metallocene olefin polymerization catalyst according to claim 1, wherein:
the first test substituent of the second metallocene catalyst framework is identified as enhancing α-olefin co-monomer incorporation or enhancing ethylene incorporation into the polyethylene co-polymer based upon the relative energies of both $\Delta\Delta G^{\ddagger B} < \Delta\Delta G^{\ddagger A}$ and $|\Delta\text{Disp } E^B| > |\Delta\text{Disp } E^A|$.

6. The method for designing a Group 4 metallocene olefin polymerization catalyst according to claim 1, wherein the relative energies of any one or more of the ground state model structures and any one or more of the transition state model structures is calculated as a B3LYP single point energy calculation with a D3BJ correction (B3LYP+D3BJ) using a density functional theory (DFT).

7. The method for designing a Group 4 metallocene olefin polymerization catalyst according to claim 1, wherein any one or more of the dispersion energies is calculated as the difference between a B3LYP single point energy calculation with and without a D3BJ correction using a density functional theory (DFT).

8. The method for designing a Group 4 metallocene olefin polymerization catalyst according to claim 1, wherein the first test substituent is selected from: a halide (F, Cl, or Br); a $C_1$-$C_{10}$ heterohydrocarbyl group comprising a heteroatom selected from halide (F, Cl, or Br), N, O, P, or S; a $C_1$-$C_{10}$ aliphatic group; or a $C_6$-$C_{10}$ aromatic group.

9. The method for designing a Group 4 metallocene olefin polymerization catalyst according to claim 1, wherein the first test substituent is selected from F, Cl, Br, substituted or unsubstituted $C_1$-$C_6$ alkyl, substituted or unsubstituted $C_6$-$C_{10}$ aryl, $C_1$-$C_6$ alkoxide, —OC(O)$R^1$, —CH$_2$C(O)$R^1$, —NR$^1_2$, —PH$_3$, PR$^1_3$, or —SR$^1$, wherein $R^1$ is independently selected from a $C_1$-$C_6$ alkyl or a $C_6$-$C_{10}$ aryl.

10. The method for designing a Group 4 metallocene olefin polymerization catalyst according to claim 1, wherein the hydrocarbyl ligand is a $C_1$-$C_6$ hydrocarbyl ligand, or alternatively a $C_1$-$C_4$ hydrocarbyl ligand, or alternatively an ethyl ($C_2$) ligand, and the α-olefin co-monomer comprises or is selected from propylene, 1-butene, 1-pentene, 1-hexene, 1-heptene, 1-octene, or styrene.

11. The method for designing a Group 4 metallocene olefin polymerization catalyst according to claim 1, wherein the substituted or unsubstituted $\eta^5$-cycloalkadienyl ligands, absent the first test substituent, are selected independently from cyclopentadienyl, methylcyclopentadienyl, t-butylcyclopentadienyl, indenyl, 4-phenyl-indenyl, 2-methylindenyl, 3-t-butylindenyl, 2-methyl-4-phenylindenyl, fluorenyl, or 2-methylfluorenyl.

12. The method for designing a Group 4 metallocene olefin polymerization catalyst according to claim 1, wherein:
the first metallocene catalyst framework comprises two independently selected substituted or unsubstituted $\eta^5$-cycloalkadienyl ligands; or
the first metallocene catalyst framework comprises two independently selected substituted or unsubstituted $\eta^5$-cycloalkadienyl ligands which are bridged by a linking group of the formula (1) >ER'R$^2$, wherein E is C or Si, $R^1$ is hydrogen or a $C_1$-$C_{12}$ hydrocarbyl group, and $R^2$ is hydrogen, a $C_1$-$C_{12}$ hydrocarbyl group, or a $C_3$-$C_{10}$ alkenyl group having a terminal C=C double bond, or (2) CR$^1_2$CR$^2$—, wherein $R^1$ and $R^2$ are selected independently from hydrogen or a $C_1$-$C_6$ hydrocarbyl group.

13. The method for designing a Group 4 metallocene olefin polymerization catalyst according to claim 1, wherein the first metallocene catalyst framework comprises one of the following structures:

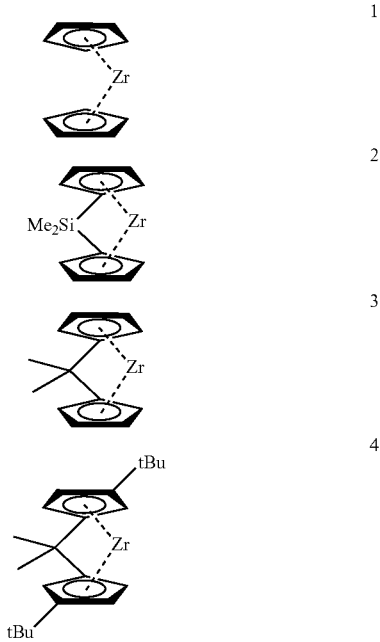

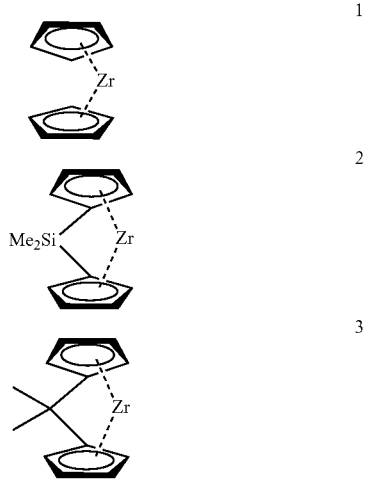

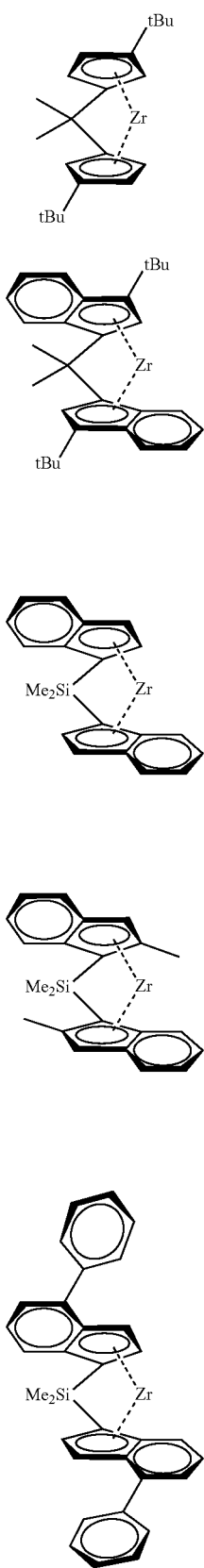

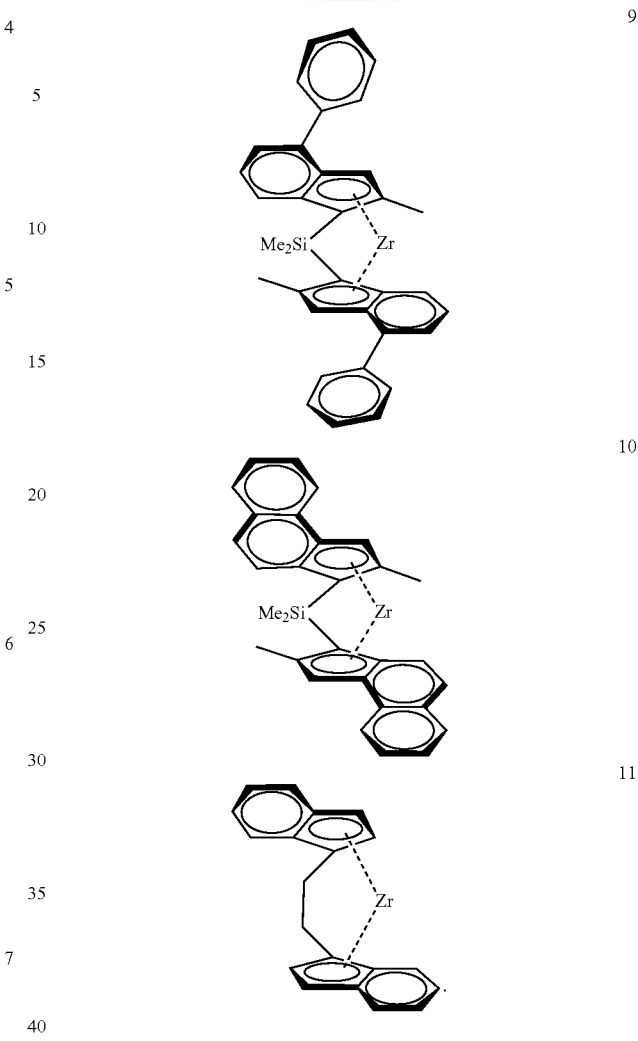

14. The method for designing a Group 4 metallocene olefin polymerization catalyst according to claim 1, further comprising a step of synthesizing the Group 4 metallocene catalyst comprising the one or two independently selected substituted or unsubstituted $\eta^5$-cycloalkadienyl ligands, wherein at least one of the $\eta^5$-cycloalkadienyl ligands comprises the first test substituent.

15. The method for designing a Group 4 metallocene olefin polymerization catalyst according to claim 2, further comprising steps of:
   providing a Group 4 metallocene catalyst comprising the one or two independently selected substituted or unsubstituted $\eta^5$-cycloalkadienyl ligands, wherein at least one of the $\eta^5$-cycloalkadienyl ligands comprises the first test substituent or the second test substituent; and
   contacting the Group 4 metallocene catalyst with ethylene and an α-olefin co-monomer molecule under polymerization conditions to form a polyethylene co-polymer.

16. A method for designing a Group 4 metallocene olefin polymerization catalyst, the method comprising:
   (a) selecting a first metallocene catalyst framework comprising a Group 4 metal bonded to a hydrocarbyl ligand and to one or two independently selected substituted or unsubstituted $\eta^5$-cycloalkadienyl ligands, and generating a first ground state model structure ($GS^A$) derived from the first metallocene catalyst framework;

(b) generating (1) a first transition state model structure ($TS^{A1}$) derived from migratory insertion of an ethylene molecule into a metal-hydrocarbyl ligand bond of the first metallocene catalyst framework and (2) a second transition state model structure ($TS^{A2}$) derived from migratory insertion of an α-olefin co-monomer molecule into the metal-hydrocarbyl ligand bond of the first metallocene catalyst framework;

(c) determining, by at least one processor of a device, relative energies of each of the first ground state model structure ($GS^A$), the first transition state model structure ($TS^{A1}$), a dispersion energy (Disp $E^{A1}$) associated with $TS^{A1}$, the second transition state model structure ($TS^{A2}$), and a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A2}-GS^A$), and $\Delta\Delta G^{\ddagger A}$ ($TS^{A2}-TS^{A1}$) for migratory insertion of the ethylene molecule versus the α-olefin molecule in the first metallocene catalyst framework;

(d) determining, by at least one processor of a device, a number of stabilizing, non-covalent (dispersion-type) interactions (NCI) within a distance of from 2.5 Å to 4.0 Å, inclusive, between (1) the ethylene molecule and the substituted or unsubstituted $\eta^5$-cycloalkadienyl ligands in the first transition state model structure $TS^{A1}$ ($NCI^{A1}$), and (2) the α-olefin molecule and the substituted or unsubstituted $\eta^5$-cycloalkadienyl ligands in the second transition state model structure $TS^{A2}$ ($NCI^{A2}$), and difference between the number of these NCI interactions ($\Delta NCI^A$);

(e) repeating steps (a)-(d) using a second metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, relative energies of each of a $GS^B$, $TS^{B1}$, including a dispersion energy (Disp $E^{B1}$) associated with $TS^{B1}$, $TS^{B2}$, and a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta\Delta G^{\ddagger B}$ ($TS^{B2}-TS^{B1}$) and a number of stabilizing, non-covalent (dispersion-type) interactions in $TS^{B1}$ ($NCI^{B1}$) and $TS^{B2}$ ($NCI^{B2}$), and difference between the numbers of these NCI interactions ($\Delta NCI^B$), for migratory insertion of the ethylene molecule versus the α-olefin molecule in the second metallocene catalyst framework; and (f) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B}<\Delta\Delta G^{\ddagger A}$, when $\Delta NCI^B>\Delta NCI^A$, or a combination thereof, or (2) enhancing ethylene incorporation into a polyethylene co-polymer relative to the first metallocene catalyst framework when $\Delta\Delta G^{\ddagger B}>\Delta\Delta G^{\ddagger A}$, when $\Delta NCI^B<\Delta NCI^A$, or a combination thereof.

17. The method for designing a Group 4 metallocene olefin polymerization catalyst according to claim 16, further comprising steps of:

(g) repeating steps (a)-(d) using a third metallocene catalyst framework comprising the Group 4 metal bonded to the hydrocarbyl ligand and to the one or two independently selected $\eta^5$-cycloalkadienyl ligands, wherein at least one of the $\eta^5$-cycloalkadienyl ligands comprises a second test substituent, and generating a corresponding third ground state model structure ($GS^C$), fifth transition state model structure ($TS^{C1}$), and sixth transition state model structure ($TS^{C2}$), and determining, by at least one processor of a device, relative energies of each of a $GS^C$, $TS^{C1}$, including a dispersion energy (Disp $E^{C1}$) associated with $TS^{C1}$, $TS^{C2}$, and a dispersion energy (Disp $E^{C2}$) associated with $TS^{C2}$, and determining values for $\Delta G^{\ddagger C1}$ ($TS^{C1}-GS^C$), $\Delta G^{\ddagger C2}$ ($TS^{C2}-GS^C$), $\Delta\Delta G^{\ddagger C}$ ($TS^{C2}-TS^{C1}$) and the number of stabilizing, non-covalent (dispersion-type) interactions in $TS^{C1}$ ($NCI^{C1}$) and $TS^{C2}$ ($NCI^{C2}$), and difference between the numbers of these NCI interactions ($\Delta NCI^C$), for migratory insertion of the ethylene molecule versus the α-olefin molecule in the second metallocene catalyst framework; and (h) identifying the second test substituent of the third metallocene catalyst framework as (1) enhancing α-olefin co-monomer incorporation into a polyethylene co-polymer relative to the first metallocene catalyst framework when $\Delta\Delta G^{\ddagger C}<\Delta\Delta G^{\ddagger A}$, when $\Delta NCI^C>\Delta NCI^A$, or a combination thereof, (2) enhancing ethylene incorporation into a polyethylene co-polymer relative to the first metallocene catalyst framework when $\Delta\Delta G^{\ddagger C}>\Delta\Delta G^{\ddagger A}$, when $\Delta NCI^C<\Delta NCI^A$ or a combination thereof, (3) enhancing α-olefin co-monomer incorporation into a polyethylene co-polymer relative to the second metallocene catalyst framework when $\Delta\Delta G^{\ddagger C}<\Delta\Delta G^{\ddagger B}$, when $\Delta NCI^C>\Delta NCI^B$, or a combination thereof, or (4) enhancing ethylene incorporation into a polyethylene co-polymer relative to the second metallocene catalyst framework when $\Delta\Delta G^{\ddagger C}>\Delta\Delta G^{\ddagger B}$, when $\Delta NCI^C<\Delta NCI^B$, or a combination thereof.

18. The method for designing a Group 4 metallocene olefin polymerization catalyst according to claim 16, wherein any of the number of stabilizing, non-covalent (dispersion-type) interactions are calculated using absolutely localized molecular orbital energy decomposition analysis (ALMO-EDA) of the respective transition state model structures.

19. The method for designing a Group 4 metallocene olefin polymerization catalyst according to claim 16, wherein a number of non-covalent (dispersion-type) interactions $NCI^A$, $NCI^B$, and $NCI^C$ within a distance of from 2.5 Å to 4.0 Å comprises the number of CH—H, CH—X (X=F, Cl, Br, N, O), and CH-π interactions between the ethylene molecule or the α-olefin molecule and the substituted or unsubstituted $\eta^5$-cycloalkadienyl ligands and the first test substituent of the second metallocene catalyst framework within a distance range of 2.5 to 4.0 Å.

20. The method for designing a Group 4 metallocene olefin polymerization catalyst according to claim 16, wherein:

the first test substituent of the second metallocene catalyst framework is identified as enhancing α-olefin co-monomer incorporation or enhancing ethylene incorporation into the polyethylene co-polymer based upon the relative energies of $\Delta\Delta G^{\ddagger B}<\Delta\Delta G^{\ddagger A}$.

21. The method for designing a Group 4 metallocene olefin polymerization catalyst according to claim 17, wherein:

the first test substituent of the second metallocene catalyst framework is identified as enhancing α-olefin co-monomer incorporation or enhancing ethylene incorporation into the polyethylene co-polymer based upon $\Delta NCI^B > \Delta NCI^A$.

22. The method for designing a Group 4 metallocene olefin polymerization catalyst according to claim 17, wherein:
the first test substituent of the second metallocene catalyst framework is identified as enhancing α-olefin co-monomer incorporation or enhancing ethylene incorporation into the polyethylene co-polymer based upon the relative energies of $\Delta\Delta G^{\ddagger B} < \Delta\Delta G^{\ddagger A}$ and based upon $\Delta NCI^B > \Delta NCI^A$.

23. A catalyst system for polymerizing olefins, comprising:
a Group 4 metallocene olefin polymerization catalyst designed according to a method comprising:
(a) selecting a first metallocene catalyst framework comprising a Group 4 metal bonded to a hydrocarbyl ligand and to one or two independently selected substituted or unsubstituted η⁵-cycloalkadienyl ligands, and generating a first ground state model structure ($GS^A$) derived from the first metallocene catalyst framework;
(b) generating (1) a first transition state model structure ($TS^{A1}$) derived from migratory insertion of an ethylene molecule into a metal-hydrocarbyl ligand bond of the first metallocene catalyst framework and (2) a second transition state model structure ($TS^{A2}$) derived from migratory insertion of an α-olefin co-monomer molecule into the metal-hydrocarbyl ligand bond of the first metallocene catalyst framework;
(c) determining, by at least one processor of a device, relative energies of each of the first ground state model structure ($GS^A$), the first transition state model structure ($TS^{A1}$), a dispersion energy (Disp $E^{A1}$) associated with $TS^{A1}$, the second transition state model structure ($TS^{A2}$), and a dispersion energy (Disp $E^{A2}$) associated with $TS^{A2}$, and determining values for $\Delta G^{\ddagger A1}$ ($TS^{A1}-GS^A$), $\Delta G^{\ddagger A2}$ ($TS^{A1}-GS^A$), $\Delta\Delta G^{\ddagger A}$ ($TS^{A2}-TS^{A1}$), and an absolute difference in dispersion energies $|\Delta Disp\ E^A|$ calculated as $|\Delta(Disp\ E^{A2}-Disp\ E^{A1})|$ for migratory insertion of the ethylene molecule versus the α-olefin co-monomer molecule in the first metallocene catalyst framework;
(d) repeating steps (a)-(c) using a second metallocene catalyst framework comprising the Group 4 metal bonded to the hydrocarbyl ligand and to the one or two independently selected η⁵-cycloalkadienyl ligands, wherein at least one of the η⁵-cycloalkadienyl ligands comprises a first test substituent, and generating a corresponding second ground state model structure ($GS^B$), third transition state model structure ($TS^{B1}$), and fourth transition state model structure ($TS^{B2}$), and determining, by at least one processor of a device, relative energies of each of a $GS^B$, $TS^{B1}$, a dispersion energy (Disp $E^{B1}$) associated with $TS^{B1}$, $TS^{B2}$, and a dispersion energy (Disp $E^{B2}$) associated with $TS^{B2}$, and determining values for $\Delta G^{\ddagger B1}$ ($TS^{B1}-GS^B$), $\Delta G^{\ddagger B2}$ ($TS^{B2}-GS^B$), $\Delta\Delta G^{\ddagger B}$ ($TS^{B2}-TS^{B1}$), and an absolute difference in dispersion energies $|\Delta Disp\ E^B|$ calculated as $|\Delta(Disp\ E^{B2}-Disp\ E^{B1})|$ for migratory insertion of the ethylene molecule versus the α-olefin co-monomer molecule in the second metallocene catalyst framework; and (e) identifying the first test substituent of the second metallocene catalyst framework as (1) enhancing α-olefin co-monomer incorporation into a polyethylene co-polymer relative to the first metallocene catalyst framework when $\Delta\Delta G^{\ddagger B} < \Delta\Delta G^{\ddagger A}$, when $|\Delta Disp\ E^B| > |\Delta Disp\ E^A|$, or a combination thereof, or (2) enhancing ethylene incorporation into a polyethylene co-polymer relative to the first metallocene catalyst framework when $\Delta\Delta G^{\ddagger B} > \Delta\Delta G^{\ddagger A}$, when $|\Delta Disp\ E^B| < |\Delta Disp\ E^A|$, or a combination thereof;
wherein the Group 4 metal is bonded to the hydrocarbyl ligand and to the one or two independently selected substituted or unsubstituted η⁵-cycloalkadienyl ligands;
wherein at least one of the η⁵-cycloalkadienyl ligands comprises the first test substituent which is identified as enhancing olefin co-monomer incorporation into a polyethylene co-polymer, relative to an olefin co-monomer incorporation of the first metallocene catalyst framework, and
wherein the first metallocene catalyst framework comprises the following structure:

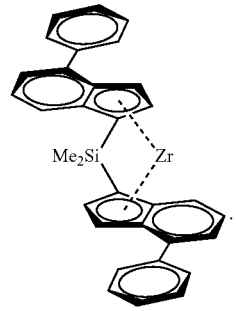

* * * * *